United States Patent
Wei et al.

(10) Patent No.: US 11,820,797 B2
(45) Date of Patent: *Nov. 21, 2023

(54) ELICITOR PEPTIDES HAVING DISRUPTED HYPERSENSITIVE RESPONSE BOX AND USE THEREOF

(71) Applicant: Plant Health Care, Inc., Holly Springs, NC (US)

(72) Inventors: Zhongmin Wei, Kirkland, WA (US); Gregory A. Zornetzer, Seattle, WA (US)

(73) Assignee: PLANT HEALTH CARE, INC., Holly Springs, NC (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/147,183

(22) Filed: Jan. 12, 2021

(65) Prior Publication Data

US 2021/0238234 A1    Aug. 5, 2021

Related U.S. Application Data

(63) Continuation of application No. 15/244,862, filed on Aug. 23, 2016, now Pat. No. 10,918,104, which is a continuation of application No. 14/872,347, filed on Oct. 1, 2015, now Pat. No. 10,743,538.

(60) Provisional application No. 62/186,527, filed on Jun. 30, 2015, provisional application No. 62/058,535, filed on Oct. 1, 2014.

(51) Int. Cl.
| | |
|---|---|
| C07K 14/195 | (2006.01) |
| C07K 14/21 | (2006.01) |
| C07K 14/27 | (2006.01) |
| C12N 15/82 | (2006.01) |
| A01N 63/50 | (2020.01) |
| A01N 37/46 | (2006.01) |
| C07K 14/00 | (2006.01) |
| C07K 7/08 | (2006.01) |

(52) U.S. Cl.
CPC ............ *C07K 14/195* (2013.01); *A01N 37/46* (2013.01); *A01N 63/50* (2020.01); *C07K 7/08* (2013.01); *C07K 14/001* (2013.01); *C07K 14/21* (2013.01); *C07K 14/27* (2013.01); *C12N 15/8279* (2013.01); *C12N 15/8283* (2013.01); *C07K 2319/00* (2013.01); *C07K 2319/20* (2013.01)

(58) Field of Classification Search
None
See application file for complete search history.

(56) References Cited

U.S. PATENT DOCUMENTS

| | | |
|---|---|---|
| 5,473,039 A | 12/1995 | Dyer et al. |
| 5,776,889 A | 7/1998 | Wei et al. |
| 5,859,339 A | 1/1999 | Ronald et al. |
| 5,977,060 A | 11/1999 | Zitter et al. |
| 6,235,974 B1 | 5/2001 | Qiu et al. |
| 6,277,814 B1 | 8/2001 | Qiu et al. |
| 6,310,176 B1 | 10/2001 | Barra et al. |
| 6,563,020 B1 | 5/2003 | Simmons et al. |
| 6,624,139 B1 | 9/2003 | Wei et al. |
| 6,858,707 B1 | 2/2005 | Wei et al. |
| 7,132,393 B2 | 11/2006 | Summerton |
| 7,132,525 B2 | 11/2006 | Laby et al. |
| 8,440,881 B2 | 5/2013 | Park et al. |
| 8,686,224 B2 | 4/2014 | Ryan, deceased et al. |
| 9,109,039 B2 | 8/2015 | Ryan et al. |
| 10,524,473 B2 * | 1/2020 | Wei ...................... C07K 14/001 |
| 10,918,104 B2 * | 2/2021 | Wei ........................ C07K 7/08 |
| 2002/0007501 A1 | 1/2002 | Song et al. |
| 2002/0019337 A1 | 2/2002 | Wei et al. |
| 2002/0062500 A1 | 2/2002 | Fan |
| 2002/0059658 A1 | 5/2002 | Wei et al. |
| 2003/0104979 A1 | 6/2003 | Wei et al. |
| 2004/0073977 A1 | 4/2004 | Misra |
| 2005/0250699 A1 | 10/2005 | Kristensen et al. |

(Continued)

FOREIGN PATENT DOCUMENTS

| | | |
|---|---|---|
| CN | 1793172 | 6/2006 |
| CN | 101284876 | 10/2008 |

(Continued)

OTHER PUBLICATIONS

Examination Report in India Patent Application No. 201747014535, dated Oct. 13, 2021.

NCBI Reference Sequence: XP_005763286.1, hypothetical protein EMIHUDRAFT_104952 [Emiliania huxleyi CCMP1516] (Apr. 7, 2015).

(Continued)

*Primary Examiner* — Sudhakar Katakam

*Assistant Examiner* — Zachary J Miknis

(74) *Attorney, Agent, or Firm* — Troutman Pepper Hamilton Sanders LLP (Rochester)

(57) ABSTRACT

Disclosed are peptides that induce an active plant response, but not a hypersensitive response, when applied to plant tissue. These peptides also preferably exhibit improved solubility, stability, resistance to chemical degradation, or a combination of these properties. Use of these peptides or fusion polypeptides, or DNA constructs encoding the same, for modulating plant biochemical signaling, imparting disease resistance to plants, enhancing plant growth, imparting tolerance to biotic stress, imparting tolerance and resistance to abiotic stress, imparting desiccation resistance to cuttings removed from ornamental plants, imparting post-harvest disease or post-harvest desiccation resistance to a fruit or vegetable, or enhancing the longevity of fruit or vegetable ripeness are also disclosed.

24 Claims, No Drawings

Specification includes a Sequence Listing.

(56) References Cited

U.S. PATENT DOCUMENTS

| | | | |
|---|---|---|---|
| 2006/0193774 | A1 | 8/2006 | Summerton |
| 2006/0248617 | A1 | 11/2006 | Imanaka et al. |
| 2009/0118134 | A1 | 5/2009 | Vrijloeb et al. |
| 2009/0300802 | A1 | 12/2009 | Ryan et al. |
| 2010/0043095 | A1 | 2/2010 | Wei |
| 2011/0191896 | A1 | 8/2011 | Pitkin et al. |
| 2011/0233469 | A1 | 9/2011 | Petersen |
| 2012/0265513 | A1 | 10/2012 | Fang et al. |
| 2013/0116119 | A1 | 5/2013 | Rees et al. |
| 2013/0125258 | A1 | 5/2013 | Emmanuel et al. |
| 2013/0150288 | A1 | 6/2013 | Dobson |
| 2013/0172185 | A1 | 7/2013 | Wei |
| 2013/0274104 | A1 | 10/2013 | Reddig et al. |
| 2013/0298287 | A1 | 11/2013 | Park et al. |
| 2014/0090103 | A1 | 3/2014 | Pitkin et al. |
| 2014/0227767 | A2 | 3/2014 | Yeaman et al. |
| 2015/0218099 | A1 | 8/2015 | Mann |
| 2016/0095314 | A1 | 4/2016 | Wei et al. |
| 2016/0297853 | A1 | 10/2016 | Wei et al. |
| 2016/0353736 | A1 | 12/2016 | Wei et al. |

FOREIGN PATENT DOCUMENTS

| | | |
|---|---|---|
| CN | 101892244 | 11/2010 |
| CN | 103103202 | 5/2013 |
| CN | 1454989 | 11/2013 |
| CN | 106831964 | 6/2017 |
| EP | 1997502 | 12/2008 |
| EP | 2168592 | 3/2010 |
| EP | 1930025 | 6/2018 |
| WO | 95/31564 | 11/1995 |
| WO | 98/06748 | 2/1998 |
| WO | 99/02655 | 7/1998 |
| WO | 99/37664 | 7/1999 |
| WO | 00/020452 A2 | 4/2000 |
| WO | 00/28056 | 5/2000 |
| WO | 01/055335 | 8/2001 |
| WO | 01/80639 | 11/2001 |
| WO | 01/98501 | 12/2001 |
| WO | 2002/022821 | 3/2002 |
| WO | 2005/014639 A2 | 2/2005 |
| WO | 2005/017158 | 2/2005 |
| WO | 2005/115444 A2 | 12/2005 |
| WO | 2006/077601 | 7/2006 |
| WO | 2008/104598 A2 | 9/2008 |
| WO | 2010/019442 | 2/2010 |
| WO | 2010/042654 | 4/2010 |
| WO | 2013/039857 A1 | 3/2013 |
| WO | 2013/102189 | 7/2013 |

OTHER PUBLICATIONS

NCBI Reference Sequence: WP_024712781.1, hypothetical protein [Xanthomonas oryzae] (May 23, 2014).
GenBank: CCF68205.1, Hpa1 protein [Xanthomonas citri pv. punicae str. LMG 859] (Aug. 21, 2013).
Examination Report for EP 15845670.7 (dated Jul. 3, 2021).
Takuro et al., "Effect of amino acid substitution in amphiphilic [alpha]-helical peptides on peptide-phospholipid membrane interaction", Journal of peptide science, vol. 5, No. 7, Jul. 1999, pp. 298-305.
Examination Report European Patent Application No. 15845670.7 (dated Jun. 30, 2020).
STN File Registry RN 153512-20-0 (1994).
STN File Registry RN 220893-47-0 (1999).
STN File Registry RN 220922-27-0 (1999).
Office Action for U.S. Appl. No. 15/244,919 (dated Nov. 27, 2018).
NCBI Reference No. WP_082338630 (Apr. 11, 17).
NCBI Reference No. WP_014505138.1 (May 19, 17).
Inoue et al., "The HrpZ and HrpA Genes are Variable, and Useful for Grouping Pseudomonas Syringae Bacteria," Journal of General Plant Pathology 72(1):26-33 (2006).
Shrestha et al., "The Hrp Gene Cluster in Erwinia Pyrifoliae and Determination of HR Active Domain in HrpNEp Protein," ISHS Acta Horticulturae 793: XI International Workshop on Fire Blight. (2008).
Lee et al., "Relationship Between Antimicrobial Activity and Amphiphilic Property of Basic Model Peptides," Biochimica Biophysica Acta (BBA)-Biomembranes 862(1):211-219 (1986).
Shenge et al., "Molecular Characterization of Pseudomonas Syringae pv. Tomato Isolates From Tanzania," Phytoparasitica 36(4):338-351 (2008).
Examination Report European Patent Application No. 15845670.7 (dated Jan. 28, 2019).
Office Action for U.S. Appl. No. 15/179,453 (dated Apr. 17, 2019).
Office Action for U.S. Appl. No. 14/872,347 (dated Apr. 30, 2019).
Parial Supplementary European Search Report For Corresponding EP Patent Application No. 15845670.7 (dated Feb. 22, 2018).
Choi et al., "Harpins, Multifunctional Proteins Secreted by Gram-Negative Plant-Pathogenic Bacteria," Molecular Plant-Microbe Interactions 26(10):1115-1122 (2013).
Mur et al., "The Hypersensitive Response; The centenary is Upon Us but How Much Do We Know?," Journal of Experimental Botany 59(3):501-520 (2007).
Ji et al., "Two Coiled-Coil Regions of Xanthomonas Oryzae pv. Oryzae harpin Differ in Oligomerization and Hypersensitive Response Induction," Amino Acids; the Forum for Amino Acid and Protein Research, Springer-Verlag, VA 40(2):381-392 (2010).
Osusky et al., "Transgenic Potatoes Expressing a Novel Cationic Peptide are Resistant to Late Blight and Pink Rot," Transgenic Research 13(2):181-190(2004).
Yevtushenko et al., "Comparison of Pathogen-Induced Expression and Efficacy of Two Amphibian Antimicrobial Peptides, MsrA2 and Temporin A, for Engineering Wide-Spectrum Disease Resistance in Tobacco," Plant Biotechnology Journal 5(6):720-734 (2007).
Miao et al., "HpaXm from Xanthomonas Citri Subsp. Malvacearum is a Novel Harpin With Two Heptads for Hypersensitive Response," Journal of Microbiology and Biotechnology 20(1):54-62 (2010).
Chen et al., "Identification of Specific Fragments of HpaG Xooc, a Harpin for Xanthomonas Oryzae Pv. Oryzicola, That Induce Disease Resistance and Enhance Growth in Plants," Phyto pathology 98(7):781-791 (2008).
Supplementary European Search Report For Corresponding EP Patent Application No. 15845670.7 (dated May 28, 2018).
Office Action for U.S. Appl. No. 14/872,347 (dated Jun. 26, 2018).
Office Action for U.S. Appl. No. 15/244,919 (dated Mar. 2, 2018).
Office Action for U.S. Appl. No. 15/179,453 (dated Oct. 16, 2017).
Office Action for U.S. Appl. No. 15/179,453 (dated Jun. 1, 2018).
Maget-Dana et al., "Amphiphilic Peptides as Models for Protein-Membrane Interactions: Interfacial Behaviour of Sequential Lys- and Leu-based Peptides and Their Penetration into Lipid Monolayers," Supramolecular Sci. 4:365-368 (1997).
Park et al., "Helix Stability Confers Salt Resistance upon Helical Antimicrobial Peptides," J. Biol. Chem. 279:13896-13901 (2004).
Saito et al., "Synthesis of a Peptide Emulsifier with an Amphiphilic Structure," Bioscience, Biotechnology, and Biochemistry 59:388-392 (1995).
Slechtova et al., "Insight into Trypsin Miscleavage: Comparison of Kinetic Constants of Problematic Peptide Sequences," Analytical Chemistry 87:7636-7643 (2015).
Arlat et al., "PopA1, a Protein Which Induces a Hypersensitivity-Like Response on Specific Petunia Genotypes, is Secreted Via the Hrp Pathway of Pseudomonas Solanacearum," The EMBO J. 13(3):543-553 (1994).
Gentilucci et al., "Chemical Modifications Designed to Improve Peptide Stability: Incorporation of Non-Natural Amino Acids, Pseudo-Peptide Bonds, and Cyclization," Current Pharmaceutical Design 16(28):3185-3203 (2010).
Trevino et al., "Measuring and Increasing Protein Solubility," Journal of Pharmaceutical Sciences 97 (10):4155-4166 (2008).
Niv et al., "New Lytic Peptides Based on the D, L-Amphipathic Helix Motif Preferentially Kill Tumor Cells Compared to Normal Cells," Biochemistry, American Chemical Society 42(31):9346-9354 (2003).

(56) References Cited

OTHER PUBLICATIONS

Zeitler et al., "De-Novo Design of Antimicrobial Peptides for Plant Protection," Plos One 8(8):e71687 (2013).
Van Loon et al., "Systemic Resistance Induced by Rhizosphere Bacteria," Annu. Rev. Phytopathol. 36:453-83 (1998).
Oliveira et al., "Induced Resistance During the Interaction Pathogen x Plant and the Use of Resistance Inducers," Phytochemistry Letters 15:152-158 (2016).
Office Action for U.S. Appl. No. 14/872,347 (dated Oct. 20, 2016).
Office Action for U.S. Appl. No. 14/872,347 (dated Jul. 26, 2017).
Kim et al., "Mutational Analysis of Xanthomonas Harpin HpaG Identifies a Key Functional Region That Elicits the Hypersensitive Response in Nonhost Plants," J. Bacteriol. 186(18):6239-6247 (2004).
Ji et al., "Two Coiled-Coil Regions of *Xanthomonas oryzae* pv. *Oryzae* Harpin Differ in Oligomerization and Hypersensitive Response Induction," Amino Acids 40:381-392 (2011).
Haapalainen et al., "Functional Mapping of Harpin HrpZ of Pseudomonas syringae Reveals the Sites Responsible for Protein Oligomerization, Lipid Interactions, and Plant Defence Induction," Mol. Plant Pathol. 12(2):151-66 (2011).
Lilie et al., "Polyionic and Cysteine-Containing Fusion Peptides as Versatile Protein Tags," Biol. Chem. 394(8):995-1004 (2013).
Li et al., "Complete Regression of Well-Established Tumors Using a Novel Water-Soluble Poly(L-Glutamic Acid)—Paclitaxel Conjugate," Cancer Res. 58: 2404-2409 (1998).
International Search Report and Written Opinion for PCT/US2015/053444 dated Feb. 5, 2016.
CAS RN 429026-68-6 (2002).
Wang et al., "Hpa1 is a Type III Translocator in Xanthomonas oryzae pv. Oryzae," BMC Microbiology (18):105 (2018).

* cited by examiner

SEQUENCE LISTING

<160> NUMBER OF SEQ ID NOS: 243

<210> SEQ ID NO 1
<211> LENGTH: 16
<212> TYPE: PRT
<213> ORGANISM: Artificial
<220> FEATURE:
<223> OTHER INFORMATION: Consensus Peptide
<220> FEATURE:
<221> NAME/KEY: MISC_FEATURE
<222> LOCATION: (1)..(1)
<223> OTHER INFORMATION: X at position 1 is L, I, V, or F, or is a non-
      hydrophobic amino acid, or A
<220> FEATURE:
<221> NAME/KEY: MISC_FEATURE
<222> LOCATION: (2)..(2)
<223> OTHER INFORMATION: X at position 2 is optional, any amino acid
<220> FEATURE:
<221> NAME/KEY: MISC_FEATURE
<222> LOCATION: (3)..(3)
<223> OTHER INFORMATION: X at position 3 is optional, any amino acid
<220> FEATURE:
<221> NAME/KEY: MISC_FEATURE
<222> LOCATION: (4)..(4)
<223> OTHER INFORMATION: X at position 4 is any amino acid
<220> FEATURE:
<221> NAME/KEY: MISC_FEATURE
<222> LOCATION: (5)..(5)
<223> OTHER INFORMATION: X at position 5 is L, I, V, or F, or is a non-
      hydrophobic amino acid, or A
<220> FEATURE:
<221> NAME/KEY: MISC_FEATURE
<222> LOCATION: (6)..(6)
<223> OTHER INFORMATION: X at position 6 is L, I, V, or F, or is a non-
      hydrophobic amino acid, or A
<220> FEATURE:
<221> NAME/KEY: MISC_FEATURE
<222> LOCATION: (7)..(7)
<223> OTHER INFORMATION: X at position 7 is optional, any amino acid
<220> FEATURE:
<221> NAME/KEY: MISC_FEATURE
<222> LOCATION: (8)..(8)
<223> OTHER INFORMATION: X at position 8 is optional, any amino acid
<220> FEATURE:
<221> NAME/KEY: MISC_FEATURE
<222> LOCATION: (9)..(9)
<223> OTHER INFORMATION: X at position 9 is any amino acid
<220> FEATURE:
<221> NAME/KEY: MISC_FEATURE
<222> LOCATION: (10)..(10)
<223> OTHER INFORMATION: X at position 10 is L, I, V, or F, or is a non-
      hydrophobic amino acid, or A
<220> FEATURE:
<221> NAME/KEY: MISC_FEATURE
<222> LOCATION: (11)..(11)
<223> OTHER INFORMATION: X at position 11 is L, I, V, or F, or is a non-
      hydrophobic amino acid, or A
<220> FEATURE:
<221> NAME/KEY: MISC_FEATURE
<222> LOCATION: (12)..(12)
<223> OTHER INFORMATION: X at position 12 is optional, any amino acid
<220> FEATURE:
<221> NAME/KEY: MISC_FEATURE
<222> LOCATION: (13)..(13)
<223> OTHER INFORMATION: X at position 13 is optional, any amino acid
<220> FEATURE:
<221> NAME/KEY: MISC_FEATURE
<222> LOCATION: (14)..(14)
<223> OTHER INFORMATION: X at position 14 is any amino acid
<220> FEATURE:
<221> NAME/KEY: MISC_FEATURE
<222> LOCATION: (15)..(15)
<223> OTHER INFORMATION: X at position 15 is L, I, V, or F, or is a non-
      hydrophobic amino acid, or A
<220> FEATURE:
<221> NAME/KEY: MISC_FEATURE
<222> LOCATION: (16)..(16)
<223> OTHER INFORMATION: X at position 16 is L, I, V, or F, or is a non-hydrophobic amino acid, or A

<400> SEQUENCE: 1

Xaa Xaa Xaa Xaa Xaa Xaa Xaa Xaa Xaa Xaa Xaa Xaa Xaa Xaa Xaa
1               5                   10                  15

<210> SEQ ID NO 2
<211> LENGTH: 23
<212> TYPE: PRT
<213> ORGANISM: Artificial
<220> FEATURE:
<223> OTHER INFORMATION: Modified P1/P4 consensus
<220> FEATURE:
<221> NAME/KEY: MISC_FEATURE
<222> LOCATION: (1)..(1)
<223> OTHER INFORMATION: X at position 1 is optional and can be S, N,
      D, isoD, G, A, or S
<220> FEATURE:
<221> NAME/KEY: MISC_FEATURE
<222> LOCATION: (2)..(2)
<223> OTHER INFORMATION: X at position 2 is optional and can be Q, E, g-
      glutamate, G, A, or S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (9)..(9)
<223> OTHER INFORMATION: X at position 9 is M, L, I, F, or V, or a non-
      hydrophobic amino acid
<220> FEATURE:
<221> NAME/KEY: MISC_FEATURE
<222> LOCATION: (10)..(10)
<223> OTHER INFORMATION: X at position 10 is optional and can be D or
      isoD
<220> FEATURE:
<221> NAME/KEY: MISC_FEATURE
<222> LOCATION: (11)..(11)
<223> OTHER INFORMATION: X at position 11 is Q, E, g-glutamate, G, A,
      or S
<220> FEATURE:
<221> NAME/KEY: MISC_FEATURE
<222> LOCATION: (12)..(12)
<223> OTHER INFORMATION: X at position 12 is M, L, I, or F, or a non-
      hydrophobic amino acid
<220> FEATURE:
<221> NAME/KEY: MISC_FEATURE
<222> LOCATION: (13)..(13)
<223> OTHER INFORMATION: X at position 13 is M, L, or I, or a non-
      hydrophobic amino acid
<220> FEATURE:
<221> NAME/KEY: MISC_FEATURE
<222> LOCATION: (14)..(14)
<223> OTHER INFORMATION: X at position 14 is optional and can be any
      hydrophilic amino acid, preferably S, T, D, isoD, K, or Q, and
      optionally A or C
<220> FEATURE:
<221> NAME/KEY: MISC_FEATURE
<222> LOCATION: (15)..(15)
<223> OTHER INFORMATION: X at position 15 is Q, E, g-glutamate, G, A,
      S, K, or I
<220> FEATURE:
<221> NAME/KEY: MISC_FEATURE
<222> LOCATION: (16)..(16)
<223> OTHER INFORMATION: X at position 16 is M, L, I, V, or F, or a non-
      hydrophobic amino acid
<220> FEATURE:
<221> NAME/KEY: MISC_FEATURE
<222> LOCATION: (17)..(17)
<223> OTHER INFORMATION: X at position 17 is M, L, I, A, or V, or a non-
      hydrophobic amino acid
<220> FEATURE:
<221> NAME/KEY: MISC_FEATURE
<222> LOCATION: (18)..(18)
<223> OTHER INFORMATION: X at position 18 is Q, E, g-glutamate, G, A,

```
          S, M, T, or K
<220> FEATURE:
<221> NAME/KEY: MISC_FEATURE
<222> LOCATION: (19)..(19)
<223> OTHER INFORMATION: X at position 19 is A, D, isoD, S, V, T, K, R,
      E, H, or G
<220> FEATURE:
<221> NAME/KEY: MISC_FEATURE
<222> LOCATION: (20)..(20)
<223> OTHER INFORMATION: X at position 20 is M, L, or I
<220> FEATURE:
<221> NAME/KEY: MISC_FEATURE
<222> LOCATION: (21)..(21)
<223> OTHER INFORMATION: X at position 21 is M, L, I, V, S, or F, or a
      non-hydrophobic amino acid other than serine
<220> FEATURE:
<221> NAME/KEY: MISC_FEATURE
<222> LOCATION: (22)..(22)
<223> OTHER INFORMATION: X at position 22 is Q, E, g-glutamate, G, A,
      or S
<220> FEATURE:
<221> NAME/KEY: MISC_FEATURE
<222> LOCATION: (23)..(23)
<223> OTHER INFORMATION: X at position 23 is P, Q, E, g-glutamate, G, A
      , or S

<400> SEQUENCE: 2

Xaa Xaa Gly Ile Ser Glu Lys Xaa Xaa Xaa Xaa Xaa Xaa Xaa Xaa
1               5                   10                  15

Xaa Xaa Xaa Xaa Xaa Xaa Xaa
            20

<210> SEQ ID NO 3
<211> LENGTH: 23
<212> TYPE: PRT
<213> ORGANISM: Artificial
<220> FEATURE:
<223> OTHER INFORMATION: Modified P4 consensus
<220> FEATURE:
<221> NAME/KEY: MISC_FEATURE
<222> LOCATION: (2)..(2)
<223> OTHER INFORMATION: X at position 2 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (9)..(9)
<223> OTHER INFORMATION: X at position 9 is M, S, L, A, I, V, or F, or
      a non-hydrophobic amino acid other than serine
<220> FEATURE:
<221> NAME/KEY: MISC_FEATURE
<222> LOCATION: (11)..(11)
<223> OTHER INFORMATION: X at position 11 is Q, E, g-glutamate, G, A,
      or S
<220> FEATURE:
<221> NAME/KEY: MISC_FEATURE
<222> LOCATION: (12)..(12)
<223> OTHER INFORMATION: X at position 12 is L, I, or F, or a non-
      hydrophobic amino acid
<220> FEATURE:
<221> NAME/KEY: MISC_FEATURE
<222> LOCATION: (13)..(13)
<223> OTHER INFORMATION: X at position 13 is L, A, I, V, or F, or a non-
      hydrophobic amino acid
<220> FEATURE:
<221> NAME/KEY: MISC_FEATURE
<222> LOCATION: (14)..(14)
<223> OTHER INFORMATION: X at position 14 is any hydrophilic amino acid
<220> FEATURE:
<221> NAME/KEY: MISC_FEATURE
<222> LOCATION: (15)..(15)
<223> OTHER INFORMATION: X at position 15 is Q, E, g-glutamate, G, A, S
```

-continued

```
, K, or I
<220> FEATURE:
<221> NAME/KEY: MISC_FEATURE
<222> LOCATION: (16)..(16)
<223> OTHER INFORMATION: X at position 16 is L, A, I, V, M, or F, or a
      non-hydrophobic amino acid
<220> FEATURE:
<221> NAME/KEY: MISC_FEATURE
<222> LOCATION: (17)..(17)
<223> OTHER INFORMATION: X at position 17 is M, I, S, or F, or a non-
      hydrophobic amino acid other than serine
<220> FEATURE:
<221> NAME/KEY: MISC_FEATURE
<222> LOCATION: (18)..(18)
<223> OTHER INFORMATION: X at position 18 is Q, E, g-glutamate, G, A,
      or S
<220> FEATURE:
<221> NAME/KEY: MISC_FEATURE
<222> LOCATION: (20)..(20)
<223> OTHER INFORMATION: X at position 20 is M, L, I, V, or F, or a non-
      hydrophobic amino acid
<220> FEATURE:
<221> NAME/KEY: MISC_FEATURE
<222> LOCATION: (21)..(21)
<223> OTHER INFORMATION: X at position 21 is M, L or F, or is a non-
      hydrophobic amino acid
<220> FEATURE:
<221> NAME/KEY: MISC_FEATURE
<222> LOCATION: (22)..(22)
<223> OTHER INFORMATION: X at position 22 is Q, E, g-glutamate, G, A,
      or S

<400> SEQUENCE: 3

Ser Xaa Gly Ile Ser Glu Lys Xaa Xaa Asp Xaa Xaa Xaa Xaa Xaa Xaa
1               5                   10                  15

Xaa Xaa Ala Xaa Xaa Xaa Pro
            20

<210> SEQ ID NO 4
<211> LENGTH: 23
<212> TYPE: PRT
<213> ORGANISM: Artificial
<220> FEATURE:
<223> OTHER INFORMATION: Modified P1 consensus
<220> FEATURE:
<221> NAME/KEY: MISC_FEATURE
<222> LOCATION: (1)..(1)
<223> OTHER INFORMATION: X at position 1 is N, D, isoD, G, A, or S
<220> FEATURE:
<221> NAME/KEY: MISC_FEATURE
<222> LOCATION: (2)..(2)
<223> OTHER INFORMATION: X at position 2 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is Q, E, g-glutamate, G, A, or
      S
<220> FEATURE:
<221> NAME/KEY: MISC_FEATURE
<222> LOCATION: (9)..(9)
<223> OTHER INFORMATION: X at position 9 is L, V, I, or F, or a non-
      hydrophobic amino acid, or A
<220> FEATURE:
<221> NAME/KEY: MISC_FEATURE
<222> LOCATION: (11)..(11)
<223> OTHER INFORMATION: X at position 11 is Q, E, g-glutamate, G, A,
      or S
<220> FEATURE:
<221> NAME/KEY: MISC_FEATURE
<222> LOCATION: (12)..(12)
<223> OTHER INFORMATION: X at position 12 is L, V, I, or F, or a non-
      hydrophobic amino acid, or A
<220> FEATURE:
<221> NAME/KEY: MISC_FEATURE
<222> LOCATION: (13)..(13)
```

```
<223> OTHER INFORMATION: X at position 13 is L, V, I, or F, or a non-
      hydrophobic amino acid, or A
<220> FEATURE:
<221> NAME/KEY: MISC_FEATURE
<222> LOCATION: (15)..(15)
<223> OTHER INFORMATION: X at position 15 is Q, E, g-glutamate, G, A,
      or S
<220> FEATURE:
<221> NAME/KEY: MISC_FEATURE
<222> LOCATION: (16)..(16)
<223> OTHER INFORMATION: X at position 16 is L, V, I, or F, or a non-
      hydrophobic amino acid, or A
<220> FEATURE:
<221> NAME/KEY: MISC_FEATURE
<222> LOCATION: (17)..(17)
<223> OTHER INFORMATION: X at position 17 is L, V, I, or F, or a non-
      hydrophobic amino acid, or A
<220> FEATURE:
<221> NAME/KEY: MISC_FEATURE
<222> LOCATION: (18)..(18)
<223> OTHER INFORMATION: X at position 18 is M, T, K, E, g-glutamate, G
      , A, or S
<220> FEATURE:
<221> NAME/KEY: MISC_FEATURE
<222> LOCATION: (20)..(20)
<223> OTHER INFORMATION: X at position 20 is L, V, I, or F, or a non-
      hydrophobic amino acid, or A
<220> FEATURE:
<221> NAME/KEY: MISC_FEATURE
<222> LOCATION: (21)..(21)
<223> OTHER INFORMATION: X at position 21 is L, V, I, or F, or a non-
      hydrophobic amino acid, or A
<220> FEATURE:
<221> NAME/KEY: MISC_FEATURE
<222> LOCATION: (22)..(22)
<223> OTHER INFORMATION: X at position 22 is Q, E, g-glutamate, G, A,
      or S
<220> FEATURE:
<221> NAME/KEY: MISC_FEATURE
<222> LOCATION: (23)..(23)
<223> OTHER INFORMATION: X at position 23 is Q, E, g-glutamate, G, A,
      or S

<400> SEQUENCE: 4

Xaa Xaa Gly Ile Ser Glu Lys Xaa Xaa Asp Xaa Xaa Xaa Thr Xaa Xaa
1               5                   10                  15

Xaa Xaa Ala Xaa Xaa Xaa Xaa
            20

<210> SEQ ID NO 5
<211> LENGTH: 22
<212> TYPE: PRT
<213> ORGANISM: Artificial
<220> FEATURE:
<223> OTHER INFORMATION: Modified P15b/P20 consensus
<220> FEATURE:
<221> NAME/KEY: MISC_FEATURE
<222> LOCATION: (3)..(3)
<223> OTHER INFORMATION: X at position 3 is N, D, or isoD
<220> FEATURE:
<221> NAME/KEY: MISC_FEATURE
<222> LOCATION: (6)..(6)
<223> OTHER INFORMATION: X at position 6 is Q, E, g-glutamate, G, A, or
      S
<220> FEATURE:
<221> NAME/KEY: MISC_FEATURE
<222> LOCATION: (8)..(8)
<223> OTHER INFORMATION: X at position 8 is N, D, or isoD
<220> FEATURE:
<221> NAME/KEY: MISC_FEATURE
<222> LOCATION: (9)..(9)
<223> OTHER INFORMATION: X at position 9 is L, V, I, or F, or a non-
      hydrophobic amino acid, or A
<220> FEATURE:
<221> NAME/KEY: MISC_FEATURE
<222> LOCATION: (12)..(12)
```

```
<223> OTHER INFORMATION: X at position 12 is L, V, I, or F, or a non-
      hydrophobic amino acid, or A
<220> FEATURE:
<221> NAME/KEY: MISC_FEATURE
<222> LOCATION: (13)..(13)
<223> OTHER INFORMATION: X at position 13 is L, V, I, or F, or a non-
      hydrophobic amino acid, or A
<220> FEATURE:
<221> NAME/KEY: MISC_FEATURE
<222> LOCATION: (15)..(15)
<223> OTHER INFORMATION: X at position 15 is optional and can be any
      amino acid
<220> FEATURE:
<221> NAME/KEY: MISC_FEATURE
<222> LOCATION: (16)..(16)
<223> OTHER INFORMATION: X at position 16 is L, V, I, or F, or a non-
      hydrophobic amino acid, or A
<220> FEATURE:
<221> NAME/KEY: MISC_FEATURE
<222> LOCATION: (17)..(17)
<223> OTHER INFORMATION: X at position 17 is L, V, I, or F, or a non-
      hydrophobic amino acid, or A
<220> FEATURE:
<221> NAME/KEY: MISC_FEATURE
<222> LOCATION: (18)..(18)
<223> OTHER INFORMATION: X at position 18 is M, E, g-glutamate, G, A, S
      , T, or K
<220> FEATURE:
<221> NAME/KEY: MISC_FEATURE
<222> LOCATION: (20)..(20)
<223> OTHER INFORMATION: X at position 20 is L, V, I, or F, or a non-
      hydrophobic amino acid, or A
<220> FEATURE:
<221> NAME/KEY: MISC_FEATURE
<222> LOCATION: (21)..(21)
<223> OTHER INFORMATION: X at position 21 is L, V, I, or F, or a non-
      hydrophobic amino acid, or A
<220> FEATURE:
<221> NAME/KEY: MISC_FEATURE
<222> LOCATION: (22)..(22)
<223> OTHER INFORMATION: X at position 22 is optional and can be Q, E,
      g-glutamate, G, A, or S

<400> SEQUENCE: 5

Lys Pro Xaa Asp Ser Xaa Ser Xaa Xaa Ala Lys Xaa Xaa Ser Xaa Xaa
1               5                   10                  15

Xaa Xaa Ser Xaa Xaa Xaa
            20

<210> SEQ ID NO 6
<211> LENGTH: 14
<212> TYPE: PRT
<213> ORGANISM: Artificial
<220> FEATURE:
<223> OTHER INFORMATION: Modified P15/P20 min consensus
<220> FEATURE:
<221> NAME/KEY: MISC_FEATURE
<222> LOCATION: (1)..(1)
<223> OTHER INFORMATION: X at position 1 is L, V, I, or F, or a non-
      hydrophobic amino acid, or A
<220> FEATURE:
<221> NAME/KEY: MISC_FEATURE
<222> LOCATION: (4)..(4)
<223> OTHER INFORMATION: X at position 4 is L, V, I, or F, or a non-
      hydrophobic amino acid, or A
<220> FEATURE:
<221> NAME/KEY: MISC_FEATURE
<222> LOCATION: (5)..(5)
<223> OTHER INFORMATION: X at position 5 is L, V, I, or F, or a non-
      hydrophobic amino acid, or A
<220> FEATURE:
<221> NAME/KEY: MISC_FEATURE
<222> LOCATION: (7)..(7)
<223> OTHER INFORMATION: X at position 7 is optional and can be any
      amino acid
<220> FEATURE:
```

```
<221> NAME/KEY: MISC_FEATURE
<222> LOCATION: (8)..(8)
<223> OTHER INFORMATION: X at position 8 is L, V, I, or F, or a non-
      hydrophobic amino acid, or A
<220> FEATURE:
<221> NAME/KEY: MISC_FEATURE
<222> LOCATION: (9)..(9)
<223> OTHER INFORMATION: X at position 9 is L, V, I, or F, or a non-
      hydrophobic amino acid, or A
<220> FEATURE:
<221> NAME/KEY: MISC_FEATURE
<222> LOCATION: (10)..(10)
<223> OTHER INFORMATION: X at position 10 is M, E, g-glutamate, G, A, S
      , T, or K
<220> FEATURE:
<221> NAME/KEY: MISC_FEATURE
<222> LOCATION: (12)..(12)
<223> OTHER INFORMATION: X at position 12 is L, V, I, or F, or a non-
      hydrophobic amino acid, or A
<220> FEATURE:
<221> NAME/KEY: MISC_FEATURE
<222> LOCATION: (13)..(13)
<223> OTHER INFORMATION: X at position 13 is L, V, I, or F, or a non-
      hydrophobic amino acid, or A
<220> FEATURE:
<221> NAME/KEY: MISC_FEATURE
<222> LOCATION: (14)..(14)
<223> OTHER INFORMATION: X at position 14 is optional and can be Q, E,
      g-glutamate, G, A, or S

<400> SEQUENCE: 6

Xaa Ala Lys Xaa Xaa Ser Xaa Xaa Xaa Xaa Ser Xaa Xaa Xaa
1               5                   10

<210> SEQ ID NO 7
<211> LENGTH: 20
<212> TYPE: PRT
<213> ORGANISM: Artificial
<220> FEATURE:
<223> OTHER INFORMATION: Modified P6/6a consensus
<220> FEATURE:
<221> NAME/KEY: MISC_FEATURE
<222> LOCATION: (4)..(4)
<223> OTHER INFORMATION: X at position 4 is L, V, I, M or F, or a non-
      hydrophobic amino acid, or A
<220> FEATURE:
<221> NAME/KEY: MISC_FEATURE
<222> LOCATION: (6)..(6)
<223> OTHER INFORMATION: X at position 6 is Q, E, g-glutamate, G, A, or
      S
<220> FEATURE:
<221> NAME/KEY: MISC_FEATURE
<222> LOCATION: (7)..(7)
<223> OTHER INFORMATION: X at position 7 is L, V, I, M or F, or a non-
      hydrophobic amino acid, or A
<220> FEATURE:
<221> NAME/KEY: MISC_FEATURE
<222> LOCATION: (8)..(8)
<223> OTHER INFORMATION: X at position 8 is L, V, I, M or F, or a non-
      hydrophobic amino acid, or A
<220> FEATURE:
<221> NAME/KEY: MISC_FEATURE
<222> LOCATION: (9)..(9)
<223> OTHER INFORMATION: X at position 9 is M, E, g-glutamate, G, A, S,
      T, or K
<220> FEATURE:
<221> NAME/KEY: MISC_FEATURE
<222> LOCATION: (10)..(10)
<223> OTHER INFORMATION: X at position 10 is H or N
<220> FEATURE:
<221> NAME/KEY: MISC_FEATURE
<222> LOCATION: (11)..(11)
<223> OTHER INFORMATION: X at position 11 is L, V, I, M or F, or a non-
      hydrophobic amino acid, or A
<220> FEATURE:
<221> NAME/KEY: MISC_FEATURE
<222> LOCATION: (12)..(12)
```

```
<223> OTHER INFORMATION: X at position 12 is L, V, I, M or F, or a non-
      hydrophobic amino acid, or A
<220> FEATURE:
<221> NAME/KEY: MISC_FEATURE
<222> LOCATION: (14)..(14)
<223> OTHER INFORMATION: X at position 14 is E, g-glutamate, D, or isoD
<220> FEATURE:
<221> NAME/KEY: MISC_FEATURE
<222> LOCATION: (15)..(15)
<223> OTHER INFORMATION: X at position 15 is L, V, I, M or F, or a non-
      hydrophobic amino acid, or A
<220> FEATURE:
<221> NAME/KEY: MISC_FEATURE
<222> LOCATION: (16)..(16)
<223> OTHER INFORMATION: X at position 16 is L, V, I, M or F, or a non-
      hydrophobic amino acid, or A
<220> FEATURE:
<221> NAME/KEY: MISC_FEATURE
<222> LOCATION: (17)..(17)
<223> OTHER INFORMATION: X at position 17 is Q, E, g-glutamate, G, A,
      or S
<220> FEATURE:
<221> NAME/KEY: MISC_FEATURE
<222> LOCATION: (19)..(19)
<223> OTHER INFORMATION: X at position 19 is Q, E, g-glutamate, G, A,
      or S

<400> SEQUENCE: 7

Pro Ser Pro Xaa Thr Xaa Xaa Xaa Xaa Xaa Xaa Xaa Gly Xaa Xaa Xaa
1               5                   10                  15

Xaa Ala Xaa Asn
            20

<210> SEQ ID NO 8
<211> LENGTH: 19
<212> TYPE: PRT
<213> ORGANISM: Artificial
<220> FEATURE:
<223> OTHER INFORMATION: Modified P14d consensus
<220> FEATURE:
<221> NAME/KEY: MISC_FEATURE
<222> LOCATION: (1)..(1)
<223> OTHER INFORMATION: X at position 1 can be: Q, N, D, E, g-glutamate
      , isoD, or S
<220> FEATURE:
<221> NAME/KEY: MISC_FEATURE
<222> LOCATION: (2)..(2)
<223> OTHER INFORMATION: X at position 2 can be: D, E, g-glutamate, isoD
<220> FEATURE:
<221> NAME/KEY: MISC_FEATURE
<222> LOCATION: (3)..(3)
<223> OTHER INFORMATION: X at position 3 can be: P, D, E, isoD, or g-
      glutamate
<220> FEATURE:
<221> NAME/KEY: MISC_FEATURE
<222> LOCATION: (4)..(4)
<223> OTHER INFORMATION: X at position 4 can be M, A, S, D, E, isoD, or
      g-glutamate
<220> FEATURE:
<221> NAME/KEY: MISC_FEATURE
<222> LOCATION: (5)..(5)
<223> OTHER INFORMATION: X at position 5 can be Q, E, or g-glutamate
<220> FEATURE:
<221> NAME/KEY: MISC_FEATURE
<222> LOCATION: (6)..(6)
<223> OTHER INFORMATION: X at position 6 can be A, E, or g-glutamate
<220> FEATURE:
<221> NAME/KEY: MISC_FEATURE
<222> LOCATION: (7)..(7)
<223> OTHER INFORMATION: X at position 7 is L, V, I, or F, or a non-
      hydrophobic amino acid, or A
<220> FEATURE:
<221> NAME/KEY: MISC_FEATURE
<222> LOCATION: (8)..(8)
<223> OTHER INFORMATION: X at position 8 can be M, L, E, Q, D, N, G, A,
      S, isoD, or g-glutamate
```

```
<220> FEATURE:
<221> NAME/KEY: MISC_FEATURE
<222> LOCATION: (9)..(9)
<223> OTHER INFORMATION: X at position 9 can be Q, N, E, D, G, A, S,
      isoD, or g-glutamate
<220> FEATURE:
<221> NAME/KEY: MISC_FEATURE
<222> LOCATION: (10)..(10)
<223> OTHER INFORMATION: X at position 10 is L, V, I, or F, or a non-
      hydrophobic amino acid, or A
<220> FEATURE:
<221> NAME/KEY: MISC_FEATURE
<222> LOCATION: (11)..(11)
<223> OTHER INFORMATION: X at position 11 is L, V, I, or F, or a non-
      hydrophobic amino acid, or A
<220> FEATURE:
<221> NAME/KEY: MISC_FEATURE
<222> LOCATION: (12)..(12)
<223> OTHER INFORMATION: X at position 12 can be Q, N, E, D, G, A, S,
      isoD, or g-glutamate
<220> FEATURE:
<221> NAME/KEY: MISC_FEATURE
<222> LOCATION: (13)..(13)
<223> OTHER INFORMATION: X at position 13 can be Q, N, E, D, G, A, S,
      isoD, or g-glutamate
<220> FEATURE:
<221> NAME/KEY: MISC_FEATURE
<222> LOCATION: (14)..(14)
<223> OTHER INFORMATION: X at position 14 is L, V, I, or F, or a non-
      hydrophobic amino acid, or A
<220> FEATURE:
<221> NAME/KEY: MISC_FEATURE
<222> LOCATION: (15)..(15)
<223> OTHER INFORMATION: X at position 15 is L, V, I, or F, or a non-
      hydrophobic amino acid, or A
<220> FEATURE:
<221> NAME/KEY: MISC_FEATURE
<222> LOCATION: (16)..(16)
<223> OTHER INFORMATION: X at position 16 can be K, Q, N, E, D, R, G, A
      , or S
<220> FEATURE:
<221> NAME/KEY: MISC_FEATURE
<222> LOCATION: (17)..(17)
<223> OTHER INFORMATION: X at position 17 is L, V, I, or F, or a non-
      hydrophobic amino acid, or A
<220> FEATURE:
<221> NAME/KEY: MISC_FEATURE
<222> LOCATION: (18)..(18)
<223> OTHER INFORMATION: X at position 18 is L, V, I, or F, or a non-
      hydrophobic amino acid, or A

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Lys

<210> SEQ ID NO 9
<211> LENGTH: 13
<212> TYPE: PRT
<213> ORGANISM: Artificial
<220> FEATURE:
<223> OTHER INFORMATION: Modified P14d min consensus
<220> FEATURE:
<221> NAME/KEY: MISC_FEATURE
<222> LOCATION: (1)..(1)
<223> OTHER INFORMATION: X at position 1 is L, V, I, or F, or a non-
      hydrophobic amino acid, or A
<220> FEATURE:
<221> NAME/KEY: MISC_FEATURE
<222> LOCATION: (2)..(2)
<223> OTHER INFORMATION: X at position 2 can be M, L, E, Q, D, N, G, A,
      S, isoD, or g-glutamate
<220> FEATURE:
<221> NAME/KEY: MISC_FEATURE
<222> LOCATION: (3)..(3)
<223> OTHER INFORMATION: X at position 3 can be Q, N, E, D, G, A, S,
```

```
             isoD, or g-glutamate
<220> FEATURE:
<221> NAME/KEY: MISC_FEATURE
<222> LOCATION: (4)..(4)
<223> OTHER INFORMATION: X at position 4 is L, V, I, or F, or a non-
      hydrophobic amino acid, or A
<220> FEATURE:
<221> NAME/KEY: MISC_FEATURE
<222> LOCATION: (5)..(5)
<223> OTHER INFORMATION: X at position 5 is L, V, I, or F, or a non-
      hydrophobic amino acid, or A
<220> FEATURE:
<221> NAME/KEY: MISC_FEATURE
<222> LOCATION: (6)..(6)
<223> OTHER INFORMATION: X at position 6 can be Q, N, E, D, G, A, S,
      isoD, or g-glutamate
<220> FEATURE:
<221> NAME/KEY: MISC_FEATURE
<222> LOCATION: (7)..(7)
<223> OTHER INFORMATION: X at position 7 can be Q, N, E, D, G, A, S,
      isoD, or g-glutamate
<220> FEATURE:
<221> NAME/KEY: MISC_FEATURE
<222> LOCATION: (8)..(8)
<223> OTHER INFORMATION: X at position 8 is L, V, I, or F, or a non-
      hydrophobic amino acid, or A
<220> FEATURE:
<221> NAME/KEY: MISC_FEATURE
<222> LOCATION: (9)..(9)
<223> OTHER INFORMATION: X at position 9 is L, V, I, or F, or a non-
      hydrophobic amino acid, or A
<220> FEATURE:
<221> NAME/KEY: MISC_FEATURE
<222> LOCATION: (10)..(10)
<223> OTHER INFORMATION: X at position 10 can be K, Q, N, E, D, R, G, A
      , or S
<220> FEATURE:
<221> NAME/KEY: MISC_FEATURE
<222> LOCATION: (11)..(11)
<223> OTHER INFORMATION: X at position 11 is L, V, I, or F, or a non-
      hydrophobic amino acid, or A
<220> FEATURE:
<221> NAME/KEY: MISC_FEATURE
<222> LOCATION: (12)..(12)
<223> OTHER INFORMATION: X at position 12 L, V, I, or F, or a non-
      hydrophobic amino acid, or A

<400> SEQUENCE: 9

Xaa Xaa Xaa Xaa Xaa Xaa Xaa Xaa Xaa Xaa Xaa Xaa Lys
1               5                   10

<210> SEQ ID NO 10
<211> LENGTH: 12
<212> TYPE: PRT
<213> ORGANISM: Artificial
<220> FEATURE:
<223> OTHER INFORMATION: Modified P25 consensus
<220> FEATURE:
<221> NAME/KEY: MISC_FEATURE
<222> LOCATION: (1)..(1)
<223> OTHER INFORMATION: X at position 1 is L, V, I, F, or M, or a non-
      hydrophobic amino acid, or A
<220> FEATURE:
<221> NAME/KEY: MISC_FEATURE
<222> LOCATION: (2)..(2)
<223> OTHER INFORMATION: X at position 2 can be Q, N, E, g-glutamate, D
      , isoD, T, S, A, or G
<220> FEATURE:
<221> NAME/KEY: MISC_FEATURE
<222> LOCATION: (3)..(3)
<223> OTHER INFORMATION: X at position 3 can be K, Q, N, E, g-glutamate
      , D, isoD, T, S, A, or G
<220> FEATURE:
<221> NAME/KEY: MISC_FEATURE
<222> LOCATION: (4)..(4)
<223> OTHER INFORMATION: X at position 4 is L, V, I, F, or M, or a non-
      hydrophobic amino acid, or A
```

```
<220> FEATURE:
<221> NAME/KEY: MISC_FEATURE
<222> LOCATION: (5)..(5)
<223> OTHER INFORMATION: X at position 5 is L, V, I, F, or M, or a non-
      hydrophobic amino acid, or A
<220> FEATURE:
<221> NAME/KEY: MISC_FEATURE
<222> LOCATION: (6)..(6)
<223> OTHER INFORMATION: X at position 6 can be K, Q, N, E, g-glutamate
      , D, isoD, T, S, A, or G
<220> FEATURE:
<221> NAME/KEY: MISC_FEATURE
<222> LOCATION: (7)..(7)
<223> OTHER INFORMATION: X at position 7 is L, V, I, F, or M, or a non-
      hydrophobic amino acid, or A
<220> FEATURE:
<221> NAME/KEY: MISC_FEATURE
<222> LOCATION: (8)..(8)
<223> OTHER INFORMATION: X at position 8 is L, V, I, F, or M, or a non-
      hydrophobic amino acid, or A
<220> FEATURE:
<221> NAME/KEY: MISC_FEATURE
<222> LOCATION: (9)..(9)
<223> OTHER INFORMATION: X at position 9 can be E, g-glutamate, D, isoD
      , Q, N, T, S, A, or G
<220> FEATURE:
<221> NAME/KEY: MISC_FEATURE
<222> LOCATION: (10)..(10)
<223> OTHER INFORMATION: X at position 10 can be A, G, S, T, E, g-
      glutamate, D, isoD, Q, or N
<220> FEATURE:
<221> NAME/KEY: MISC_FEATURE
<222> LOCATION: (11)..(11)
<223> OTHER INFORMATION: X at position 11 is L, V, I, F, or M, or a non-
      hydrophobic amino acid, or A
<220> FEATURE:
<221> NAME/KEY: MISC_FEATURE
<222> LOCATION: (12)..(12)
<223> OTHER INFORMATION: X at position 12 is L, V, I, F, or M, or a non-
      hydrophobic amino acid, or A

<400> SEQUENCE: 10

Xaa Xaa Xaa Xaa Xaa Xaa Xaa Xaa Xaa Xaa Xaa Xaa
1               5                   10

<210> SEQ ID NO 11
<211> LENGTH: 16
<212> TYPE: PRT
<213> ORGANISM: Artificial
<220> FEATURE:
<223> OTHER INFORMATION: Modified P25 consensus
<220> FEATURE:
<221> NAME/KEY: MISC_FEATURE
<222> LOCATION: (1)..(1)
<223> OTHER INFORMATION: X at position 1 is L, V, I, F, or M, or a non-
      hydrophobic amino acid, or A
<220> FEATURE:
<221> NAME/KEY: MISC_FEATURE
<222> LOCATION: (2)..(2)
<223> OTHER INFORMATION: X at position 2 can be T, S, A, G, D, isoD, E,
      g-glutamate, Q, or N
<220> FEATURE:
<221> NAME/KEY: MISC_FEATURE
<222> LOCATION: (3)..(3)
<223> OTHER INFORMATION: X at position 3 can be G, T, S, A, D, isoD, E,
      g-glutamate, Q, or N
<220> FEATURE:
<221> NAME/KEY: MISC_FEATURE
<222> LOCATION: (4)..(4)
<223> OTHER INFORMATION: X at position 4 is L, V, I, F, or M, or a non-
      hydrophobic amino acid, or A
<220> FEATURE:
<221> NAME/KEY: MISC_FEATURE
<222> LOCATION: (5)..(5)
<223> OTHER INFORMATION: X at position 5 is L, V, I, F, or M, or a non-
      hydrophobic amino acid, or A
<220> FEATURE:
```

```
<221> NAME/KEY: MISC_FEATURE
<222> LOCATION: (6)..(6)
<223> OTHER INFORMATION: X at position 6 can be Q, N, E, g-glutamate, D
      , isoD, T, S, A, or G
<220> FEATURE:
<221> NAME/KEY: MISC_FEATURE
<222> LOCATION: (7)..(7)
<223> OTHER INFORMATION: X at position 7 can be K, Q, N, E, g-glutamate
      , D, isoD, T, S, A, or G
<220> FEATURE:
<221> NAME/KEY: MISC_FEATURE
<222> LOCATION: (8)..(8)
<223> OTHER INFORMATION: X at position 8 is L, V, I, F, or M, or a non-
      hydrophobic amino acid, or A
<220> FEATURE:
<221> NAME/KEY: MISC_FEATURE
<222> LOCATION: (9)..(9)
<223> OTHER INFORMATION: X at position 9 is L, V, I, F, or M, or a non-
      hydrophobic amino acid, or A
<220> FEATURE:
<221> NAME/KEY: MISC_FEATURE
<222> LOCATION: (10)..(10)
<223> OTHER INFORMATION: X at position 10 can be K, Q, N, E,
      g-glutamate, D, isoD, T, S, A, or G
<220> FEATURE:
<221> NAME/KEY: MISC_FEATURE
<222> LOCATION: (11)..(11)
<223> OTHER INFORMATION: X at position 11 is L, V, I, F, or M, or a non-
      hydrophobic amino acid, or A
<220> FEATURE:
<221> NAME/KEY: MISC_FEATURE
<222> LOCATION: (12)..(12)
<223> OTHER INFORMATION: X at position 12 is L, V, I, F, or M, or a non-
      hydrophobic amino acid, or A
<220> FEATURE:
<221> NAME/KEY: MISC_FEATURE
<222> LOCATION: (13)..(13)
<223> OTHER INFORMATION: X at position 13 can be E, g-glutamate, D,
      isoD, Q, N, T, S, A, or G
<220> FEATURE:
<221> NAME/KEY: MISC_FEATURE
<222> LOCATION: (14)..(14)
<223> OTHER INFORMATION: X at position 14 can be A, G, S, T, E,
      g-glutamate, D, isoD, Q, or N
<220> FEATURE:
<221> NAME/KEY: MISC_FEATURE
<222> LOCATION: (15)..(15)
<223> OTHER INFORMATION: X at position 15 is L, V, I, F, or M, or a non-
      hydrophobic amino acid, or A
<220> FEATURE:
<221> NAME/KEY: MISC_FEATURE
<222> LOCATION: (16)..(16)
<223> OTHER INFORMATION: X at position 16 is optional and is L, V, I,
      or F

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

<210> SEQ ID NO 12
<211> LENGTH: 27
<212> TYPE: PRT
<213> ORGANISM: Artificial
<220> FEATURE:
<223> OTHER INFORMATION: Modified P17/18
<220> FEATURE:
<221> NAME/KEY: MISC_FEATURE
<222> LOCATION: (1)..(1)
<223> OTHER INFORMATION: X at position 1 can be any amino acid, but
      preferably Q, S, E, g-glutamate, A, T, G, D, isoD, N, K, or R
<220> FEATURE:
<221> NAME/KEY: MISC_FEATURE
<222> LOCATION: (2)..(2)
<223> OTHER INFORMATION: X at position 2 can be any amino acid, but
      preferably Q, S, E, g-glutamate, A, T, G, D, isoD, N, K, or R
<220> FEATURE:
<221> NAME/KEY: MISC_FEATURE
```

```
<222> LOCATION: (3)..(3)
<223> OTHER INFORMATION: X at position 3 can be any amino acid, but
      preferably P, Q, S, E, g-glutamate, A, T, G, D, isoD, N, K, or R
<220> FEATURE:
<221> NAME/KEY: MISC_FEATURE
<222> LOCATION: (4)..(4)
<223> OTHER INFORMATION: X at position 4 can be any amino acid, but
      preferably I, Q, S, E, g-glutamate, A, T, G, D, N, isoD, K, or R
<220> FEATURE:
<221> NAME/KEY: MISC_FEATURE
<222> LOCATION: (5)..(5)
<223> OTHER INFORMATION: X at position 5 can be any amino acid, but
      preferably D, isoD, S, E, g-glutamate, A, T, G, N, Q, K, or R
<220> FEATURE:
<221> NAME/KEY: MISC_FEATURE
<222> LOCATION: (6)..(6)
<223> OTHER INFORMATION: X at position 6 can be any amino acid, but
      preferably R, Q, S, E, g-glutamate, A, T, G, D, isoD, N, or K
<220> FEATURE:
<221> NAME/KEY: MISC_FEATURE
<222> LOCATION: (7)..(7)
<223> OTHER INFORMATION: X of position 7 can be any amino acid, but
      preferably Q, S, E, g-glutamate, A, T, G, D, isoD, N, K, or R
<220> FEATURE:
<221> NAME/KEY: MISC_FEATURE
<222> LOCATION: (8)..(8)
<223> OTHER INFORMATION: X at position 8 can be any amino acid, but
      preferably T, Q, S, E, g-glutamate, A, G, D, isoD, N, K, or R
<220> FEATURE:
<221> NAME/KEY: MISC_FEATURE
<222> LOCATION: (9)..(9)
<223> OTHER INFORMATION: X at position 9 can be any amino acid, but
      preferably I, Q, S, E, g-glutamate, A, T, G, D, isoD, N, K, or R
<220> FEATURE:
<221> NAME/KEY: MISC_FEATURE
<222> LOCATION: (10)..(10)
<223> OTHER INFORMATION: X at position 10 can be any amino acid, but
      preferably E, g-glutamate, Q, S, A, T, G, D, isoD, N, K, or R
<220> FEATURE:
<221> NAME/KEY: MISC_FEATURE
<222> LOCATION: (11)..(11)
<223> OTHER INFORMATION: X at position 11 can be any amino acid, but
      preferably Q, S, E, g-glutamate, A, T, G, D, isoD, N, K, or R
<220> FEATURE:
<221> NAME/KEY: MISC_FEATURE
<222> LOCATION: (12)..(12)
<223> OTHER INFORMATION: X at position 12 is L, V, I, F, or M, or a non-
      hydrophobic amino acid, or A
<220> FEATURE:
<221> NAME/KEY: MISC_FEATURE
<222> LOCATION: (13)..(13)
<223> OTHER INFORMATION: X at position 13 can be any amino acid, but
      preferably A, S, T, G, D, isoD, E, g-glutamate, Q, N, K, or R
<220> FEATURE:
<221> NAME/KEY: MISC_FEATURE
<222> LOCATION: (14)..(14)
<223> OTHER INFORMATION: X at position 14 can be any amino acid, but
      preferably Q, A, S, T, G, D, isoD, E, g-glutamate, N, K, or R
<220> FEATURE:
<221> NAME/KEY: MISC_FEATURE
<222> LOCATION: (15)..(15)
<223> OTHER INFORMATION: X at position 15 is L, V, I, F, or M, or a non-
      hydrophobic amino acid, or A
<220> FEATURE:
<221> NAME/KEY: MISC_FEATURE
<222> LOCATION: (16)..(16)
<223> OTHER INFORMATION: X at position 16 is L, V, I, F, or M, or a non-
      hydrophobic amino acid, or A
<220> FEATURE:
<221> NAME/KEY: MISC_FEATURE
<222> LOCATION: (17)..(17)
<223> OTHER INFORMATION: X at position 17 can be any amino acid, but
      preferably A, S, T, G, D, isoD, E, g-glutamate, Q, N, K, or R
<220> FEATURE:
<221> NAME/KEY: MISC_FEATURE
<222> LOCATION: (18)..(18)
<223> OTHER INFORMATION: X at position 18 can be any amino acid, but
      preferably Q, A, S, T, G, D, isoD, E, g-glutamate, N, K, or R
<220> FEATURE:
```

<221> NAME/KEY: MISC_FEATURE
<222> LOCATION: (19)..(19)
<223> OTHER INFORMATION: X at position 19 is L, V, I, F, or M, or a non-
      hydrophobic amino acid, or A
<220> FEATURE:
<221> NAME/KEY: MISC_FEATURE
<222> LOCATION: (20)..(20)
<223> OTHER INFORMATION: X at position 20 is L, V, I, F, or M, or a non-
      hydrophobic amino acid, or A
<220> FEATURE:
<221> NAME/KEY: MISC_FEATURE
<222> LOCATION: (21)..(21)
<223> OTHER INFORMATION: X at position 21 can be any amino acid, but
      preferably K, A, S, T, G, D, isoD, E, g-glutamate, Q, N, or R
<220> FEATURE:
<221> NAME/KEY: MISC_FEATURE
<222> LOCATION: (22)..(22)
<223> OTHER INFORMATION: X at position 22 can be any amino acid, but
      preferably S, A,T, G, D, isoD, E, g-glutamate, Q, N, K, or R
<220> FEATURE:
<221> NAME/KEY: MISC_FEATURE
<222> LOCATION: (23)..(23)
<223> OTHER INFORMATION: X at position 23 is L, V, I, F, or M, or a non-
      hydrophobic amino acid, or A
<220> FEATURE:
<221> NAME/KEY: MISC_FEATURE
<222> LOCATION: (24)..(24)
<223> OTHER INFORMATION: X at position 24 is L, V, I, F, or M, or a non-
      hydrophobic amino acid, or A
<220> FEATURE:
<221> NAME/KEY: MISC_FEATURE
<222> LOCATION: (25)..(25)
<223> OTHER INFORMATION: X at position 25 can be any amino acid, but
      preferably S, A, T, G, D, isoD, E, g-glutamate, Q, N, K, or R
<220> FEATURE:
<221> NAME/KEY: MISC_FEATURE
<222> LOCATION: (26)..(26)
<223> OTHER INFORMATION: X at position 26 can be any amino acid, but
      preferably P, S, A, T, G, D, isoD, E, g-glutamate, Q, N, K, or R
<220> FEATURE:
<221> NAME/KEY: MISC_FEATURE
<222> LOCATION: (27)..(27)
<223> OTHER INFORMATION: X at position 27 can be any amino acid, but
      preferably Q, S, A, T, G, D, isoD, E, g-glutamate, N, K, or R

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 13
<211> LENGTH: 13
<212> TYPE: PRT
<213> ORGANISM: Artificial
<220> FEATURE:
<223> OTHER INFORMATION: Modified P17/18 min consensus
<220> FEATURE:
<221> NAME/KEY: MISC_FEATURE
<222> LOCATION: (1)..(1)
<223> OTHER INFORMATION: X at position 1 is L, I, V, F, or M, or a non-
      hydrophobic amino acid, or A
<220> FEATURE:
<221> NAME/KEY: MISC_FEATURE
<222> LOCATION: (2)..(2)
<223> OTHER INFORMATION: X at position 2 can be any amino acid, but
      preferably A, S, T, G, D, isoD, E, g-glutamate, Q, N, K, or R
<220> FEATURE:
<221> NAME/KEY: MISC_FEATURE
<222> LOCATION: (3)..(3)
<223> OTHER INFORMATION: X at position 3 can be any amino acid, but
      preferably Q, A, S, T, G, D, isoD, E, g-glutamate, N, K, or R
<220> FEATURE:
<221> NAME/KEY: MISC_FEATURE
<222> LOCATION: (4)..(4)
<223> OTHER INFORMATION: X at position 4 is L, I, V, F, or M, or a non-

```
       hydrophobic amino acid, or A
<220>  FEATURE:
<221>  NAME/KEY: MISC_FEATURE
<222>  LOCATION: (5)..(5)
<223>  OTHER INFORMATION: X at position 5 is L, I, V, F, or M, or a non-
       hydrophobic amino acid, or A
<220>  FEATURE:
<221>  NAME/KEY: MISC_FEATURE
<222>  LOCATION: (6)..(6)
<223>  OTHER INFORMATION: X at position 6 can be any amino acid, but
       preferably A, S, T, G, D, isoD, E, g-glutamate, Q, N, K, or R
<220>  FEATURE:
<221>  NAME/KEY: MISC_FEATURE
<222>  LOCATION: (7)..(7)
<223>  OTHER INFORMATION: X at position 7 can be any amino acid, but
       preferably Q, A, S, T, G, D, isoD, E, g-glutamate, N, K, or R
<220>  FEATURE:
<221>  NAME/KEY: MISC_FEATURE
<222>  LOCATION: (8)..(8)
<223>  OTHER INFORMATION: X at position 8 is L, I, V, F, or M, or a non-
       hydrophobic amino acid, or A
<220>  FEATURE:
<221>  NAME/KEY: MISC_FEATURE
<222>  LOCATION: (9)..(9)
<223>  OTHER INFORMATION: X at position 9 is L, I, V, F, or M, or a non-
       hydrophobic amino acid, or A
<220>  FEATURE:
<221>  NAME/KEY: MISC_FEATURE
<222>  LOCATION: (10)..(10)
<223>  OTHER INFORMATION: X at position 10 can be any amino acid, but
       preferably K, A, S, T, G, D, isoD, E, g-glutamate, Q, N, or R
<220>  FEATURE:
<221>  NAME/KEY: MISC_FEATURE
<222>  LOCATION: (11)..(11)
<223>  OTHER INFORMATION: X at position 11 can be any amino acid, but
       preferably S, A,T, G, D, isoD, E, g-glutamate, Q, N, K, or R
<220>  FEATURE:
<221>  NAME/KEY: MISC_FEATURE
<222>  LOCATION: (12)..(12)
<223>  OTHER INFORMATION: X at position 12 is L, I, V, F, or M, or a non-
       hydrophobic amino acid, or A
<220>  FEATURE:
<221>  NAME/KEY: MISC_FEATURE
<222>  LOCATION: (13)..(13)
<223>  OTHER INFORMATION: X at position 13 is L, I, V, F, or M, or a non-
       hydrophobic amino acid, or A

<400>  SEQUENCE: 13

Xaa Xaa Xaa Xaa Xaa Xaa Xaa Xaa Xaa Xaa Xaa Xaa Xaa
1               5                   10

<210>  SEQ ID NO 14
<211>  LENGTH: 13
<212>  TYPE: PRT
<213>  ORGANISM: Artificial
<220>  FEATURE:
<223>  OTHER INFORMATION: Modified P19 consensus
<220>  FEATURE:
<221>  NAME/KEY: MISC_FEATURE
<222>  LOCATION: (1)..(1)
<223>  OTHER INFORMATION: X at position 1 is optional and can be L, I, V
       , F, or M
<220>  FEATURE:
<221>  NAME/KEY: MISC_FEATURE
<222>  LOCATION: (2)..(2)
<223>  OTHER INFORMATION: X at position 2 is L, V, I, F, or M, or a non-
       hydrophobic amino acid, or A
<220>  FEATURE:
<221>  NAME/KEY: MISC_FEATURE
<222>  LOCATION: (3)..(3)
<223>  OTHER INFORMATION: X at position 3 can be any amino acid, but
       preferably K, A, S, T, G, D, isoD, E, g-glutamate, Q, N, or R
<220>  FEATURE:
<221>  NAME/KEY: MISC_FEATURE
<222>  LOCATION: (4)..(4)
<223>  OTHER INFORMATION: X at position 4 can be any amino acid, but
       preferably A, S, T, G, D, isoD, E, g-glutamate, Q, N, K, or R
```

```
<220> FEATURE:
<221> NAME/KEY: MISC_FEATURE
<222> LOCATION: (5)..(5)
<223> OTHER INFORMATION: X at position 5 is L, V, I, F, or M, or a non-
      hydrophobic amino acid, or A
<220> FEATURE:
<221> NAME/KEY: MISC_FEATURE
<222> LOCATION: (6)..(6)
<223> OTHER INFORMATION: X at position 6 is L, V, I, F, or M, or a non-
      hydrophobic amino acid, or A
<220> FEATURE:
<221> NAME/KEY: MISC_FEATURE
<222> LOCATION: (7)..(7)
<223> OTHER INFORMATION: X at position 7 can be any amino acid, but
      preferably K, A, S, T, G, D, isoD, E, g-glutamate, Q, N, or R
<220> FEATURE:
<221> NAME/KEY: MISC_FEATURE
<222> LOCATION: (8)..(8)
<223> OTHER INFORMATION: X at position 8 is L, V, I, F, or M, or a non-
      hydrophobic amino acid, or A
<220> FEATURE:
<221> NAME/KEY: MISC_FEATURE
<222> LOCATION: (9)..(9)
<223> OTHER INFORMATION: X at position 9 is L, V, I, F, or M, or a non-
      hydrophobic amino acid, or A
<220> FEATURE:
<221> NAME/KEY: MISC_FEATURE
<222> LOCATION: (10)..(10)
<223> OTHER INFORMATION: X at position 10 can be any amino acid, but
      preferably A, S, T, G, D, isoD, E, g-glutamate, Q, N, K, or R
<220> FEATURE:
<221> NAME/KEY: MISC_FEATURE
<222> LOCATION: (11)..(11)
<223> OTHER INFORMATION: X at position 11 can be any amino acid, but
      preferably R, A, S, T, G, D, isoD, E, g-glutamate, Q, N, or K
<220> FEATURE:
<221> NAME/KEY: MISC_FEATURE
<222> LOCATION: (12)..(12)
<223> OTHER INFORMATION: X at position 12 is L, V, I, F, or M, or a non-
      hydrophobic amino acid, or A
<220> FEATURE:
<221> NAME/KEY: MISC_FEATURE
<222> LOCATION: (13)..(13)
<223> OTHER INFORMATION: X at position 13 is L, V, I, F, or M, or a non-
      hydrophobic amino acid, or A

<400> SEQUENCE: 14

Xaa Xaa Xaa Xaa Xaa Xaa Xaa Xaa Xaa Xaa Xaa Xaa Xaa
1               5                   10

<210> SEQ ID NO 15
<211> LENGTH: 15
<212> TYPE: PRT
<213> ORGANISM: Artificial
<220> FEATURE:
<223> OTHER INFORMATION: Peptide

<400> SEQUENCE: 15

Asp Val Gly Gln Leu Ile Gly Glu Leu Ile Asp Arg Gly Leu Gln
1               5                   10                  15

<210> SEQ ID NO 16
<211> LENGTH: 21
<212> TYPE: PRT
<213> ORGANISM: Artificial
<220> FEATURE:
<223> OTHER INFORMATION: Peptide

<400> SEQUENCE: 16

Gly Asp Val Gly Gln Leu Ile Gly Glu Leu Ile Asp Arg Gly Leu Gln
1               5                   10                  15

Ser Val Leu Ala Gly
            20
```

```
<210> SEQ ID NO 17
<211> LENGTH: 19
<212> TYPE: PRT
<213> ORGANISM: Artificial
<220> FEATURE:
<223> OTHER INFORMATION: Peptide

<400> SEQUENCE: 17

Ser Ser Arg Ala Leu Gln Glu Val Ile Ala Gln Leu Ala Gln Glu Leu
1               5                   10                  15

Thr His Asn

<210> SEQ ID NO 18
<211> LENGTH: 18
<212> TYPE: PRT
<213> ORGANISM: Artificial
<220> FEATURE:
<223> OTHER INFORMATION: Peptide

<400> SEQUENCE: 18

Gly Leu Glu Asp Ile Lys Ala Ala Leu Asp Thr Leu Ile His Glu Lys
1               5                   10                  15

Leu Gly

<210> SEQ ID NO 19
<211> LENGTH: 33
<212> TYPE: PRT
<213> ORGANISM: Artificial
<220> FEATURE:
<223> OTHER INFORMATION: P14-22L,26E

<400> SEQUENCE: 19

Gln Ala Gly Pro Gln Ser Ala Asn Lys Thr Gly Asn Val Asp Asp Ala
1               5                   10                  15

Asn Asn Gln Asp Pro Leu Gln Ala Leu Glu Gln Leu Leu Glu Asp Leu
                20                  25                  30

Val

<210> SEQ ID NO 20
<211> LENGTH: 33
<212> TYPE: PRT
<213> ORGANISM: Artificial
<220> FEATURE:
<223> OTHER INFORMATION: P14-22A,26L

<400> SEQUENCE: 20

Gln Ala Gly Pro Gln Ser Ala Asn Lys Thr Gly Asn Val Asp Asp Ala
1               5                   10                  15

Asn Asn Gln Asp Pro Ala Gln Ala Leu Leu Gln Leu Leu Glu Asp Leu
                20                  25                  30

Val

<210> SEQ ID NO 21
<211> LENGTH: 33
<212> TYPE: PRT
<213> ORGANISM: Artificial
<220> FEATURE:
<223> OTHER INFORMATION: P14-22A,26E

<400> SEQUENCE: 21

Gln Ala Gly Pro Gln Ser Ala Asn Lys Thr Gly Asn Val Asp Asp Ala
1               5                   10                  15
```

Asn Asn Gln Asp Pro Ala Gln Ala Leu Glu Gln Leu Leu Glu Asp Leu
            20                  25                  30

Val

<210> SEQ ID NO 22
<211> LENGTH: 33
<212> TYPE: PRT
<213> ORGANISM: Artificial
<220> FEATURE:
<223> OTHER INFORMATION: P14-22E,26L

<400> SEQUENCE: 22

Gln Ala Gly Pro Gln Ser Ala Asn Lys Thr Gly Asn Val Asp Asp Ala
1               5                   10                  15

Asn Asn Gln Asp Pro Glu Gln Ala Leu Leu Gln Leu Leu Glu Asp Leu
            20                  25                  30

Val

<210> SEQ ID NO 23
<211> LENGTH: 33
<212> TYPE: PRT
<213> ORGANISM: Artificial
<220> FEATURE:
<223> OTHER INFORMATION: P14-22E,26E

<400> SEQUENCE: 23

Gln Ala Gly Pro Gln Ser Ala Asn Lys Thr Gly Asn Val Asp Asp Ala
1               5                   10                  15

Asn Asn Gln Asp Pro Glu Gln Ala Leu Glu Gln Leu Leu Glu Asp Leu
            20                  25                  30

Val

<210> SEQ ID NO 24
<211> LENGTH: 34
<212> TYPE: PRT
<213> ORGANISM: Artificial
<220> FEATURE:
<223> OTHER INFORMATION: P14-22E,26E-R

<400> SEQUENCE: 24

Gln Ala Gly Pro Gln Ser Ala Asn Glu Thr Gly Asn Val Asp Asp Ala
1               5                   10                  15

Asn Asn Gln Asp Pro Glu Gln Ala Leu Glu Gln Leu Leu Glu Asp Leu
            20                  25                  30

Val Arg

<210> SEQ ID NO 25
<211> LENGTH: 32
<212> TYPE: PRT
<213> ORGANISM: Artificial
<220> FEATURE:
<223> OTHER INFORMATION: P14-22E,26A

<400> SEQUENCE: 25

Gln Ala Gly Pro Gln Ser Ala Asn Lys Thr Gly Asn Val Asp Asp Ala
1               5                   10                  15

Asn Asn Gln Asp Pro Glu Ala Leu Ala Gln Leu Leu Glu Asp Leu Val
            20                  25                  30

<210> SEQ ID NO 26
<211> LENGTH: 33

```
<212> TYPE: PRT
<213> ORGANISM: Artificial
<220> FEATURE:
<223> OTHER INFORMATION: P14-22L,26A

<400> SEQUENCE: 26

Gln Ala Gly Pro Gln Ser Ala Asn Lys Thr Gly Asn Val Asp Asp Ala
1               5                   10                  15

Asn Asn Gln Asp Pro Leu Gln Ala Leu Ala Gln Leu Leu Glu Asp Leu
            20                  25                  30

Val

<210> SEQ ID NO 27
<211> LENGTH: 33
<212> TYPE: PRT
<213> ORGANISM: Artificial
<220> FEATURE:
<223> OTHER INFORMATION: P14-22A,26A

<400> SEQUENCE: 27

Gln Ala Gly Pro Gln Ser Ala Asn Lys Thr Gly Asn Val Asp Asp Ala
1               5                   10                  15

Asn Asn Gln Asp Pro Ala Gln Ala Leu Ala Gln Leu Leu Glu Asp Leu
            20                  25                  30

Val

<210> SEQ ID NO 28
<211> LENGTH: 33
<212> TYPE: PRT
<213> ORGANISM: Artificial
<220> FEATURE:
<223> OTHER INFORMATION: P14-22L,25-26A

<400> SEQUENCE: 28

Gln Ala Gly Pro Gln Ser Ala Asn Lys Thr Gly Asn Val Asp Asp Ala
1               5                   10                  15

Asn Asn Gln Asp Pro Leu Gln Ala Ala Ala Gln Leu Leu Glu Asp Leu
            20                  25                  30

Val

<210> SEQ ID NO 29
<211> LENGTH: 33
<212> TYPE: PRT
<213> ORGANISM: Artificial
<220> FEATURE:
<223> OTHER INFORMATION: P14-22L,28-29A

<400> SEQUENCE: 29

Gln Ala Gly Pro Gln Ser Ala Asn Lys Thr Gly Asn Val Asp Asp Ala
1               5                   10                  15

Asn Asn Gln Asp Pro Leu Gln Ala Leu Leu Gln Ala Ala Glu Asp Leu
            20                  25                  30

Val

<210> SEQ ID NO 30
<211> LENGTH: 33
<212> TYPE: PRT
<213> ORGANISM: Artificial
<220> FEATURE:
<223> OTHER INFORMATION: P14-22L,32-33A

<400> SEQUENCE: 30
```

```
Gln Ala Gly Pro Gln Ser Ala Asn Lys Thr Gly Asn Val Asp Asp Ala
1               5                   10                  15

Asn Asn Gln Asp Pro Leu Gln Ala Leu Leu Gln Leu Leu Glu Asp Ala
            20                  25                  30

Ala

<210> SEQ ID NO 31
<211> LENGTH: 33
<212> TYPE: PRT
<213> ORGANISM: Artificial
<220> FEATURE:
<223> OTHER INFORMATION: P14-22L,26,29A

<400> SEQUENCE: 31

Gln Ala Gly Pro Gln Ser Ala Asn Lys Thr Gly Asn Val Asp Asp Ala
1               5                   10                  15

Asn Asn Gln Asp Pro Leu Gln Ala Leu Ala Gln Leu Ala Glu Asp Leu
            20                  25                  30

Val

<210> SEQ ID NO 32
<211> LENGTH: 33
<212> TYPE: PRT
<213> ORGANISM: Artificial
<220> FEATURE:
<223> OTHER INFORMATION: p14-22L,29,32A

<400> SEQUENCE: 32

Gln Ala Gly Pro Gln Ser Ala Asn Lys Thr Gly Asn Val Asp Asp Ala
1               5                   10                  15

Asn Asn Gln Asp Pro Leu Gln Ala Leu Leu Gln Leu Ala Glu Asp Ala
            20                  25                  30

Val

<210> SEQ ID NO 33
<211> LENGTH: 19
<212> TYPE: PRT
<213> ORGANISM: Artificial
<220> FEATURE:
<223> OTHER INFORMATION: p14f-7D

<400> SEQUENCE: 33

Gln Asp Pro Ala Gln Ala Asp Glu Gln Leu Leu Glu Asp Leu Val Lys
1               5                   10                  15

Leu Leu Lys

<210> SEQ ID NO 34
<211> LENGTH: 19
<212> TYPE: PRT
<213> ORGANISM: Artificial
<220> FEATURE:
<223> OTHER INFORMATION: p14f-10D

<400> SEQUENCE: 34

Gln Asp Pro Ala Gln Ala Leu Glu Gln Asp Leu Glu Asp Leu Val Lys
1               5                   10                  15

Leu Leu Lys

<210> SEQ ID NO 35
<211> LENGTH: 19
<212> TYPE: PRT
<213> ORGANISM: Artificial
```

<220> FEATURE:
<223> OTHER INFORMATION: p14f-11D

<400> SEQUENCE: 35

Gln Asp Pro Ala Gln Ala Leu Glu Gln Leu Glu Asp Leu Val Lys
1               5                   10                  15

Leu Leu Lys

<210> SEQ ID NO 36
<211> LENGTH: 19
<212> TYPE: PRT
<213> ORGANISM: Artificial
<220> FEATURE:
<223> OTHER INFORMATION: p14f-14D

<400> SEQUENCE: 36

Gln Asp Pro Ala Gln Ala Leu Glu Gln Leu Leu Glu Asp Asp Val Lys
1               5                   10                  15

Leu Leu Lys

<210> SEQ ID NO 37
<211> LENGTH: 19
<212> TYPE: PRT
<213> ORGANISM: Artificial
<220> FEATURE:
<223> OTHER INFORMATION: p14f-15D

<400> SEQUENCE: 37

Gln Asp Pro Ala Gln Ala Leu Glu Gln Leu Leu Glu Asp Leu Asp Lys
1               5                   10                  15

Leu Leu Lys

<210> SEQ ID NO 38
<211> LENGTH: 19
<212> TYPE: PRT
<213> ORGANISM: Artificial
<220> FEATURE:
<223> OTHER INFORMATION: p14f-17D

<400> SEQUENCE: 38

Gln Asp Pro Ala Gln Ala Leu Glu Gln Leu Leu Glu Asp Leu Val Lys
1               5                   10                  15

Asp Leu Lys

<210> SEQ ID NO 39
<211> LENGTH: 19
<212> TYPE: PRT
<213> ORGANISM: Artificial
<220> FEATURE:
<223> OTHER INFORMATION: p14f-18D

<400> SEQUENCE: 39

Gln Asp Pro Ala Gln Ala Leu Glu Gln Leu Leu Glu Asp Leu Val Lys
1               5                   10                  15

Leu Asp Lys

<210> SEQ ID NO 40
<211> LENGTH: 19
<212> TYPE: PRT
<213> ORGANISM: Artificial
<220> FEATURE:
<223> OTHER INFORMATION: p14f-7S

<400> SEQUENCE: 40

Gln Asp Pro Ala Gln Ala Ser Glu Gln Leu Leu Glu Asp Leu Val Lys
1               5                   10                  15

Leu Leu Lys

<210> SEQ ID NO 41
<211> LENGTH: 19
<212> TYPE: PRT
<213> ORGANISM: Artificial
<220> FEATURE:
<223> OTHER INFORMATION: p14f-10S

<400> SEQUENCE: 41

Gln Asp Pro Ala Gln Ala Leu Glu Gln Ser Leu Glu Asp Leu Val Lys
1               5                   10                  15

Leu Leu Lys

<210> SEQ ID NO 42
<211> LENGTH: 19
<212> TYPE: PRT
<213> ORGANISM: Artificial
<220> FEATURE:
<223> OTHER INFORMATION: p14f-11S

<400> SEQUENCE: 42

Gln Asp Pro Ala Gln Ala Leu Glu Gln Leu Ser Glu Asp Leu Val Lys
1               5                   10                  15

Leu Leu Lys

<210> SEQ ID NO 43
<211> LENGTH: 19
<212> TYPE: PRT
<213> ORGANISM: Artificial
<220> FEATURE:
<223> OTHER INFORMATION: p14f-14S

<400> SEQUENCE: 43

Gln Asp Pro Ala Gln Ala Leu Glu Gln Leu Leu Glu Asp Ser Val Lys
1               5                   10                  15

Leu Leu Lys

<210> SEQ ID NO 44
<211> LENGTH: 19
<212> TYPE: PRT
<213> ORGANISM: Artificial
<220> FEATURE:
<223> OTHER INFORMATION: p14f-15S

<400> SEQUENCE: 44

Gln Asp Pro Ala Gln Ala Leu Glu Gln Leu Leu Glu Asp Leu Ser Lys
1               5                   10                  15

Leu Leu Lys

<210> SEQ ID NO 45
<211> LENGTH: 19
<212> TYPE: PRT
<213> ORGANISM: Artificial
<220> FEATURE:
<223> OTHER INFORMATION: p14f-17S

<400> SEQUENCE: 45

Gln Asp Pro Ala Gln Ala Leu Glu Gln Leu Leu Glu Asp Leu Val Lys
1               5                   10                  15

```
Ser Leu Lys

<210> SEQ ID NO 46
<211> LENGTH: 19
<212> TYPE: PRT
<213> ORGANISM: Artificial
<220> FEATURE:
<223> OTHER INFORMATION: p14f-18S

<400> SEQUENCE: 46

Gln Asp Pro Ala Gln Ala Leu Glu Gln Leu Leu Glu Asp Leu Val Lys
1               5                   10                  15

Leu Ser Lys

<210> SEQ ID NO 47
<211> LENGTH: 23
<212> TYPE: PRT
<213> ORGANISM: Artificial
<220> FEATURE:
<223> OTHER INFORMATION: P4-14S-13A

<400> SEQUENCE: 47

Ser Gln Gly Ile Ser Glu Lys Gln Leu Asp Gln Leu Ala Ser Gln Leu
1               5                   10                  15

Ile Gln Ala Leu Leu Gln Pro
            20

<210> SEQ ID NO 48
<211> LENGTH: 23
<212> TYPE: PRT
<213> ORGANISM: Artificial
<220> FEATURE:
<223> OTHER INFORMATION: P4-14S-13D

<400> SEQUENCE: 48

Ser Gln Gly Ile Ser Glu Lys Gln Leu Asp Gln Leu Asp Ser Gln Leu
1               5                   10                  15

Ile Gln Ala Leu Leu Gln Pro
            20

<210> SEQ ID NO 49
<211> LENGTH: 23
<212> TYPE: PRT
<213> ORGANISM: Artificial
<220> FEATURE:
<223> OTHER INFORMATION: P4-14S-17D

<400> SEQUENCE: 49

Ser Gln Gly Ile Ser Glu Lys Gln Leu Asp Gln Leu Leu Ser Gln Leu
1               5                   10                  15

Asp Gln Ala Leu Leu Gln Pro
            20

<210> SEQ ID NO 50
<211> LENGTH: 23
<212> TYPE: PRT
<213> ORGANISM: Artificial
<220> FEATURE:
<223> OTHER INFORMATION: P4-14S-21D

<400> SEQUENCE: 50

Ser Gln Gly Ile Ser Glu Lys Gln Leu Asp Gln Leu Leu Ser Gln Leu
1               5                   10                  15

Ile Gln Ala Leu Asp Gln Pro
```

20

<210> SEQ ID NO 51
<211> LENGTH: 22
<212> TYPE: PRT
<213> ORGANISM: Artificial
<220> FEATURE:
<223> OTHER INFORMATION: P4-d18

<400> SEQUENCE: 51

Ser Gln Gly Ile Ser Glu Lys Gln Leu Asp Gln Leu Leu Ser Gln Leu
1               5                   10                  15

Ile Ala Leu Leu Gln Pro
            20

<210> SEQ ID NO 52
<211> LENGTH: 23
<212> TYPE: PRT
<213> ORGANISM: Artificial
<220> FEATURE:
<223> OTHER INFORMATION: P4-14S-9S

<400> SEQUENCE: 52

Ser Gln Gly Ile Ser Glu Lys Gln Ser Asp Gln Leu Leu Ser Gln Leu
1               5                   10                  15

Ile Gln Ala Leu Leu Gln Pro
            20

<210> SEQ ID NO 53
<211> LENGTH: 23
<212> TYPE: PRT
<213> ORGANISM: Artificial
<220> FEATURE:
<223> OTHER INFORMATION: P4-14S-9Y

<400> SEQUENCE: 53

Ser Gln Gly Ile Ser Glu Lys Gln Tyr Asp Gln Leu Leu Ser Gln Leu
1               5                   10                  15

Ile Gln Ala Leu Leu Gln Pro
            20

<210> SEQ ID NO 54
<211> LENGTH: 23
<212> TYPE: PRT
<213> ORGANISM: Artificial
<220> FEATURE:
<223> OTHER INFORMATION: P4-14S-13Q

<400> SEQUENCE: 54

Ser Gln Gly Ile Ser Glu Lys Gln Leu Asp Gln Leu Gln Ser Gln Leu
1               5                   10                  15

Ile Gln Ala Leu Leu Gln Pro
            20

<210> SEQ ID NO 55
<211> LENGTH: 23
<212> TYPE: PRT
<213> ORGANISM: Artificial
<220> FEATURE:
<223> OTHER INFORMATION: P4-14S-16S

<400> SEQUENCE: 55

Ser Gln Gly Ile Ser Glu Lys Gln Leu Asp Gln Leu Leu Ser Gln Ser
1               5                   10                  15

Ile Gln Ala Leu Leu Gln Pro
            20

<210> SEQ ID NO 56
<211> LENGTH: 23
<212> TYPE: PRT
<213> ORGANISM: Artificial
<220> FEATURE:
<223> OTHER INFORMATION: P4-14S-20S

<400> SEQUENCE: 56

Ser Gln Gly Ile Ser Glu Lys Gln Leu Asp Gln Leu Leu Ser Gln Leu
1               5                   10                  15

Ile Gln Ala Ser Leu Gln Pro
            20

<210> SEQ ID NO 57
<211> LENGTH: 23
<212> TYPE: PRT
<213> ORGANISM: Artificial
<220> FEATURE:
<223> OTHER INFORMATION: P4-14S-9A

<400> SEQUENCE: 57

Ser Gln Gly Ile Ser Glu Lys Gln Ala Asp Gln Leu Leu Ser Gln Leu
1               5                   10                  15

Ile Gln Ala Leu Leu Gln Pro
            20

<210> SEQ ID NO 58
<211> LENGTH: 23
<212> TYPE: PRT
<213> ORGANISM: Artificial
<220> FEATURE:
<223> OTHER INFORMATION: P4-14S-9D

<400> SEQUENCE: 58

Ser Gln Gly Ile Ser Glu Lys Gln Asp Asp Gln Leu Leu Ser Gln Leu
1               5                   10                  15

Ile Gln Ala Leu Leu Gln Pro
            20

<210> SEQ ID NO 59
<211> LENGTH: 23
<212> TYPE: PRT
<213> ORGANISM: Artificial
<220> FEATURE:
<223> OTHER INFORMATION: P4-14S-12D

<400> SEQUENCE: 59

Ser Gln Gly Ile Ser Glu Lys Gln Leu Asp Gln Asp Leu Ser Gln Leu
1               5                   10                  15

Ile Gln Ala Leu Leu Gln Pro
            20

<210> SEQ ID NO 60
<211> LENGTH: 23
<212> TYPE: PRT
<213> ORGANISM: Artificial
<220> FEATURE:
<223> OTHER INFORMATION: P4-14S-16A

<400> SEQUENCE: 60

Ser Gln Gly Ile Ser Glu Lys Gln Leu Asp Gln Leu Leu Ser Gln Ala
1               5                   10                  15

Ile Gln Ala Leu Leu Gln Pro
            20

<210> SEQ ID NO 61
<211> LENGTH: 23
<212> TYPE: PRT
<213> ORGANISM: Artificial
<220> FEATURE:
<223> OTHER INFORMATION: P4-14S-17S

<400> SEQUENCE: 61

Ser Gln Gly Ile Ser Glu Lys Gln Leu Asp Gln Leu Leu Ser Gln Leu
1               5                   10                  15

Ser Gln Ala Leu Leu Gln Pro
            20

<210> SEQ ID NO 62
<211> LENGTH: 20
<212> TYPE: PRT
<213> ORGANISM: Artificial
<220> FEATURE:
<223> OTHER INFORMATION: P4-d10,14,18

<400> SEQUENCE: 62

Ser Gln Gly Ile Ser Glu Lys Gln Leu Gln Leu Leu Gln Leu Ile Ala
1               5                   10                  15

Leu Leu Gln Pro
            20

<210> SEQ ID NO 63
<211> LENGTH: 24
<212> TYPE: PRT
<213> ORGANISM: Artificial
<220> FEATURE:
<223> OTHER INFORMATION: P4-i21Q

<400> SEQUENCE: 63

Ser Gln Gly Ile Ser Glu Lys Gln Leu Asp Gln Leu Leu Ser Gln Leu
1               5                   10                  15

Ile Gln Ala Gln Leu Leu Gln Pro
            20

<210> SEQ ID NO 64
<211> LENGTH: 24
<212> TYPE: PRT
<213> ORGANISM: Artificial
<220> FEATURE:
<223> OTHER INFORMATION: P4-i21H

<400> SEQUENCE: 64

Ser Gln Gly Ile Ser Glu Lys Gln Leu Asp Gln Leu Leu Ser Gln Leu
1               5                   10                  15

Ile Gln Ala His Leu Leu Gln Pro
            20

<210> SEQ ID NO 65
<211> LENGTH: 24
<212> TYPE: PRT
<213> ORGANISM: Artificial
<220> FEATURE:
<223> OTHER INFORMATION: P4-i10A

<400> SEQUENCE: 65

Ser Gln Gly Ile Ser Glu Lys Gln Leu Ala Asp Gln Leu Leu Ser Gln

```
1               5                   10                  15
Leu Ile Gln Ala Leu Leu Gln Pro
            20
```

<210> SEQ ID NO 66
<211> LENGTH: 24
<212> TYPE: PRT
<213> ORGANISM: Artificial
<220> FEATURE:
<223> OTHER INFORMATION: P4-i14A

<400> SEQUENCE: 66

```
Ser Gln Gly Ile Ser Glu Lys Gln Leu Asp Gln Leu Leu Ala Ser Gln
1               5                   10                  15

Leu Ile Gln Ala Leu Leu Gln Pro
            20
```

<210> SEQ ID NO 67
<211> LENGTH: 24
<212> TYPE: PRT
<213> ORGANISM: Artificial
<220> FEATURE:
<223> OTHER INFORMATION: P4-i18A

<400> SEQUENCE: 67

```
Ser Gln Gly Ile Ser Glu Lys Gln Leu Asp Gln Leu Leu Ser Gln Leu
1               5                   10                  15

Ile Ala Gln Ala Leu Leu Gln Pro
            20
```

<210> SEQ ID NO 68
<211> LENGTH: 26
<212> TYPE: PRT
<213> ORGANISM: Artificial
<220> FEATURE:
<223> OTHER INFORMATION: P4-i10A,14A,18A

<400> SEQUENCE: 68

```
Ser Gln Gly Ile Ser Glu Lys Gln Leu Ala Asp Gln Leu Leu Ala Ser
1               5                   10                  15

Gln Leu Ile Ala Gln Ala Leu Leu Gln Pro
            20                  25
```

<210> SEQ ID NO 69
<211> LENGTH: 21
<212> TYPE: PRT
<213> ORGANISM: Artificial
<220> FEATURE:
<223> OTHER INFORMATION: P25min-7D

<400> SEQUENCE: 69

```
Ser Glu Glu Glu Glu Glu Asp Thr Gly Val Leu Gln Lys Leu Leu Lys
1               5                   10                  15

Ile Leu Glu Ala Leu
            20
```

<210> SEQ ID NO 70
<211> LENGTH: 21
<212> TYPE: PRT
<213> ORGANISM: Artificial
<220> FEATURE:
<223> OTHER INFORMATION: P25min-10D

<400> SEQUENCE: 70

```
Ser Glu Glu Glu Glu Leu Thr Gly Asp Leu Gln Lys Leu Leu Lys
1               5                   10                  15

Ile Leu Glu Ala Leu
            20

<210> SEQ ID NO 71
<211> LENGTH: 21
<212> TYPE: PRT
<213> ORGANISM: Artificial
<220> FEATURE:
<223> OTHER INFORMATION: P25min-11D

<400> SEQUENCE: 71

Ser Glu Glu Glu Glu Leu Thr Gly Val Asp Gln Lys Leu Leu Lys
1               5                   10                  15

Ile Leu Glu Ala Leu
            20

<210> SEQ ID NO 72
<211> LENGTH: 21
<212> TYPE: PRT
<213> ORGANISM: Artificial
<220> FEATURE:
<223> OTHER INFORMATION: P25min-14D

<400> SEQUENCE: 72

Ser Glu Glu Glu Glu Leu Thr Gly Val Leu Gln Lys Asp Leu Lys
1               5                   10                  15

Ile Leu Glu Ala Leu
            20

<210> SEQ ID NO 73
<211> LENGTH: 21
<212> TYPE: PRT
<213> ORGANISM: Artificial
<220> FEATURE:
<223> OTHER INFORMATION: P25min-15D

<400> SEQUENCE: 73

Ser Glu Glu Glu Glu Leu Thr Gly Val Leu Gln Lys Leu Asp Lys
1               5                   10                  15

Ile Leu Glu Ala Leu
            20

<210> SEQ ID NO 74
<211> LENGTH: 21
<212> TYPE: PRT
<213> ORGANISM: Artificial
<220> FEATURE:
<223> OTHER INFORMATION: P25min-17D

<400> SEQUENCE: 74

Ser Glu Glu Glu Glu Leu Thr Gly Val Leu Gln Lys Leu Leu Lys
1               5                   10                  15

Asp Leu Glu Ala Leu
            20

<210> SEQ ID NO 75
<211> LENGTH: 21
<212> TYPE: PRT
<213> ORGANISM: Artificial
<220> FEATURE:
<223> OTHER INFORMATION: P25min-18D

<400> SEQUENCE: 75
```

-continued

Ser Glu Glu Glu Glu Glu Leu Thr Gly Val Leu Gln Lys Leu Leu Lys
1               5                   10                  15

Ile Asp Glu Ala Leu
            20

<210> SEQ ID NO 76
<211> LENGTH: 21
<212> TYPE: PRT
<213> ORGANISM: Artificial
<220> FEATURE:
<223> OTHER INFORMATION: P25min-21D

<400> SEQUENCE: 76

Ser Glu Glu Glu Glu Glu Leu Thr Gly Val Leu Gln Lys Leu Leu Lys
1               5                   10                  15

Ile Leu Glu Ala Asp
            20

<210> SEQ ID NO 77
<211> LENGTH: 21
<212> TYPE: PRT
<213> ORGANISM: Artificial
<220> FEATURE:
<223> OTHER INFORMATION: P25min-7S

<400> SEQUENCE: 77

Ser Glu Glu Glu Glu Ser Thr Gly Val Leu Gln Lys Leu Leu Lys
1               5                   10                  15

Ile Leu Glu Ala Leu
            20

<210> SEQ ID NO 78
<211> LENGTH: 21
<212> TYPE: PRT
<213> ORGANISM: Artificial
<220> FEATURE:
<223> OTHER INFORMATION: P25min-10S

<400> SEQUENCE: 78

Ser Glu Glu Glu Glu Glu Leu Thr Gly Ser Leu Gln Lys Leu Leu Lys
1               5                   10                  15

Ile Leu Glu Ala Leu
            20

<210> SEQ ID NO 79
<211> LENGTH: 21
<212> TYPE: PRT
<213> ORGANISM: Artificial
<220> FEATURE:
<223> OTHER INFORMATION: P25min-11S

<400> SEQUENCE: 79

Ser Glu Glu Glu Glu Glu Leu Thr Gly Val Ser Gln Lys Leu Leu Lys
1               5                   10                  15

Ile Leu Glu Ala Leu
            20

<210> SEQ ID NO 80
<211> LENGTH: 21
<212> TYPE: PRT
<213> ORGANISM: Artificial
<220> FEATURE:
<223> OTHER INFORMATION: P25min-14S

```
<400> SEQUENCE: 80

Ser Glu Glu Glu Glu Glu Leu Thr Gly Val Leu Gln Lys Ser Leu Lys
1               5                   10                  15

Ile Leu Glu Ala Leu
            20

<210> SEQ ID NO 81
<211> LENGTH: 21
<212> TYPE: PRT
<213> ORGANISM: Artificial
<220> FEATURE:
<223> OTHER INFORMATION: P25min-15S

<400> SEQUENCE: 81

Ser Glu Glu Glu Glu Glu Leu Thr Gly Val Leu Gln Lys Leu Ser Lys
1               5                   10                  15

Ile Leu Glu Ala Leu
            20

<210> SEQ ID NO 82
<211> LENGTH: 21
<212> TYPE: PRT
<213> ORGANISM: Artificial
<220> FEATURE:
<223> OTHER INFORMATION: P25min-17S

<400> SEQUENCE: 82

Ser Glu Glu Glu Glu Glu Leu Thr Gly Val Leu Gln Lys Leu Leu Lys
1               5                   10                  15

Ser Leu Glu Ala Leu
            20

<210> SEQ ID NO 83
<211> LENGTH: 21
<212> TYPE: PRT
<213> ORGANISM: Artificial
<220> FEATURE:
<223> OTHER INFORMATION: P25min-18S

<400> SEQUENCE: 83

Ser Glu Glu Glu Glu Glu Leu Thr Gly Val Leu Gln Lys Leu Leu Lys
1               5                   10                  15

Ile Ser Glu Ala Leu
            20

<210> SEQ ID NO 84
<211> LENGTH: 21
<212> TYPE: PRT
<213> ORGANISM: Artificial
<220> FEATURE:
<223> OTHER INFORMATION: P25min-21S

<400> SEQUENCE: 84

Ser Glu Glu Glu Glu Glu Leu Thr Gly Val Leu Gln Lys Leu Leu Lys
1               5                   10                  15

Ile Leu Glu Ala Ser
            20

<210> SEQ ID NO 85
<211> LENGTH: 19
<212> TYPE: PRT
<213> ORGANISM: Artificial
<220> FEATURE:
<223> OTHER INFORMATION: P18min-7D
```

-continued

<400> SEQUENCE: 85

Ser Glu Glu Glu Glu Glu Asp Ala Gln Leu Leu Ala Gln Leu Leu Lys
1               5                   10                  15

Ser Leu Leu

<210> SEQ ID NO 86
<211> LENGTH: 19
<212> TYPE: PRT
<213> ORGANISM: Artificial
<220> FEATURE:
<223> OTHER INFORMATION: P18min-10D

<400> SEQUENCE: 86

Ser Glu Glu Glu Glu Glu Leu Ala Gln Asp Leu Ala Gln Leu Leu Lys
1               5                   10                  15

Ser Leu Leu

<210> SEQ ID NO 87
<211> LENGTH: 19
<212> TYPE: PRT
<213> ORGANISM: Artificial
<220> FEATURE:
<223> OTHER INFORMATION: P18min-11D

<400> SEQUENCE: 87

Ser Glu Glu Glu Glu Glu Leu Ala Gln Leu Asp Ala Gln Leu Leu Lys
1               5                   10                  15

Ser Leu Leu

<210> SEQ ID NO 88
<211> LENGTH: 19
<212> TYPE: PRT
<213> ORGANISM: Artificial
<220> FEATURE:
<223> OTHER INFORMATION: P18min-14D

<400> SEQUENCE: 88

Ser Glu Glu Glu Glu Glu Leu Ala Gln Leu Leu Ala Gln Asp Leu Lys
1               5                   10                  15

Ser Leu Leu

<210> SEQ ID NO 89
<211> LENGTH: 19
<212> TYPE: PRT
<213> ORGANISM: Artificial
<220> FEATURE:
<223> OTHER INFORMATION: P18min-15D

<400> SEQUENCE: 89

Ser Glu Glu Glu Glu Glu Leu Ala Gln Leu Leu Ala Gln Leu Asp Lys
1               5                   10                  15

Ser Leu Leu

<210> SEQ ID NO 90
<211> LENGTH: 19
<212> TYPE: PRT
<213> ORGANISM: Artificial
<220> FEATURE:
<223> OTHER INFORMATION: P18min-18D

<400> SEQUENCE: 90

Ser Glu Glu Glu Glu Glu Leu Ala Gln Leu Leu Ala Gln Leu Leu Lys

-continued

```
                1               5                  10                 15

Ser Asp Leu

<210> SEQ ID NO 91
<211> LENGTH: 19
<212> TYPE: PRT
<213> ORGANISM: Artificial
<220> FEATURE:
<223> OTHER INFORMATION: P18min-19D

<400> SEQUENCE: 91

Ser Glu Glu Glu Glu Glu Leu Ala Gln Leu Leu Ala Gln Leu Leu Lys
1               5                  10                 15

Ser Leu Asp

<210> SEQ ID NO 92
<211> LENGTH: 19
<212> TYPE: PRT
<213> ORGANISM: Artificial
<220> FEATURE:
<223> OTHER INFORMATION: P18min-7S

<400> SEQUENCE: 92

Ser Glu Glu Glu Glu Glu Ser Ala Gln Leu Leu Ala Gln Leu Leu Lys
1               5                  10                 15

Ser Leu Leu

<210> SEQ ID NO 93
<211> LENGTH: 19
<212> TYPE: PRT
<213> ORGANISM: Artificial
<220> FEATURE:
<223> OTHER INFORMATION: P18min-10S

<400> SEQUENCE: 93

Ser Glu Glu Glu Glu Glu Leu Ala Gln Ser Leu Ala Gln Leu Leu Lys
1               5                  10                 15

Ser Leu Leu

<210> SEQ ID NO 94
<211> LENGTH: 19
<212> TYPE: PRT
<213> ORGANISM: Artificial
<220> FEATURE:
<223> OTHER INFORMATION: P18min-11S

<400> SEQUENCE: 94

Ser Glu Glu Glu Glu Glu Leu Ala Gln Leu Ser Ala Gln Leu Leu Lys
1               5                  10                 15

Ser Leu Leu

<210> SEQ ID NO 95
<211> LENGTH: 19
<212> TYPE: PRT
<213> ORGANISM: Artificial
<220> FEATURE:
<223> OTHER INFORMATION: P18min-14S

<400> SEQUENCE: 95

Ser Glu Glu Glu Glu Glu Leu Ala Gln Leu Leu Ala Gln Ser Leu Lys
1               5                  10                 15

Ser Leu Leu
```

<210> SEQ ID NO 96
<211> LENGTH: 19
<212> TYPE: PRT
<213> ORGANISM: Artificial
<220> FEATURE:
<223> OTHER INFORMATION: P18min-15S

<400> SEQUENCE: 96

Ser Glu Glu Glu Glu Glu Leu Ala Gln Leu Leu Ala Gln Leu Ser Lys
1               5                   10                  15

Ser Leu Leu

<210> SEQ ID NO 97
<211> LENGTH: 19
<212> TYPE: PRT
<213> ORGANISM: Artificial
<220> FEATURE:
<223> OTHER INFORMATION: P18min-18S

<400> SEQUENCE: 97

Ser Glu Glu Glu Glu Glu Leu Ala Gln Leu Leu Ala Gln Leu Leu Lys
1               5                   10                  15

Ser Ser Leu

<210> SEQ ID NO 98
<211> LENGTH: 19
<212> TYPE: PRT
<213> ORGANISM: Artificial
<220> FEATURE:
<223> OTHER INFORMATION: P18min-19S

<400> SEQUENCE: 98

Ser Glu Glu Glu Glu Glu Leu Ala Gln Leu Leu Ala Gln Leu Leu Lys
1               5                   10                  15

Ser Leu Ser

<210> SEQ ID NO 99
<211> LENGTH: 18
<212> TYPE: PRT
<213> ORGANISM: Artificial
<220> FEATURE:
<223> OTHER INFORMATION: P19min-7D

<400> SEQUENCE: 99

Ser Glu Glu Glu Glu Glu Asp Lys Ala Leu Leu Lys Leu Ile Ala Arg
1               5                   10                  15

Leu Leu

<210> SEQ ID NO 100
<211> LENGTH: 18
<212> TYPE: PRT
<213> ORGANISM: Artificial
<220> FEATURE:
<223> OTHER INFORMATION: P19min-10D

<400> SEQUENCE: 100

Ser Glu Glu Glu Glu Glu Leu Lys Ala Asp Leu Lys Leu Ile Ala Arg
1               5                   10                  15

Leu Leu

<210> SEQ ID NO 101
<211> LENGTH: 18
<212> TYPE: PRT

<213> ORGANISM: Artificial
<220> FEATURE:
<223> OTHER INFORMATION: P19min-11D

<400> SEQUENCE: 101

Ser Glu Glu Glu Glu Glu Leu Lys Ala Leu Asp Lys Leu Ile Ala Arg
1               5                   10                  15

Leu Leu

<210> SEQ ID NO 102
<211> LENGTH: 18
<212> TYPE: PRT
<213> ORGANISM: Artificial
<220> FEATURE:
<223> OTHER INFORMATION: P19min-13D

<400> SEQUENCE: 102

Ser Glu Glu Glu Glu Glu Leu Lys Ala Leu Leu Lys Asp Ile Ala Arg
1               5                   10                  15

Leu Leu

<210> SEQ ID NO 103
<211> LENGTH: 18
<212> TYPE: PRT
<213> ORGANISM: Artificial
<220> FEATURE:
<223> OTHER INFORMATION: P19min-14D

<400> SEQUENCE: 103

Ser Glu Glu Glu Glu Glu Leu Lys Ala Leu Leu Lys Leu Asp Ala Arg
1               5                   10                  15

Leu Leu

<210> SEQ ID NO 104
<211> LENGTH: 18
<212> TYPE: PRT
<213> ORGANISM: Artificial
<220> FEATURE:
<223> OTHER INFORMATION: P19min-17D

<400> SEQUENCE: 104

Ser Glu Glu Glu Glu Glu Leu Lys Ala Leu Leu Lys Leu Ile Ala Arg
1               5                   10                  15

Asp Leu

<210> SEQ ID NO 105
<211> LENGTH: 18
<212> TYPE: PRT
<213> ORGANISM: Artificial
<220> FEATURE:
<223> OTHER INFORMATION: P19min-18D

<400> SEQUENCE: 105

Ser Glu Glu Glu Glu Glu Leu Lys Ala Leu Leu Lys Leu Ile Ala Arg
1               5                   10                  15

Leu Asp

<210> SEQ ID NO 106
<211> LENGTH: 18
<212> TYPE: PRT
<213> ORGANISM: Artificial
<220> FEATURE:
<223> OTHER INFORMATION: P19min-7S

```
<400> SEQUENCE: 106

Ser Glu Glu Glu Glu Glu Ser Lys Ala Leu Leu Lys Leu Ile Ala Arg
1               5                   10                  15

Leu Leu

<210> SEQ ID NO 107
<211> LENGTH: 18
<212> TYPE: PRT
<213> ORGANISM: Artificial
<220> FEATURE:
<223> OTHER INFORMATION: P19min-10S

<400> SEQUENCE: 107

Ser Glu Glu Glu Glu Glu Leu Lys Ala Ser Leu Lys Leu Ile Ala Arg
1               5                   10                  15

Leu Leu

<210> SEQ ID NO 108
<211> LENGTH: 18
<212> TYPE: PRT
<213> ORGANISM: Artificial
<220> FEATURE:
<223> OTHER INFORMATION: P19min-11S

<400> SEQUENCE: 108

Ser Glu Glu Glu Glu Glu Leu Lys Ala Leu Ser Lys Leu Ile Ala Arg
1               5                   10                  15

Leu Leu

<210> SEQ ID NO 109
<211> LENGTH: 18
<212> TYPE: PRT
<213> ORGANISM: Artificial
<220> FEATURE:
<223> OTHER INFORMATION: P19min-13S

<400> SEQUENCE: 109

Ser Glu Glu Glu Glu Glu Leu Lys Ala Leu Leu Lys Ser Ile Ala Arg
1               5                   10                  15

Leu Leu

<210> SEQ ID NO 110
<211> LENGTH: 18
<212> TYPE: PRT
<213> ORGANISM: Artificial
<220> FEATURE:
<223> OTHER INFORMATION: P19min-14S

<400> SEQUENCE: 110

Ser Glu Glu Glu Glu Glu Leu Lys Ala Leu Leu Lys Leu Ser Ala Arg
1               5                   10                  15

Leu Leu

<210> SEQ ID NO 111
<211> LENGTH: 18
<212> TYPE: PRT
<213> ORGANISM: Artificial
<220> FEATURE:
<223> OTHER INFORMATION: P19min-17S

<400> SEQUENCE: 111

Ser Glu Glu Glu Glu Glu Leu Lys Ala Leu Leu Lys Leu Ile Ala Arg
1               5                   10                  15
```

Ser Leu

<210> SEQ ID NO 112
<211> LENGTH: 18
<212> TYPE: PRT
<213> ORGANISM: Artificial
<220> FEATURE:
<223> OTHER INFORMATION: P19min-18S

<400> SEQUENCE: 112

Ser Glu Glu Glu Glu Glu Leu Lys Ala Leu Leu Lys Leu Ile Ala Arg
1               5                   10                  15

Leu Ser

<210> SEQ ID NO 113
<211> LENGTH: 33
<212> TYPE: PRT
<213> ORGANISM: Artificial
<220> FEATURE:
<223> OTHER INFORMATION: P14

<400> SEQUENCE: 113

Gln Ala Gly Pro Gln Ser Ala Asn Lys Thr Gly Asn Val Asp Asp Ala
1               5                   10                  15

Asn Asn Gln Asp Pro Met Gln Ala Leu Met Gln Leu Leu Glu Asp Leu
            20                  25                  30

Val

<210> SEQ ID NO 114
<211> LENGTH: 18
<212> TYPE: PRT
<213> ORGANISM: Artificial
<220> FEATURE:
<223> OTHER INFORMATION: P14a

<400> SEQUENCE: 114

Ala Asn Asn Gln Asp Pro Met Gln Ala Leu Met Gln Leu Leu Glu Asp
1               5                   10                  15

Leu Val

<210> SEQ ID NO 115
<211> LENGTH: 33
<212> TYPE: PRT
<213> ORGANISM: Artificial
<220> FEATURE:
<223> OTHER INFORMATION: P14-22L,26L

<400> SEQUENCE: 115

Gln Ala Gly Pro Gln Ser Ala Asn Lys Thr Gly Asn Val Asp Asp Ala
1               5                   10                  15

Asn Asn Gln Asp Pro Leu Gln Ala Leu Leu Gln Leu Leu Glu Asp Leu
            20                  25                  30

Val

<210> SEQ ID NO 116
<211> LENGTH: 9
<212> TYPE: PRT
<213> ORGANISM: Artificial
<220> FEATURE:
<223> OTHER INFORMATION: HR Box Truncation Peptide Consensus
<220> FEATURE:
<221> NAME/KEY: MISC_FEATURE
<222> LOCATION: (2)..(2)

```
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is any amino acid
<220> FEATURE:
<221> NAME/KEY: MISC_FEATURE
<222> LOCATION: (4)..(4)
<223> OTHER INFORMATION: X at position 4 is L or I
<220> FEATURE:
<221> NAME/KEY: MISC_FEATURE
<222> LOCATION: (5)..(5)
<223> OTHER INFORMATION: X at position 5 is L or I
<220> FEATURE:
<221> NAME/KEY: MISC_FEATURE
<222> LOCATION: (6)..(6)
<223> OTHER INFORMATION: X at position 6 is any amino acid
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, or V
<220> FEATURE:
<221> NAME/KEY: MISC_FEATURE
<222> LOCATION: (9)..(9)
<223> OTHER INFORMATION: X at position 9 is L, I, or V

<400> SEQUENCE: 116

Leu Xaa Xaa Xaa Xaa Xaa Xaa Xaa
1               5

<210> SEQ ID NO 117
<211> LENGTH: 31
<212> TYPE: PRT
<213> ORGANISM: Artificial
<220> FEATURE:
<223> OTHER INFORMATION: P14-dN2

<400> SEQUENCE: 117

Gly Pro Gln Ser Ala Asn Lys Thr Gly Asn Val Asp Asp Ala Asn Asn
1               5                   10                  15

Gln Asp Pro Met Gln Ala Leu Met Gln Leu Leu Glu Asp Leu Val
            20                  25                  30

<210> SEQ ID NO 118
<211> LENGTH: 29
<212> TYPE: PRT
<213> ORGANISM: Artificial
<220> FEATURE:
<223> OTHER INFORMATION: P14-dN4

<400> SEQUENCE: 118

Gln Ser Ala Asn Lys Thr Gly Asn Val Asp Asp Ala Asn Asn Gln Asp
1               5                   10                  15

Pro Met Gln Ala Leu Met Gln Leu Leu Glu Asp Leu Val
            20                  25

<210> SEQ ID NO 119
<211> LENGTH: 27
<212> TYPE: PRT
<213> ORGANISM: Artificial
<220> FEATURE:
<223> OTHER INFORMATION: P14-dN6

<400> SEQUENCE: 119

Ala Asn Lys Thr Gly Asn Val Asp Asp Ala Asn Asn Gln Asp Pro Met
1               5                   10                  15
```

```
Gln Ala Leu Met Gln Leu Leu Glu Asp Leu Val
            20                  25
```

<210> SEQ ID NO 120
<211> LENGTH: 25
<212> TYPE: PRT
<213> ORGANISM: Artificial
<220> FEATURE:
<223> OTHER INFORMATION: P14-dN8

<400> SEQUENCE: 120

```
Lys Thr Gly Asn Val Asp Asp Ala Asn Asn Gln Asp Pro Met Gln Ala
1               5                   10                  15

Leu Met Gln Leu Leu Glu Asp Leu Val
            20                  25
```

<210> SEQ ID NO 121
<211> LENGTH: 32
<212> TYPE: PRT
<213> ORGANISM: Artificial
<220> FEATURE:
<223> OTHER INFORMATION: P14-dc1

<400> SEQUENCE: 121

```
Gln Ala Gly Pro Gln Ser Ala Asn Lys Thr Gly Asn Val Asp Asp Ala
1               5                   10                  15

Asn Asn Gln Asp Pro Met Gln Ala Leu Met Gln Leu Leu Glu Asp Leu
            20                  25                  30
```

<210> SEQ ID NO 122
<211> LENGTH: 31
<212> TYPE: PRT
<213> ORGANISM: Artificial
<220> FEATURE:
<223> OTHER INFORMATION: P14-dc2

<400> SEQUENCE: 122

```
Gln Ala Gly Pro Gln Ser Ala Asn Lys Thr Gly Asn Val Asp Asp Ala
1               5                   10                  15

Asn Asn Gln Asp Pro Met Gln Ala Leu Met Gln Leu Leu Glu Asp
            20                  25                  30
```

<210> SEQ ID NO 123
<211> LENGTH: 29
<212> TYPE: PRT
<213> ORGANISM: Artificial
<220> FEATURE:
<223> OTHER INFORMATION: P14-dc4

<400> SEQUENCE: 123

```
Gln Ala Gly Pro Gln Ser Ala Asn Lys Thr Gly Asn Val Asp Asp Ala
1               5                   10                  15

Asn Asn Gln Asp Pro Met Gln Ala Leu Met Gln Leu Leu
            20                  25
```

<210> SEQ ID NO 124
<211> LENGTH: 18
<212> TYPE: PRT
<213> ORGANISM: Artificial
<220> FEATURE:
<223> OTHER INFORMATION: P14-32

<400> SEQUENCE: 124

```
Ser Glu Glu Glu Glu Glu Leu Glu Gln Leu Leu Glu Asp Leu Val Lys
```

```
1               5                  10                  15

Leu Leu

<210> SEQ ID NO 125
<211> LENGTH: 13
<212> TYPE: PRT
<213> ORGANISM: Artificial
<220> FEATURE:
<223> OTHER INFORMATION: HR Box consensus peptide
<220> FEATURE:
<221> NAME/KEY: MISC_FEATURE
<222> LOCATION: (1)..(1)
<223> OTHER INFORMATION: X at position 1 is L, I, V, or F
<220> FEATURE:
<221> NAME/KEY: MISC_FEATURE
<222> LOCATION: (2)..(2)
<223> OTHER INFORMATION: X at position 2 is any amino acid
<220> FEATURE:
<221> NAME/KEY: MISC_FEATURE
<222> LOCATION: (3)..(3)
<223> OTHER INFORMATION: X at position 3 is any amino acid
<220> FEATURE:
<221> NAME/KEY: MISC_FEATURE
<222> LOCATION: (4)..(4)
<223> OTHER INFORMATION: X at position 4 is L, I, V, or F
<220> FEATURE:
<221> NAME/KEY: MISC_FEATURE
<222> LOCATION: (5)..(5)
<223> OTHER INFORMATION: X at position 5 is L or I
<220> FEATURE:
<221> NAME/KEY: MISC_FEATURE
<222> LOCATION: (6)..(6)
<223> OTHER INFORMATION: X at position 6 is any amino acid
<220> FEATURE:
<221> NAME/KEY: MISC_FEATURE
<222> LOCATION: (7)..(7)
<223> OTHER INFORMATION: X at position 7 is any amino acid
<220> FEATURE:
<221> NAME/KEY: MISC_FEATURE
<222> LOCATION: (8)..(8)
<223> OTHER INFORMATION: X at position 8 is L, I, or V
<220> FEATURE:
<221> NAME/KEY: MISC_FEATURE
<222> LOCATION: (9)..(9)
<223> OTHER INFORMATION: X at position 9 is L or I
<220> FEATURE:
<221> NAME/KEY: MISC_FEATURE
<222> LOCATION: (10)..(10)
<223> OTHER INFORMATION: X at position 10 is any amino acid
<220> FEATURE:
<221> NAME/KEY: MISC_FEATURE
<222> LOCATION: (11)..(11)
<223> OTHER INFORMATION: X at position 11 is any amino acid
<220> FEATURE:
<221> NAME/KEY: MISC_FEATURE
<222> LOCATION: (12)..(12)
<223> OTHER INFORMATION: X at position 12 is L, I, V, or F
<220> FEATURE:
<221> NAME/KEY: MISC_FEATURE
<222> LOCATION: (13)..(13)
<223> OTHER INFORMATION: X at position 13 is L, I, V, or F

<400> SEQUENCE: 125

Xaa Xaa Xaa Xaa Xaa Xaa Xaa Xaa Xaa Xaa Xaa Xaa Xaa
1               5                  10

<210> SEQ ID NO 126
<211> LENGTH: 11
<212> TYPE: PRT
<213> ORGANISM: Artificial
<220> FEATURE:
<223> OTHER INFORMATION: P3 minimum
<220> FEATURE:
<221> NAME/KEY: MISC_FEATURE
<222> LOCATION: (1)..(1)
```

<223> OTHER INFORMATION: X at position 1 is an optional tripeptide LXX,
      where each X is a hydrophilic amino acid, preferably K, A, S, T,
      G, D, isoD, E, g-glutamate, Q, N, or R
<220> FEATURE:
<221> NAME/KEY: MISC_FEATURE
<222> LOCATION: (4)..(4)
<223> OTHER INFORMATION: X at position 4 is any hydrophilic amino acid,
      preferably K, A, S, T, G, D, isoD, E, g-glutamate, Q, N, or R
<220> FEATURE:
<221> NAME/KEY: MISC_FEATURE
<222> LOCATION: (7)..(7)
<223> OTHER INFORMATION: X at position 7 is any hydrophilic amino acid,
      preferably K, A, S, T, G, D, isoD, E, g-glutamate, Q, N, or R
<220> FEATURE:
<221> NAME/KEY: MISC_FEATURE
<222> LOCATION: (8)..(8)
<223> OTHER INFORMATION: X at position 8 is any hydrophilic amino acid,
      preferably K, A, S, T, G, D, isoD, E, g-glutamate, Q, N, or R
<220> FEATURE:
<221> NAME/KEY: MISC_FEATURE
<222> LOCATION: (11)..(11)
<223> OTHER INFORMATION: X at position 11 is an optional tetrapeptide
      XXLF, where each X is a hydrophilic amino acid, preferably K, A,
      S, T, G, D, isoD, E, g-glutamate, Q, N, or R

<400> SEQUENCE: 126

Xaa Leu Leu Xaa Leu Phe Xaa Xaa Ile Leu Xaa
1               5                   10

<210> SEQ ID NO 127
<211> LENGTH: 15
<212> TYPE: PRT
<213> ORGANISM: Artificial
<220> FEATURE:
<223> OTHER INFORMATION: P14-40

<400> SEQUENCE: 127

Ser Glu Glu Glu Glu Glu Leu Met Gln Leu Leu Glu Asp Leu Val
1               5                   10                  15

<210> SEQ ID NO 128
<211> LENGTH: 15
<212> TYPE: PRT
<213> ORGANISM: Artificial
<220> FEATURE:
<223> OTHER INFORMATION: P14-41

<400> SEQUENCE: 128

Ser Glu Glu Glu Glu Glu Leu Leu Gln Leu Leu Glu Asp Leu Val
1               5                   10                  15

<210> SEQ ID NO 129
<211> LENGTH: 19
<212> TYPE: PRT
<213> ORGANISM: Artificial
<220> FEATURE:
<223> OTHER INFORMATION: P14-31

<400> SEQUENCE: 129

Ser Glu Glu Glu Glu Glu Ala Leu Glu Gln Leu Leu Glu Asp Leu Val
1               5                   10                  15

Lys Leu Leu

<210> SEQ ID NO 130
<211> LENGTH: 17
<212> TYPE: PRT
<213> ORGANISM: Artificial
<220> FEATURE:
<223> OTHER INFORMATION: P1-29

```
<400> SEQUENCE: 130

Asn Gln Gly Ile Ser Glu Lys Gln Leu Asp Gln Leu Leu Thr Gln Leu
1               5                   10                  15

Ile

<210> SEQ ID NO 131
<211> LENGTH: 14
<212> TYPE: PRT
<213> ORGANISM: Artificial
<220> FEATURE:
<223> OTHER INFORMATION: P1-31

<400> SEQUENCE: 131

Ser Glu Glu Glu Glu Leu Asp Gln Leu Leu Thr Gln Leu Ile
1               5                   10

<210> SEQ ID NO 132
<211> LENGTH: 17
<212> TYPE: PRT
<213> ORGANISM: Artificial
<220> FEATURE:
<223> OTHER INFORMATION: P4-111

<400> SEQUENCE: 132

Ser Gln Gly Ile Ser Glu Lys Gln Leu Asp Gln Leu Leu Ser Gln Leu
1               5                   10                  15

Ile

<210> SEQ ID NO 133
<211> LENGTH: 23
<212> TYPE: PRT
<213> ORGANISM: Artificial
<220> FEATURE:
<223> OTHER INFORMATION: P4-14S-13V

<400> SEQUENCE: 133

Ser Gln Gly Ile Ser Glu Lys Gln Leu Asp Gln Leu Val Ser Gln Leu
1               5                   10                  15

Ile Gln Ala Leu Leu Gln Pro
            20

<210> SEQ ID NO 134
<211> LENGTH: 23
<212> TYPE: PRT
<213> ORGANISM: Artificial
<220> FEATURE:
<223> OTHER INFORMATION: P4-14S-13F

<400> SEQUENCE: 134

Ser Gln Gly Ile Ser Glu Lys Gln Leu Asp Gln Leu Phe Ser Gln Leu
1               5                   10                  15

Ile Gln Ala Leu Leu Gln Pro
            20

<210> SEQ ID NO 135
<211> LENGTH: 23
<212> TYPE: PRT
<213> ORGANISM: Artificial
<220> FEATURE:
<223> OTHER INFORMATION: P4-14S-16V

<400> SEQUENCE: 135

Ser Gln Gly Ile Ser Glu Lys Gln Leu Asp Gln Leu Leu Ser Gln Val
1               5                   10                  15
```

Ile Gln Ala Leu Leu Gln Pro
            20

<210> SEQ ID NO 136
<211> LENGTH: 23
<212> TYPE: PRT
<213> ORGANISM: Artificial
<220> FEATURE:
<223> OTHER INFORMATION: P4-14S-17F

<400> SEQUENCE: 136

Ser Gln Gly Ile Ser Glu Lys Gln Leu Asp Gln Leu Leu Ser Gln Leu
1               5                   10                  15

Phe Gln Ala Leu Leu Gln Pro
            20

<210> SEQ ID NO 137
<211> LENGTH: 23
<212> TYPE: PRT
<213> ORGANISM: Artificial
<220> FEATURE:
<223> OTHER INFORMATION: P4-14S-20V

<400> SEQUENCE: 137

Ser Gln Gly Ile Ser Glu Lys Gln Leu Asp Gln Leu Leu Ser Gln Leu
1               5                   10                  15

Ile Gln Ala Val Leu Gln Pro
            20

<210> SEQ ID NO 138
<211> LENGTH: 23
<212> TYPE: PRT
<213> ORGANISM: Artificial
<220> FEATURE:
<223> OTHER INFORMATION: P4-14S-20F

<400> SEQUENCE: 138

Ser Gln Gly Ile Ser Glu Lys Gln Leu Asp Gln Leu Leu Ser Gln Leu
1               5                   10                  15

Ile Gln Ala Phe Leu Gln Pro
            20

<210> SEQ ID NO 139
<211> LENGTH: 14
<212> TYPE: PRT
<213> ORGANISM: Artificial
<220> FEATURE:
<223> OTHER INFORMATION: P4-115

<400> SEQUENCE: 139

Ser Glu Glu Glu Glu Leu Asp Gln Leu Leu Ser Gln Leu Ile
1               5                   10

<210> SEQ ID NO 140
<211> LENGTH: 16
<212> TYPE: PRT
<213> ORGANISM: Artificial
<220> FEATURE:
<223> OTHER INFORMATION: P4-116

<400> SEQUENCE: 140

Ser Gln Gly Ile Ser Glu Lys Gln Leu Asp Gln Leu Leu Ser Gln Leu
1               5                   10                  15

```
<210> SEQ ID NO 141
<211> LENGTH: 15
<212> TYPE: PRT
<213> ORGANISM: Artificial
<220> FEATURE:
<223> OTHER INFORMATION: P4-117

<400> SEQUENCE: 141

Ser Gln Gly Ile Ser Glu Lys Gln Leu Asp Gln Leu Leu Ser Gln
1               5                   10                  15

<210> SEQ ID NO 142
<211> LENGTH: 20
<212> TYPE: PRT
<213> ORGANISM: Artificial
<220> FEATURE:
<223> OTHER INFORMATION: P18-8

<400> SEQUENCE: 142

Gln Gln Pro Ile Asp Arg Gln Thr Ile Glu Gln Met Ala Gln Leu Leu
1               5                   10                  15

Ala Gln Leu Leu
            20

<210> SEQ ID NO 143
<211> LENGTH: 15
<212> TYPE: PRT
<213> ORGANISM: Artificial
<220> FEATURE:
<223> OTHER INFORMATION: P18-9

<400> SEQUENCE: 143

Ser Glu Glu Glu Glu Glu Leu Ala Gln Leu Leu Ala Gln Leu Leu
1               5                   10                  15

<210> SEQ ID NO 144
<211> LENGTH: 21
<212> TYPE: PRT
<213> ORGANISM: Artificial
<220> FEATURE:
<223> OTHER INFORMATION: P19-9

<400> SEQUENCE: 144

Ser Glu Glu Glu Glu Glu Ile Gly Asp Asn Pro Leu Leu Lys Ala Leu
1               5                   10                  15

Leu Lys Leu Ile Ala
            20

<210> SEQ ID NO 145
<211> LENGTH: 17
<212> TYPE: PRT
<213> ORGANISM: Artificial
<220> FEATURE:
<223> OTHER INFORMATION: P19-10

<400> SEQUENCE: 145

Ser Glu Glu Glu Glu Glu Glu Leu Leu Lys Ala Leu Leu Lys Leu Ile
1               5                   10                  15

Ala

<210> SEQ ID NO 146
<211> LENGTH: 17
<212> TYPE: PRT
<213> ORGANISM: Artificial
<220> FEATURE:
<223> OTHER INFORMATION: P19-12
```

```
<400> SEQUENCE: 146

Ser Glu Glu Glu Glu Glu Lys Ala Leu Leu Lys Leu Ile Ala Arg Leu
1               5                   10                  15

Leu

<210> SEQ ID NO 147
<211> LENGTH: 16
<212> TYPE: PRT
<213> ORGANISM: Artificial
<220> FEATURE:
<223> OTHER INFORMATION: P19-13

<400> SEQUENCE: 147

Ser Glu Glu Glu Glu Glu Ala Leu Leu Lys Leu Ile Ala Arg Leu Leu
1               5                   10                  15

<210> SEQ ID NO 148
<211> LENGTH: 17
<212> TYPE: PRT
<213> ORGANISM: Artificial
<220> FEATURE:
<223> OTHER INFORMATION: P15-62

<400> SEQUENCE: 148

Lys Pro Asn Asp Ser Gln Ser Asn Ile Ala Lys Leu Ile Ser Ala Leu
1               5                   10                  15

Ile

<210> SEQ ID NO 149
<211> LENGTH: 16
<212> TYPE: PRT
<213> ORGANISM: Artificial
<220> FEATURE:
<223> OTHER INFORMATION: P15-63

<400> SEQUENCE: 149

Ser Glu Glu Glu Glu Glu Ile Ala Lys Leu Ile Ser Ala Leu Ile
1               5                   10                  15

<210> SEQ ID NO 150
<211> LENGTH: 21
<212> TYPE: PRT
<213> ORGANISM: Artificial
<220> FEATURE:
<223> OTHER INFORMATION: P15-60

<400> SEQUENCE: 150

Ser Glu Glu Glu Glu Glu Glu Glu Ile Ala Lys Leu Ile Ser Ala Leu
1               5                   10                  15

Ile Glu Ser Leu Leu
            20

<210> SEQ ID NO 151
<211> LENGTH: 20
<212> TYPE: PRT
<213> ORGANISM: Artificial
<220> FEATURE:
<223> OTHER INFORMATION: P15-61

<400> SEQUENCE: 151

Ser Glu Glu Glu Glu Glu Glu Glu Ile Ala Lys Leu Ile Ser Leu Ile
1               5                   10                  15

Glu Ser Leu Leu
```

20

<210> SEQ ID NO 152
<211> LENGTH: 18
<212> TYPE: PRT
<213> ORGANISM: Artificial
<220> FEATURE:
<223> OTHER INFORMATION: P25-9

<400> SEQUENCE: 152

Ser Glu Glu Glu Glu Glu Leu Gln Lys Leu Leu Lys Ile Leu Glu Ala
1               5                   10                  15

Leu Val

<210> SEQ ID NO 153
<211> LENGTH: 19
<212> TYPE: PRT
<213> ORGANISM: Artificial
<220> FEATURE:
<223> OTHER INFORMATION: P25-12

<400> SEQUENCE: 153

Ser Glu Glu Glu Glu Glu Leu Thr Gly Val Leu Gln Lys Leu Leu Lys
1               5                   10                  15

Ile Leu Glu

<210> SEQ ID NO 154
<211> LENGTH: 21
<212> TYPE: PRT
<213> ORGANISM: Artificial
<220> FEATURE:
<223> OTHER INFORMATION: P25-13

<400> SEQUENCE: 154

Ser Glu Glu Glu Glu Glu Leu Thr Leu Thr Gly Val Leu Gln Lys Leu
1               5                   10                  15

Leu Lys Ile Leu Glu
            20

<210> SEQ ID NO 155
<211> LENGTH: 20
<212> TYPE: PRT
<213> ORGANISM: Artificial
<220> FEATURE:
<223> OTHER INFORMATION: P25-14

<400> SEQUENCE: 155

Ser Glu Glu Glu Glu Glu Leu Thr Leu Thr Gly Val Leu Gln Lys Leu
1               5                   10                  15

Leu Lys Ile Leu
            20

<210> SEQ ID NO 156
<211> LENGTH: 16
<212> TYPE: PRT
<213> ORGANISM: Artificial
<220> FEATURE:
<223> OTHER INFORMATION: P3-5

<400> SEQUENCE: 156

Ser Glu Glu Glu Leu Gln Gln Leu Leu Lys Leu Phe Ser Glu Ile Leu
1               5                   10                  15

<210> SEQ ID NO 157

```
<211> LENGTH: 20
<212> TYPE: PRT
<213> ORGANISM: Artificial
<220> FEATURE:
<223> OTHER INFORMATION: P3-8

<400> SEQUENCE: 157

Ser Glu Glu Glu Glu Glu Leu Leu Lys Leu Phe Ser Glu Ile Leu
1               5                   10                  15

Gln Ser Leu Phe
            20

<210> SEQ ID NO 158
<211> LENGTH: 20
<212> TYPE: PRT
<213> ORGANISM: Artificial
<220> FEATURE:
<223> OTHER INFORMATION: P3-9

<400> SEQUENCE: 158

Ser Glu Glu Glu Glu Gln Gln Leu Leu Lys Leu Phe Ser Glu Ile Leu
1               5                   10                  15

Gln Ser Leu Phe
            20

<210> SEQ ID NO 159
<211> LENGTH: 19
<212> TYPE: PRT
<213> ORGANISM: Artificial
<220> FEATURE:
<223> OTHER INFORMATION: P3-10

<400> SEQUENCE: 159

Ser Glu Glu Glu Glu Glu Leu Gln Gln Leu Leu Lys Leu Phe Ser Glu
1               5                   10                  15

Ile Leu Gln

<210> SEQ ID NO 160
<211> LENGTH: 15
<212> TYPE: PRT
<213> ORGANISM: Artificial
<220> FEATURE:
<223> OTHER INFORMATION: P14-39

<400> SEQUENCE: 160

Ser Glu Glu Glu Glu Glu Leu Glu Gln Leu Leu Glu Asp Leu Val
1               5                   10                  15

<210> SEQ ID NO 161
<211> LENGTH: 23
<212> TYPE: PRT
<213> ORGANISM: Artificial
<220> FEATURE:
<223> OTHER INFORMATION: P4-14S-16D

<400> SEQUENCE: 161

Ser Gln Gly Ile Ser Glu Lys Gln Leu Asp Gln Leu Leu Ser Gln Asp
1               5                   10                  15

Ile Gln Ala Leu Leu Gln Pro
            20

<210> SEQ ID NO 162
<211> LENGTH: 23
<212> TYPE: PRT
<213> ORGANISM: Artificial
```

```
<220> FEATURE:
<223> OTHER INFORMATION: P4-14S-20D

<400> SEQUENCE: 162

Ser Gln Gly Ile Ser Glu Lys Gln Leu Asp Gln Leu Leu Ser Gln Leu
1               5                   10                  15

Ile Gln Ala Asp Leu Gln Pro
            20

<210> SEQ ID NO 163
<211> LENGTH: 23
<212> TYPE: PRT
<213> ORGANISM: Artificial
<220> FEATURE:
<223> OTHER INFORMATION: P4-14S-13S

<400> SEQUENCE: 163

Ser Gln Gly Ile Ser Glu Lys Gln Leu Asp Gln Leu Ser Ser Gln Leu
1               5                   10                  15

Ile Gln Ala Leu Leu Gln Pro
            20

<210> SEQ ID NO 164
<211> LENGTH: 23
<212> TYPE: PRT
<213> ORGANISM: Artificial
<220> FEATURE:
<223> OTHER INFORMATION: P1-13P-20P

<400> SEQUENCE: 164

Asn Gln Gly Ile Ser Glu Lys Gln Leu Asp Gln Leu Pro Thr Gln Leu
1               5                   10                  15

Ile Met Ala Pro Leu Gln Gln
            20

<210> SEQ ID NO 165
<211> LENGTH: 23
<212> TYPE: PRT
<213> ORGANISM: Artificial
<220> FEATURE:
<223> OTHER INFORMATION: P1

<400> SEQUENCE: 165

Asn Gln Gly Ile Ser Glu Lys Gln Leu Asp Gln Leu Leu Thr Gln Leu
1               5                   10                  15

Ile Met Ala Leu Leu Gln Gln
            20

<210> SEQ ID NO 166
<211> LENGTH: 23
<212> TYPE: PRT
<213> ORGANISM: Artificial
<220> FEATURE:
<223> OTHER INFORMATION: P1-9D

<400> SEQUENCE: 166

Asn Gln Gly Ile Ser Glu Lys Gln Asp Asp Gln Leu Leu Thr Gln Leu
1               5                   10                  15

Ile Met Ala Leu Leu Gln Gln
            20

<210> SEQ ID NO 167
<211> LENGTH: 23
<212> TYPE: PRT
```

```
<213> ORGANISM: Artificial
<220> FEATURE:
<223> OTHER INFORMATION: P1-9S

<400> SEQUENCE: 167

Asn Gln Gly Ile Ser Glu Lys Gln Ser Asp Gln Leu Leu Thr Gln Leu
1               5                   10                  15

Ile Met Ala Leu Leu Gln Gln
            20

<210> SEQ ID NO 168
<211> LENGTH: 23
<212> TYPE: PRT
<213> ORGANISM: Artificial
<220> FEATURE:
<223> OTHER INFORMATION: P1-12D

<400> SEQUENCE: 168

Asn Gln Gly Ile Ser Glu Lys Gln Leu Asp Gln Asp Leu Thr Gln Leu
1               5                   10                  15

Ile Met Ala Leu Leu Gln Gln
            20

<210> SEQ ID NO 169
<211> LENGTH: 23
<212> TYPE: PRT
<213> ORGANISM: Artificial
<220> FEATURE:
<223> OTHER INFORMATION: P1-12S

<400> SEQUENCE: 169

Asn Gln Gly Ile Ser Glu Lys Gln Leu Asp Gln Ser Leu Thr Gln Leu
1               5                   10                  15

Ile Met Ala Leu Leu Gln Gln
            20

<210> SEQ ID NO 170
<211> LENGTH: 23
<212> TYPE: PRT
<213> ORGANISM: Artificial
<220> FEATURE:
<223> OTHER INFORMATION: P1-13D

<400> SEQUENCE: 170

Asn Gln Gly Ile Ser Glu Lys Gln Leu Asp Gln Leu Asp Thr Gln Leu
1               5                   10                  15

Ile Met Ala Leu Leu Gln Gln
            20

<210> SEQ ID NO 171
<211> LENGTH: 23
<212> TYPE: PRT
<213> ORGANISM: Artificial
<220> FEATURE:
<223> OTHER INFORMATION: P1-13S

<400> SEQUENCE: 171

Asn Gln Gly Ile Ser Glu Lys Gln Leu Asp Gln Leu Ser Thr Gln Leu
1               5                   10                  15

Ile Met Ala Leu Leu Gln Gln
            20

<210> SEQ ID NO 172
<211> LENGTH: 23
```

```
<212> TYPE: PRT
<213> ORGANISM: Artificial
<220> FEATURE:
<223> OTHER INFORMATION: P1-16D

<400> SEQUENCE: 172

Asn Gln Gly Ile Ser Glu Lys Gln Leu Asp Gln Leu Leu Thr Gln Asp
1               5                   10                  15

Ile Met Ala Leu Leu Gln Gln
            20

<210> SEQ ID NO 173
<211> LENGTH: 23
<212> TYPE: PRT
<213> ORGANISM: Artificial
<220> FEATURE:
<223> OTHER INFORMATION: P1-16S

<400> SEQUENCE: 173

Asn Gln Gly Ile Ser Glu Lys Gln Leu Asp Gln Leu Leu Thr Gln Ser
1               5                   10                  15

Ile Met Ala Leu Leu Gln Gln
            20

<210> SEQ ID NO 174
<211> LENGTH: 23
<212> TYPE: PRT
<213> ORGANISM: Artificial
<220> FEATURE:
<223> OTHER INFORMATION: P1-17D

<400> SEQUENCE: 174

Asn Gln Gly Ile Ser Glu Lys Gln Leu Asp Gln Leu Leu Thr Gln Leu
1               5                   10                  15

Asp Met Ala Leu Leu Gln Gln
            20

<210> SEQ ID NO 175
<211> LENGTH: 23
<212> TYPE: PRT
<213> ORGANISM: Artificial
<220> FEATURE:
<223> OTHER INFORMATION: P1-17S

<400> SEQUENCE: 175

Asn Gln Gly Ile Ser Glu Lys Gln Leu Asp Gln Leu Leu Thr Gln Leu
1               5                   10                  15

Ser Met Ala Leu Leu Gln Gln
            20

<210> SEQ ID NO 176
<211> LENGTH: 23
<212> TYPE: PRT
<213> ORGANISM: Artificial
<220> FEATURE:
<223> OTHER INFORMATION: P1-20D

<400> SEQUENCE: 176

Asn Gln Gly Ile Ser Glu Lys Gln Leu Asp Gln Leu Leu Thr Gln Leu
1               5                   10                  15

Ile Met Ala Asp Leu Gln Gln
            20

<210> SEQ ID NO 177
```

```
<211> LENGTH: 23
<212> TYPE: PRT
<213> ORGANISM: Artificial
<220> FEATURE:
<223> OTHER INFORMATION: P1-20S

<400> SEQUENCE: 177

Asn Gln Gly Ile Ser Glu Lys Gln Leu Asp Gln Leu Leu Thr Gln Leu
1               5                   10                  15

Ile Met Ala Ser Leu Gln Gln
            20

<210> SEQ ID NO 178
<211> LENGTH: 23
<212> TYPE: PRT
<213> ORGANISM: Artificial
<220> FEATURE:
<223> OTHER INFORMATION: P1-21D

<400> SEQUENCE: 178

Asn Gln Gly Ile Ser Glu Lys Gln Leu Asp Gln Leu Leu Thr Gln Leu
1               5                   10                  15

Ile Met Ala Leu Asp Gln Gln
            20

<210> SEQ ID NO 179
<211> LENGTH: 23
<212> TYPE: PRT
<213> ORGANISM: Artificial
<220> FEATURE:
<223> OTHER INFORMATION: P1-21S

<400> SEQUENCE: 179

Asn Gln Gly Ile Ser Glu Lys Gln Leu Asp Gln Leu Leu Thr Gln Leu
1               5                   10                  15

Ile Met Ala Leu Ser Gln Gln
            20

<210> SEQ ID NO 180
<211> LENGTH: 22
<212> TYPE: PRT
<213> ORGANISM: Artificial
<220> FEATURE:
<223> OTHER INFORMATION: P15b-9D

<400> SEQUENCE: 180

Lys Pro Asn Asp Ser Gln Ser Asn Asp Ala Lys Leu Ile Ser Ala Leu
1               5                   10                  15

Ile Met Ser Leu Leu Gln
            20

<210> SEQ ID NO 181
<211> LENGTH: 22
<212> TYPE: PRT
<213> ORGANISM: Artificial
<220> FEATURE:
<223> OTHER INFORMATION: P15b-12D

<400> SEQUENCE: 181

Lys Pro Asn Asp Ser Gln Ser Asn Ile Ala Lys Asp Ile Ser Ala Leu
1               5                   10                  15

Ile Met Ser Leu Leu Gln
            20
```

```
<210> SEQ ID NO 182
<211> LENGTH: 22
<212> TYPE: PRT
<213> ORGANISM: Artificial
<220> FEATURE:
<223> OTHER INFORMATION: P15b-13D

<400> SEQUENCE: 182

Lys Pro Asn Asp Ser Gln Ser Asn Ile Ala Lys Leu Asp Ser Ala Leu
1               5                   10                  15

Ile Met Ser Leu Leu Gln
            20

<210> SEQ ID NO 183
<211> LENGTH: 22
<212> TYPE: PRT
<213> ORGANISM: Artificial
<220> FEATURE:
<223> OTHER INFORMATION: P15b-16D

<400> SEQUENCE: 183

Lys Pro Asn Asp Ser Gln Ser Asn Ile Ala Lys Leu Ile Ser Ala Asp
1               5                   10                  15

Ile Met Ser Leu Leu Gln
            20

<210> SEQ ID NO 184
<211> LENGTH: 22
<212> TYPE: PRT
<213> ORGANISM: Artificial
<220> FEATURE:
<223> OTHER INFORMATION: P15b-17D

<400> SEQUENCE: 184

Lys Pro Asn Asp Ser Gln Ser Asn Ile Ala Lys Leu Ile Ser Ala Leu
1               5                   10                  15

Asp Met Ser Leu Leu Gln
            20

<210> SEQ ID NO 185
<211> LENGTH: 22
<212> TYPE: PRT
<213> ORGANISM: Artificial
<220> FEATURE:
<223> OTHER INFORMATION: P15b-20D

<400> SEQUENCE: 185

Lys Pro Asn Asp Ser Gln Ser Asn Ile Ala Lys Leu Ile Ser Ala Leu
1               5                   10                  15

Ile Met Ser Asp Leu Gln
            20

<210> SEQ ID NO 186
<211> LENGTH: 22
<212> TYPE: PRT
<213> ORGANISM: Artificial
<220> FEATURE:
<223> OTHER INFORMATION: P15b-21D

<400> SEQUENCE: 186

Lys Pro Asn Asp Ser Gln Ser Asn Ile Ala Lys Leu Ile Ser Ala Leu
1               5                   10                  15

Ile Met Ser Leu Asp Gln
            20
```

<210> SEQ ID NO 187
<211> LENGTH: 22
<212> TYPE: PRT
<213> ORGANISM: Artificial
<220> FEATURE:
<223> OTHER INFORMATION: P15b-9S

<400> SEQUENCE: 187

Lys Pro Asn Asp Ser Gln Ser Asn Ser Ala Lys Leu Ile Ser Ala Leu
1               5                   10                  15

Ile Met Ser Leu Leu Gln
            20

<210> SEQ ID NO 188
<211> LENGTH: 22
<212> TYPE: PRT
<213> ORGANISM: Artificial
<220> FEATURE:
<223> OTHER INFORMATION: P15b-12S

<400> SEQUENCE: 188

Lys Pro Asn Asp Ser Gln Ser Asn Ile Ala Lys Ser Ile Ser Ala Leu
1               5                   10                  15

Ile Met Ser Leu Leu Gln
            20

<210> SEQ ID NO 189
<211> LENGTH: 22
<212> TYPE: PRT
<213> ORGANISM: Artificial
<220> FEATURE:
<223> OTHER INFORMATION: P15b-13S

<400> SEQUENCE: 189

Lys Pro Asn Asp Ser Gln Ser Asn Ile Ala Lys Leu Ser Ser Ala Leu
1               5                   10                  15

Ile Met Ser Leu Leu Gln
            20

<210> SEQ ID NO 190
<211> LENGTH: 22
<212> TYPE: PRT
<213> ORGANISM: Artificial
<220> FEATURE:
<223> OTHER INFORMATION: P15b-16S

<400> SEQUENCE: 190

Lys Pro Asn Asp Ser Gln Ser Asn Ile Ala Lys Leu Ile Ser Ala Ser
1               5                   10                  15

Ile Met Ser Leu Leu Gln
            20

<210> SEQ ID NO 191
<211> LENGTH: 22
<212> TYPE: PRT
<213> ORGANISM: Artificial
<220> FEATURE:
<223> OTHER INFORMATION: P15b-17S

<400> SEQUENCE: 191

Lys Pro Asn Asp Ser Gln Ser Asn Ile Ala Lys Leu Ile Ser Ala Leu
1               5                   10                  15

Ser Met Ser Leu Leu Gln
            20

```
<210> SEQ ID NO 192
<211> LENGTH: 22
<212> TYPE: PRT
<213> ORGANISM: Artificial
<220> FEATURE:
<223> OTHER INFORMATION: P15b-20S

<400> SEQUENCE: 192

Lys Pro Asn Asp Ser Gln Ser Asn Ile Ala Lys Leu Ile Ser Ala Leu
1               5                   10                  15

Ile Met Ser Ser Leu Gln
            20

<210> SEQ ID NO 193
<211> LENGTH: 22
<212> TYPE: PRT
<213> ORGANISM: Artificial
<220> FEATURE:
<223> OTHER INFORMATION: P15b-21S

<400> SEQUENCE: 193

Lys Pro Asn Asp Ser Gln Ser Asn Ile Ala Lys Leu Ile Ser Ala Leu
1               5                   10                  15

Ile Met Ser Leu Ser Gln
            20

<210> SEQ ID NO 194
<211> LENGTH: 20
<212> TYPE: PRT
<213> ORGANISM: Artificial
<220> FEATURE:
<223> OTHER INFORMATION: P6a-4D

<400> SEQUENCE: 194

Pro Ser Pro Asp Thr Gln Met Leu Met His Ile Val Gly Glu Ile Leu
1               5                   10                  15

Gln Ala Gln Asn
            20

<210> SEQ ID NO 195
<211> LENGTH: 20
<212> TYPE: PRT
<213> ORGANISM: Artificial
<220> FEATURE:
<223> OTHER INFORMATION: P6a-7D

<400> SEQUENCE: 195

Pro Ser Pro Phe Thr Gln Asp Leu Met His Ile Val Gly Glu Ile Leu
1               5                   10                  15

Gln Ala Gln Asn
            20

<210> SEQ ID NO 196
<211> LENGTH: 20
<212> TYPE: PRT
<213> ORGANISM: Artificial
<220> FEATURE:
<223> OTHER INFORMATION: P6a-8D

<400> SEQUENCE: 196

Pro Ser Pro Phe Thr Gln Met Asp Met His Ile Val Gly Glu Ile Leu
1               5                   10                  15

Gln Ala Gln Asn
```

```
                        20

<210> SEQ ID NO 197
<211> LENGTH: 20
<212> TYPE: PRT
<213> ORGANISM: Artificial
<220> FEATURE:
<223> OTHER INFORMATION: P6a-11D

<400> SEQUENCE: 197

Pro Ser Pro Phe Thr Gln Met Leu Met His Asp Val Gly Glu Ile Leu
1               5                   10                  15

Gln Ala Gln Asn
            20

<210> SEQ ID NO 198
<211> LENGTH: 20
<212> TYPE: PRT
<213> ORGANISM: Artificial
<220> FEATURE:
<223> OTHER INFORMATION: P6a-12D

<400> SEQUENCE: 198

Pro Ser Pro Phe Thr Gln Met Leu Met His Ile Asp Gly Glu Ile Leu
1               5                   10                  15

Gln Ala Gln Asn
            20

<210> SEQ ID NO 199
<211> LENGTH: 20
<212> TYPE: PRT
<213> ORGANISM: Artificial
<220> FEATURE:
<223> OTHER INFORMATION: P6a-15D

<400> SEQUENCE: 199

Pro Ser Pro Phe Thr Gln Met Leu Met His Ile Val Gly Glu Asp Leu
1               5                   10                  15

Gln Ala Gln Asn
            20

<210> SEQ ID NO 200
<211> LENGTH: 20
<212> TYPE: PRT
<213> ORGANISM: Artificial
<220> FEATURE:
<223> OTHER INFORMATION: P6a-16D

<400> SEQUENCE: 200

Pro Ser Pro Phe Thr Gln Met Leu Met His Ile Val Gly Glu Ile Asp
1               5                   10                  15

Gln Ala Gln Asn
            20

<210> SEQ ID NO 201
<211> LENGTH: 20
<212> TYPE: PRT
<213> ORGANISM: Artificial
<220> FEATURE:
<223> OTHER INFORMATION: P6a-4S

<400> SEQUENCE: 201

Pro Ser Pro Ser Thr Gln Met Leu Met His Ile Val Gly Glu Ile Leu
1               5                   10                  15
```

-continued

Gln Ala Gln Asn
            20

<210> SEQ ID NO 202
<211> LENGTH: 20
<212> TYPE: PRT
<213> ORGANISM: Artificial
<220> FEATURE:
<223> OTHER INFORMATION: P6a-7S

<400> SEQUENCE: 202

Pro Ser Pro Phe Thr Gln Ser Leu Met His Ile Val Gly Glu Ile Leu
1               5                   10                  15

Gln Ala Gln Asn
            20

<210> SEQ ID NO 203
<211> LENGTH: 20
<212> TYPE: PRT
<213> ORGANISM: Artificial
<220> FEATURE:
<223> OTHER INFORMATION: P6a-8S

<400> SEQUENCE: 203

Pro Ser Pro Phe Thr Gln Met Ser Met His Ile Val Gly Glu Ile Leu
1               5                   10                  15

Gln Ala Gln Asn
            20

<210> SEQ ID NO 204
<211> LENGTH: 20
<212> TYPE: PRT
<213> ORGANISM: Artificial
<220> FEATURE:
<223> OTHER INFORMATION: P6a-11S

<400> SEQUENCE: 204

Pro Ser Pro Phe Thr Gln Met Leu Met His Ser Val Gly Glu Ile Leu
1               5                   10                  15

Gln Ala Gln Asn
            20

<210> SEQ ID NO 205
<211> LENGTH: 20
<212> TYPE: PRT
<213> ORGANISM: Artificial
<220> FEATURE:
<223> OTHER INFORMATION: P6a-12S

<400> SEQUENCE: 205

Pro Ser Pro Phe Thr Gln Met Leu Met His Ile Ser Gly Glu Ile Leu
1               5                   10                  15

Gln Ala Gln Asn
            20

<210> SEQ ID NO 206
<211> LENGTH: 20
<212> TYPE: PRT
<213> ORGANISM: Artificial
<220> FEATURE:
<223> OTHER INFORMATION: P6a-15S

<400> SEQUENCE: 206

Pro Ser Pro Phe Thr Gln Met Leu Met His Ile Val Gly Glu Ser Leu
1               5                   10                  15

Gln Ala Gln Asn
            20

<210> SEQ ID NO 207
<211> LENGTH: 20
<212> TYPE: PRT
<213> ORGANISM: Artificial
<220> FEATURE:
<223> OTHER INFORMATION: P6a-16S

<400> SEQUENCE: 207

Pro Ser Pro Phe Thr Gln Met Leu Met His Ile Val Gly Glu Ile Ser
1               5                   10                  15

Gln Ala Gln Asn
            20

<210> SEQ ID NO 208
<211> LENGTH: 19
<212> TYPE: PRT
<213> ORGANISM: Artificial
<220> FEATURE:
<223> OTHER INFORMATION: P14d-7D

<400> SEQUENCE: 208

Gln Asp Pro Met Gln Ala Asp Met Gln Leu Leu Glu Asp Leu Val Lys
1               5                   10                  15

Leu Leu Lys

<210> SEQ ID NO 209
<211> LENGTH: 19
<212> TYPE: PRT
<213> ORGANISM: Artificial
<220> FEATURE:
<223> OTHER INFORMATION: P14d-10D

<400> SEQUENCE: 209

Gln Asp Pro Met Gln Ala Leu Met Gln Asp Leu Glu Asp Leu Val Lys
1               5                   10                  15

Leu Leu Lys

<210> SEQ ID NO 210
<211> LENGTH: 19
<212> TYPE: PRT
<213> ORGANISM: Artificial
<220> FEATURE:
<223> OTHER INFORMATION: P14d-11D

<400> SEQUENCE: 210

Gln Asp Pro Met Gln Ala Leu Met Gln Leu Asp Glu Asp Leu Val Lys
1               5                   10                  15

Leu Leu Lys

<210> SEQ ID NO 211
<211> LENGTH: 20
<212> TYPE: PRT
<213> ORGANISM: Artificial
<220> FEATURE:
<223> OTHER INFORMATION: P14d-14D

<400> SEQUENCE: 211

Gln Asp Pro Met Gln Ala Leu Met Gln Leu Leu Glu Asp Asp Val Lys
1               5                   10                  15

Leu Leu Lys Lys

```
<210> SEQ ID NO 212
<211> LENGTH: 19
<212> TYPE: PRT
<213> ORGANISM: Artificial
<220> FEATURE:
<223> OTHER INFORMATION: P14d-15D

<400> SEQUENCE: 212

Gln Asp Pro Met Gln Ala Leu Met Gln Leu Leu Glu Asp Leu Asp Lys
1               5                   10                  15

Leu Leu Lys

<210> SEQ ID NO 213
<211> LENGTH: 19
<212> TYPE: PRT
<213> ORGANISM: Artificial
<220> FEATURE:
<223> OTHER INFORMATION: P14d-17D

<400> SEQUENCE: 213

Gln Asp Pro Met Gln Ala Leu Met Gln Leu Leu Glu Asp Leu Val Lys
1               5                   10                  15

Asp Leu Lys

<210> SEQ ID NO 214
<211> LENGTH: 19
<212> TYPE: PRT
<213> ORGANISM: Artificial
<220> FEATURE:
<223> OTHER INFORMATION: P14d-18D

<400> SEQUENCE: 214

Gln Asp Pro Met Gln Ala Leu Met Gln Leu Leu Glu Asp Leu Val Lys
1               5                   10                  15

Leu Asp Lys

<210> SEQ ID NO 215
<211> LENGTH: 19
<212> TYPE: PRT
<213> ORGANISM: Artificial
<220> FEATURE:
<223> OTHER INFORMATION: P14d-7S

<400> SEQUENCE: 215

Gln Asp Pro Met Gln Ala Ser Met Gln Leu Leu Glu Asp Leu Val Lys
1               5                   10                  15

Leu Leu Lys

<210> SEQ ID NO 216
<211> LENGTH: 19
<212> TYPE: PRT
<213> ORGANISM: Artificial
<220> FEATURE:
<223> OTHER INFORMATION: P14d-10S

<400> SEQUENCE: 216

Gln Asp Pro Met Gln Ala Leu Met Gln Ser Leu Glu Asp Leu Val Lys
1               5                   10                  15

Leu Leu Lys

<210> SEQ ID NO 217
```

```
<211> LENGTH: 19
<212> TYPE: PRT
<213> ORGANISM: Artificial
<220> FEATURE:
<223> OTHER INFORMATION: P14d-11S

<400> SEQUENCE: 217

Gln Asp Pro Met Gln Ala Leu Met Gln Leu Ser Glu Asp Leu Val Lys
1               5                   10                  15

Leu Leu Lys

<210> SEQ ID NO 218
<211> LENGTH: 19
<212> TYPE: PRT
<213> ORGANISM: Artificial
<220> FEATURE:
<223> OTHER INFORMATION: P14d-14S

<400> SEQUENCE: 218

Gln Asp Pro Met Gln Ala Leu Met Gln Leu Leu Glu Asp Ser Val Lys
1               5                   10                  15

Leu Leu Lys

<210> SEQ ID NO 219
<211> LENGTH: 19
<212> TYPE: PRT
<213> ORGANISM: Artificial
<220> FEATURE:
<223> OTHER INFORMATION: P14d-15S

<400> SEQUENCE: 219

Gln Asp Pro Met Gln Ala Leu Met Gln Leu Leu Glu Asp Leu Ser Lys
1               5                   10                  15

Leu Leu Lys

<210> SEQ ID NO 220
<211> LENGTH: 19
<212> TYPE: PRT
<213> ORGANISM: Artificial
<220> FEATURE:
<223> OTHER INFORMATION: P14d-17S

<400> SEQUENCE: 220

Gln Asp Pro Met Gln Ala Leu Met Gln Leu Leu Glu Asp Leu Val Lys
1               5                   10                  15

Ser Leu Lys

<210> SEQ ID NO 221
<211> LENGTH: 19
<212> TYPE: PRT
<213> ORGANISM: Artificial
<220> FEATURE:
<223> OTHER INFORMATION: P14d-18S

<400> SEQUENCE: 221

Gln Asp Pro Met Gln Ala Leu Met Gln Leu Leu Glu Asp Leu Val Lys
1               5                   10                  15

Leu Ser Lys

<210> SEQ ID NO 222
<211> LENGTH: 21
<212> TYPE: PRT
<213> ORGANISM: Artificial
<220> FEATURE:
```

<223> OTHER INFORMATION: P25-5D

<400> SEQUENCE: 222

Gly Gly Leu Thr Asp Thr Gly Val Leu Gln Lys Leu Met Lys Ile Leu
1               5                   10                  15

Asn Ala Leu Val Gln
            20

<210> SEQ ID NO 223
<211> LENGTH: 21
<212> TYPE: PRT
<213> ORGANISM: Artificial
<220> FEATURE:
<223> OTHER INFORMATION: P25-8D

<400> SEQUENCE: 223

Gly Gly Leu Thr Leu Thr Gly Asp Leu Gln Lys Leu Met Lys Ile Leu
1               5                   10                  15

Asn Ala Leu Val Gln
            20

<210> SEQ ID NO 224
<211> LENGTH: 21
<212> TYPE: PRT
<213> ORGANISM: Artificial
<220> FEATURE:
<223> OTHER INFORMATION: P25-9D

<400> SEQUENCE: 224

Gly Gly Leu Thr Leu Thr Gly Val Asp Gln Lys Leu Met Lys Ile Leu
1               5                   10                  15

Asn Ala Leu Val Gln
            20

<210> SEQ ID NO 225
<211> LENGTH: 21
<212> TYPE: PRT
<213> ORGANISM: Artificial
<220> FEATURE:
<223> OTHER INFORMATION: P25-12D

<400> SEQUENCE: 225

Gly Gly Leu Thr Leu Thr Gly Val Leu Gln Lys Asp Met Lys Ile Leu
1               5                   10                  15

Asn Ala Leu Val Gln
            20

<210> SEQ ID NO 226
<211> LENGTH: 21
<212> TYPE: PRT
<213> ORGANISM: Artificial
<220> FEATURE:
<223> OTHER INFORMATION: P25-13D

<400> SEQUENCE: 226

Gly Gly Leu Thr Leu Thr Gly Val Leu Gln Lys Leu Asp Lys Ile Leu
1               5                   10                  15

Asn Ala Leu Val Gln
            20

<210> SEQ ID NO 227
<211> LENGTH: 21
<212> TYPE: PRT
<213> ORGANISM: Artificial

<220> FEATURE:
<223> OTHER INFORMATION: P25-15D

<400> SEQUENCE: 227

Gly Gly Leu Thr Leu Thr Gly Val Leu Gln Lys Leu Met Lys Asp Leu
1               5                   10                  15

Asn Ala Leu Val Gln
            20

<210> SEQ ID NO 228
<211> LENGTH: 21
<212> TYPE: PRT
<213> ORGANISM: Artificial
<220> FEATURE:
<223> OTHER INFORMATION: P25-16D

<400> SEQUENCE: 228

Gly Gly Leu Thr Leu Thr Gly Val Leu Gln Lys Leu Met Lys Ile Asp
1               5                   10                  15

Asn Ala Leu Val Gln
            20

<210> SEQ ID NO 229
<211> LENGTH: 21
<212> TYPE: PRT
<213> ORGANISM: Artificial
<220> FEATURE:
<223> OTHER INFORMATION: P25-19D

<400> SEQUENCE: 229

Gly Gly Leu Thr Leu Thr Gly Val Leu Gln Lys Leu Met Lys Ile Leu
1               5                   10                  15

Asn Ala Asp Val Gln
            20

<210> SEQ ID NO 230
<211> LENGTH: 21
<212> TYPE: PRT
<213> ORGANISM: Artificial
<220> FEATURE:
<223> OTHER INFORMATION: P25-20D

<400> SEQUENCE: 230

Gly Gly Leu Thr Leu Thr Gly Val Leu Gln Lys Leu Met Lys Ile Leu
1               5                   10                  15

Asn Ala Leu Asp Gln
            20

<210> SEQ ID NO 231
<211> LENGTH: 21
<212> TYPE: PRT
<213> ORGANISM: Artificial
<220> FEATURE:
<223> OTHER INFORMATION: P25-5S

<400> SEQUENCE: 231

Gly Gly Leu Thr Ser Thr Gly Val Leu Gln Lys Leu Met Lys Ile Leu
1               5                   10                  15

Asn Ala Leu Val Gln
            20

<210> SEQ ID NO 232
<211> LENGTH: 21
<212> TYPE: PRT

```
<213> ORGANISM: Artificial
<220> FEATURE:
<223> OTHER INFORMATION: P25-8S

<400> SEQUENCE: 232

Gly Gly Leu Thr Leu Thr Gly Ser Leu Gln Lys Leu Met Lys Ile Leu
1               5                   10                  15

Asn Ala Leu Val Gln
            20

<210> SEQ ID NO 233
<211> LENGTH: 21
<212> TYPE: PRT
<213> ORGANISM: Artificial
<220> FEATURE:
<223> OTHER INFORMATION: P25-9S

<400> SEQUENCE: 233

Gly Gly Leu Thr Leu Thr Gly Val Ser Gln Lys Leu Met Lys Ile Leu
1               5                   10                  15

Asn Ala Leu Val Gln
            20

<210> SEQ ID NO 234
<211> LENGTH: 21
<212> TYPE: PRT
<213> ORGANISM: Artificial
<220> FEATURE:
<223> OTHER INFORMATION: P25-12S

<400> SEQUENCE: 234

Gly Gly Leu Thr Leu Thr Gly Val Leu Gln Lys Ser Met Lys Ile Leu
1               5                   10                  15

Asn Ala Leu Val Gln
            20

<210> SEQ ID NO 235
<211> LENGTH: 21
<212> TYPE: PRT
<213> ORGANISM: Artificial
<220> FEATURE:
<223> OTHER INFORMATION: P25-13S

<400> SEQUENCE: 235

Gly Gly Leu Thr Leu Thr Gly Val Leu Gln Lys Leu Ser Lys Ile Leu
1               5                   10                  15

Asn Ala Leu Val Gln
            20

<210> SEQ ID NO 236
<211> LENGTH: 21
<212> TYPE: PRT
<213> ORGANISM: Artificial
<220> FEATURE:
<223> OTHER INFORMATION: P25-15S

<400> SEQUENCE: 236

Gly Gly Leu Thr Leu Thr Gly Val Leu Gln Lys Leu Met Lys Ser Leu
1               5                   10                  15

Asn Ala Leu Val Gln
            20

<210> SEQ ID NO 237
<211> LENGTH: 21
```

```
<212> TYPE: PRT
<213> ORGANISM: Artificial
<220> FEATURE:
<223> OTHER INFORMATION: P25-16S

<400> SEQUENCE: 237

Gly Gly Leu Thr Leu Thr Gly Val Leu Gln Lys Leu Met Lys Ile Ser
1               5                   10                  15

Asn Ala Leu Val Gln
            20

<210> SEQ ID NO 238
<211> LENGTH: 21
<212> TYPE: PRT
<213> ORGANISM: Artificial
<220> FEATURE:
<223> OTHER INFORMATION: P25-19S

<400> SEQUENCE: 238

Gly Gly Leu Thr Leu Thr Gly Val Leu Gln Lys Leu Met Lys Ile Leu
1               5                   10                  15

Asn Ala Ser Val Gln
            20

<210> SEQ ID NO 239
<211> LENGTH: 21
<212> TYPE: PRT
<213> ORGANISM: Artificial
<220> FEATURE:
<223> OTHER INFORMATION: P25-20S

<400> SEQUENCE: 239

Gly Gly Leu Thr Leu Thr Gly Val Leu Gln Lys Leu Met Lys Ile Leu
1               5                   10                  15

Asn Ala Leu Ser Gln
            20

<210> SEQ ID NO 240
<211> LENGTH: 99
<212> TYPE: DNA
<213> ORGANISM: Artificial
<220> FEATURE:
<223> OTHER INFORMATION: P14 A. thaliana

<400> SEQUENCE: 240
caagctggac ctcaatctgc taataagact ggaaatgttg atgatgctaa taatcaagat    60
cctatgcaag ctcttatgca acttcttgaa gatcttgtt                          99

<210> SEQ ID NO 241
<211> LENGTH: 99
<212> TYPE: DNA
<213> ORGANISM: Artificial
<220> FEATURE:
<223> OTHER INFORMATION: P14 e.coli

<400> SEQUENCE: 241
caggcaggtc cgcagagcgc aaataaaacc ggtaatgttg atgatgcaaa taatcaggat    60
ccgatgcagg cactgatgca gctgctggaa gatctggtt                          99

<210> SEQ ID NO 242
<211> LENGTH: 57
<212> TYPE: DNA
<213> ORGANISM: Artificial
<220> FEATURE:
```

```
<223> OTHER INFORMATION: P14d-10D A. thaliana

<400> SEQUENCE: 242
caagatccta tgcaagctct tatgcaagat cttgaagatc ttgttaagct tcttaag         57

<210> SEQ ID NO 243
<211> LENGTH: 57
<212> TYPE: DNA
<213> ORGANISM: Artificial
<220> FEATURE:
<223> OTHER INFORMATION: P14d-10D e.coli

<400> SEQUENCE: 243
caggatccga tgcaggcact gatgcaggat ctggaagatc tggttaaact gctgaaa         57
```

ELICITOR PEPTIDES HAVING DISRUPTED HYPERSENSITIVE RESPONSE BOX AND USE THEREOF

This application is a continuation of U.S. patent application Ser. No. 15/244,862, filed Aug. 23, 2016, which is a continuation of U.S. patent application Ser. No. 14/872,347, filed Oct. 1, 2015, and issued as U.S. Pat. No. 10,743,538, which claims the priority benefit of U.S. Provisional Patent Application Ser. No. 62/058,535, filed Oct. 1, 2014, and U.S. Provisional Patent Application Ser. No. 62/186,527, filed Jun. 30, 2015, each of which is hereby incorporated by reference in its entirety.

FIELD OF THE INVENTION

The present invention relates to novel elicitor peptides having disrupted hypersensitive response boxes and their use for inducing active plant responses including, among others, growth enhancement, disease resistance, pest or insect resistance, and stress resistance.

BACKGROUND OF THE INVENTION

The identification and isolation of harpin proteins came from basic research at Cornell University attempting to understand how plant pathogenic bacteria interact with plants. A first line of defense is the hypersensitive response (HR), a localized plant cell death at the site of infection. Cell death creates a physical barrier to movement of the pathogen and in some plants dead cells can release compounds toxic to the invading pathogen. Research had indicated that pathogenic bacteria were likely to have a single factor that was responsible for triggering the HR. A basic aim of the Cornell research was to identify a specific bacterial protein responsible for eliciting the HR. The target protein was known to be encoded by one of a group of bacteria genes called the Hypersensitive Response and Pathogenicity (hrp) gene cluster. The hrp cluster in the bacterium *Erwinia amylovora* (Ea), which causes fire blight in pear and apple, was dissected and a single protein was identified that elicited HR in certain plants. This protein was given the name harpin (and, later, harpin$_{Ea}$) and the corresponding gene designated hrpN. This was the first example of such a protein and gene identified from any bacterial species.

A number of different harpin proteins have since been identified from *Erwinia*, *Pseudomonas*, *Ralstonia*, *Xanthomonas*, and *Pantoea* species, among others. Harpin proteins, while diverse at the primary amino acid sequence level, share common biochemical and biophysical characteristics as well as biological functions. Based on their unique properties, the harpin proteins are regarded in the literature as belonging to a single class of proteins.

Subsequent to their identification and isolation, it was thereafter discovered that harpins could elicit disease resistance in plants and increase plant growth. An important early finding was that application of purified harpin protein made a plant resistant to a subsequent pathogen attack, and in locations on the plant well away from the injection site. This meant that harpin proteins can trigger a Systemic Acquired Resistance (SAR), a plant defense mechanism that provides resistance to a variety of viral, bacterial, and fungal pathogens.

In crop protection, there is a continuous need for compositions that improve the health of plants. Healthier plants are desirable since they result in better yields and/or a better quality of the plants or crops. Healthier plants also better resist biotic and abiotic stress. A high resistance against biotic stresses in turn allows the growers to reduce the quantity of pesticides applied and consequently to slow down the development of resistances against the respective pesticides.

Harpin$_{\alpha\beta}$ is a fusion protein that is derived from several different harpins. Harpin$_{\alpha\beta}$ has been shown to suppress nematode egg production, enhance the growth, quality and yield of a plant, and increase a plant's vigor. Its amino acid and nucleotide sequences are described in detail in U.S. Application Publ. No. 2010/0043095.

To date, harpin and harpin$_{\alpha\beta}$ production and their use in agricultural and horticultural applications have been as a powdered solid coated on starch. This limits the use and versatility of the harpin proteins, because liquid suspensions of the powdered harpin proteins in water have an effective useful life of only 48-72 hours before significant degradation and loss of activity occurs. Another problem with harpin solutions is protein solubility and stability.

It would be desirable to identify synthetic and derivative harpin peptides that are readily soluble in aqueous solution, stable, resistant to chemical degradation, and effective in inducing active plant responses that include, among others, enhanced plant growth and production, as well as resistance to abiotic and biotic stressors.

The present invention is directed to overcoming these and other limitations in the art.

SUMMARY OF THE INVENTION

A first aspect of the invention relates to an isolated peptide comprising the amino acid sequence of:

J-X-X-X-J-J-X-X-X-J-J-X-X-X-J-J    (SEQ ID NO: 1) wherein the peptide is free of cysteine and methionine;
each X at positions 2, 3, 7, 8, 12, and 13 is optional and, when present, is any amino acid;
each X at positions 4, 9, and 14 is any amino acid;
one to three of the J residues at positions 1, 5, 6, 10, 11, 15, and 16 is a non-hydrophobic amino acid or A, and all other of the J residues are L, I, V, or F, and the peptide induces an active plant response, but does not induce a hypersensitive response, when applied to plant tissue.

A second aspect of the invention relates to an isolated peptide having the amino acid sequence of:

XXGISEKXXXXX XXXXXXXXXXX    (SEQ ID NO: 2, modified P1/P4 consensus), wherein

X at position 1 is optional and can be S, N, D, isoD, G, A, or S;
X at position 2 is optional and can be Q, E, g-glutamate, G, A, or S;
X at position 8 is Q, E, g-glutamate, G, A, or S;
X at position 9 is M, L, I, F, or V, or a non-hydrophobic amino acid;
X at position 10 is optional and can be D or isoD;
X at position 11 is Q, E, g-glutamate, G, A, or S;
X at position 12 is M, L, I, or F, or a non-hydrophobic amino acid;
X at position 13 is M, L, or I, or a non-hydrophobic amino acid;
X at position 14 is optional and can be any hydrophilic amino acid, preferably S, T, D, isoD, K, or Q, and optionally A or C;
X at position 15 is Q, E, g-glutamate, G, A, S, K, or I;
X at position 16 is M, L, I, V, or F, or a non-hydrophobic amino acid;
X at position 17 is M, L, I, A, or V, or a non-hydrophobic amino acid;

X at position 18 is Q, E, g-glutamate, G, A, S, M, T, or K;
X at position 19 is A, D, isoD, S, V, T, K, R, E, H, or G;
X at position 20 is M, L, or I;
X at position 21 is M, L, I, V, S, or F, or a non-hydrophobic amino acid other than serine;
X at position 22 is Q, E, g-glutamate, G, A, S;
X at position 23 is P, Q, E, g-glutamate, G, A, or S; and
wherein at least one of the residues at positions 9, 12, 13, 16, 17, and 20 is a non-hydrophobic amino acid, or the residue at position 21 is a non-hydrophobic amino acid other than serine; and
wherein the peptide induces an active plant response, but does not induce a hypersensitive response, when applied to plant tissue.

A third aspect of the invention relates to an isolated peptide having the amino acid sequence of:

SXGISEKXXDXXXXXXXXAXXXP    (SEQ ID NO:3, modified P4 consensus), wherein

X at position 2 is Q, E, g-glutamate, G, A, or S;
X at position 8 is Q, E, g-glutamate, G, A, or S;
X at position 9 is M, S, L, A, I, V, or F, or a non-hydrophobic amino acid other than serine;
X at position 11 is Q, E, g-glutamate, G, A, or S;
X at position 12 is L, I, or F, or a non-hydrophobic amino acid;
X at position 13 is L, A, I, V, or F, or a non-hydrophobic amino acid;
X at position 14 is any hydrophilic amino acid;
X at position 15 is Q, E, g-glutamate, G, A, S, K, or I;
X at position 16 is L, A, I, V, M, or F, or a non-hydrophobic amino acid;
X at position 17 is M, I, S, or F, or a non-hydrophobic amino acid other than serine;
X at position 18 is Q, E, g-glutamate, G, A, or S;
X at position 20 is M, L, I, V, or F, or a non-hydrophobic amino acid;
X at position 21 is M, L or F, or a non-hydrophobic amino acid; and
X at position 22 is Q, E, g-glutamate, G, A, or S,
wherein one of the residues at positions 9, 12, 13, 16, 20, and 21 is a non-hydrophobic amino acid or A, or the residue at position 17 is a non-hydrophobic amino acid other than serine; and wherein the peptide induces an active plant response, but does not induce a hypersensitive response, when applied to plant tissue.

A fourth aspect of the invention relates to an isolated peptide having the amino acid sequence of:

XXGISEKXJDXJJTXJJXAJJXX    (SEQ ID NO: 4, modified P1 consensus), wherein

X at position 1 is N, D, isoD, G, A, or S;
X at position 2 is Q, E, g-glutamate, G, A, or S;
X at position 8 is Q, E, g-glutamate, G, A, or S;
X at position 11 is Q, E, g-glutamate, G, A, or S;
X at position 15 is Q, E, g-glutamate, G, A, or S;
X at position 18 is M, T, K, E, g-glutamate, G, A, or S;
X at position 22 is Q, E, g-glutamate, G, A, or S;
X at position 23 is Q, E, g-glutamate, G, A, or S;
J at positions 9, 12, 13, 16, 17, 20, and 21 are hydrophobic amino acids selected from L, V, I, and F, except that one of the amino acids at these positions is a non-hydrophobic amino acid or A;
wherein the peptide induces an active plant response, but does not induce a hypersensitive response, when applied to plant tissue.

A fifth aspect of the invention relates to an isolated peptide having the amino acid sequence of:

(i) KPXDSXSXJAKJJSXJJXSJJX    (SEQ ID NO:5, modified P15b/P20 consensus), wherein X at position 3 is N, D, or isoD;
X at position 6 is Q, E, g-glutamate, G, A, or S;
X at position 8 is N, D, or isoD;
X at position 15 is optional and can be any amino acid;
X at position 18 is M, E, g-glutamate, G, A, S, T, or K;
X at position 22 is optional and can be Q, E, g-glutamate, G, A, or S; and
J at positions 9, 12, 13, 16, 17, 20, and 21 are hydrophobic amino acids selected from L, V, I, and F, except that at least one of the amino acids at these positions is a non-hydrophobic amino acid or
A;
or (ii) JAKJJSXJJXSJJX    (SEQ ID NO: 6, modified P15/20 min consensus), wherein X at position 7 is optional and can be any amino acid;
X at position 10 is M, E, g-glutamate, G, A, S, T, or K;
X at position 14 is optional and can be Q, E, g-glutamate, G, A, or S; and
J at positions 1, 4, 5, 8, 9, 12, and 13 are hydrophobic amino acids selected from L, V, I, and F, except that at least one of the amino acids at these positions is a non-hydrophobic amino acid or A;
and
wherein the peptide induces an active plant response, but does not induce a hypersensitive response, when applied to plant tissue.

A sixth aspect of the invention relates to an isolated peptide having the amino acid sequence of:

PSPJTXJJXXJJGXJJXAXN    (SEQ ID NO: 7, modified P6/6a consensus), wherein

X at position 6 is Q, E, g-glutamate, G, A, or S;
X at position 9 is M, E, g-glutamate, G, A, S, T, or K;
X at position 10 is H or N;
X at position 14 is E, g-glutamate, D, or isoD;
X at position 17 is Q, E, g-glutamate, G, A, or S;
X at position 19 is Q, E, g-glutamate, G, A, or S; and
J at positions 4, 7, 8, 11, 12, 15, and 16 are hydrophobic amino acids selected from L, V, I, M, and F, except that at least one of the amino acids at these positions is a non-hydrophobic amino acid or A; wherein the peptide induces an active plant response, but does not induce a hypersensitive response, when applied to plant tissue.

A seventh aspect of the invention relates to an isolated peptide having the amino acid sequence of:

(i) XXXXXXJXXJJXXJJXJJK    (SEQ ID NO: 8, modified P14d consensus), wherein

X at position 1 can be: Q, N, D, E, g-glutamate, isoD, or S;
X at position 2 can be: D, E, g-glutamate, isoD;
X at position 3 can be: P, D, E, isoD, or g-glutamate;
X at position 4 can be M, A, S, D, E, isoD, or g-glutamate
X at position 5 can be Q, E, or g-glutamate;
X at position 6 can be A, E, or g-glutamate;
X at position 8 can be M, L, E, Q, D, N, G, A, S, isoD, or g-glutamate;
X at position 9 can be Q, N, E, D, G, A, S, isoD, or g-glutamate;
X at position 12 can be Q, N, E, D, G, A, S, isoD, or g-glutamate;

X at position 13 can be Q, N, E, D, G, A, S, isoD, or g-glutamate;

X at position 16 can be K, Q, N, E, D, R, G, A, or S; and

J at positions 7, 10, 11, 14, 15, 17, and 18 are hydrophobic amino acids selected from L, V, I, and F, except that at least one of the amino acids at these positions is a non-hydrophobic amino acid or A; or (ii) JXXJJXXJJXJJK (SEQ ID NO: 9, modified P14d min consensus), wherein X at position 2 can be M, L, E, Q, D, N, G, A, S, isoD, or g-glutamate;

X at position 3 can be Q, N, E, D, G, A, S, isoD, or g-glutamate;

X at position 6 can be Q, N, E, D, G, A, S, isoD, or g-glutamate;

X at position 7 can be Q, N, E, D, G, A, S, isoD, or g-glutamate;

X at position 10 can be K, Q, N, E, D, R, G, A, or S; and

J at positions 1, 4, 5, 8, 9, 11, and 12 are hydrophobic amino acids selected from L, V, I, and F, except that at least one of the amino acids at these positions is a non-hydrophobic amino acid or A;

wherein the peptide induces an active plant response, but does not induce a hypersensitive response, when applied to plant tissue.

An eighth aspect of the invention relates to an isolated peptide having the amino acid sequence of:

(i) JXXJJXJJXXJJ (SEQ ID NO: 10, modified P25 consensus) wherein

X at position 2 can be Q, N, E, g-glutamate, D, isoD, T, S, A, or G;

X at position 3 can be K, Q, N, E, g-glutamate, D, isoD, T, S, A, or G;

X at position 6 can be K, Q, N, E, g-glutamate, D, isoD, T, S, A, or G;

X at position 9 can be E, g-glutamate, D, isoD, Q, N, T, S, A, or G;

X at position 10 can be A, G, S, T, E, g-glutamate, D, isoD, Q, or N; and

J at positions 1, 4, 5, 7, 8, 10, and 11 are hydrophobic amino acids selected from L, V, I, F, and M, except that at least one of the amino acids at these positions is a non-hydrophobic amino acid or A;

or (ii) JXXJJXXJJXJJXXJJ (SEQ ID NO: 11, modified P25 consensus) wherein

X at position 2 can be T, S, A, G, D, isoD, E, g-glutamate, Q, or N;

X at position 3 can be G, T, S, A, D, isoD, E, g-glutamate, Q, or N;

X at position 6 can be Q, N, E, g-glutamate, D, isoD, T, S, A, or G;

X at position 7 can be K, Q, N, E, g-glutamate, D, isoD, T, S, A, or G;

X at position 10 can be K, Q, N, E, g-glutamate, D, isoD, T, S, A, or G;

X at position 13 can be E, g-glutamate, D, isoD, Q, N, T, S, A, or G;

X at position 14 can be A, G, S, T, E, g-glutamate, D, isoD, Q, or N;

J at positions 1, 4, 5, 8, 9, 11, 12, and 15 are hydrophobic amino acids selected from L, V, I, F, and M, except that at least one of the amino acids at these positions is a non-hydrophobic amino acid or A; and J at position 16 is optional and a hydrophobic amino acid selected from L, V, I, and F;

wherein the peptide induces an active plant response, but does not induce a hypersensitive response, when applied to plant tissue.

A ninth aspect of the invention relates to an isolated peptide comprising the amino acid sequence of:

(i) XXXXXXXXXXXJXXJJXXJJXXJJXXX (SEQ ID NO: 12, modified P17/18), wherein

X at position 1 can be any amino acid, but preferably Q, S, E, g-glutamate, A, T, G, D, isoD, N, K, or R;

X at position 2 can be any amino acid, but preferably Q, S, E, g-glutamate, A, T, G, D, isoD, N, K, or R;

X at position 3 can be any amino acid, but preferably P, Q, S, E, g-glutamate, A, T, G, D, isoD, N, K, or R;

X at position 4 can be any amino acid, but preferably I, Q, S, E, g-glutamate, A, T, G, D, N, isoD, K, or R;

X at position 5 can be any amino acid, but preferably D, isoD, S, E, g-glutamate, A, T, G, N, Q, K, or R;

X at position 6 can be any amino acid, but preferably R, Q, S, E, g-glutamate, A, T, G, D, isoD, N, or K;

X of position 7 can be any amino acid, but preferably Q, S, E, g-glutamate, A, T, G, D, isoD, N, K, or R;

X at position 8 can be any amino acid, but preferably T, Q, S, E, g-glutamate, A, G, D, isoD, N, K, or R;

X at position 9 can be any amino acid, but preferably I, Q, S, E, g-glutamate, A, T, G, D, isoD, N, K, or R;

X at position 10 can be any amino acid, but preferably E, g-glutamate, Q, S, A, T, G, D, isoD, N, K, or R;

X at position 11 can be any amino acid, but preferably Q, S, E, g-glutamate, A, T, G, D, isoD, N, K, or R;

X at position 13 can be any amino acid, but preferably A, S, T, G, D, isoD, E, g-glutamate, Q, N, K, or R;

X at position 14 can be any amino acid, but preferably Q, A, S, T, G, D, isoD, E, g-glutamate, N, K, or R;

X at position 17 can be any amino acid, but preferably A, S, T, G, D, isoD, E, g-glutamate, Q, N, K, or R;

X at position 18 can be any amino acid, but preferably Q, A, S, T, G, D, isoD, E, g-glutamate, N, K, or R;

X at position 21 can be any amino acid, but preferably K, A, S, T, G, D, isoD, E, g-glutamate, Q, N, or R;

X at position 22 can be any amino acid, but preferably S, A, T, G, D, isoD, E, g-glutamate, Q, N, K, or R;

X at position 25 can be any amino acid, but preferably S, A, T, G, D, isoD, E, g-glutamate, Q, N, K, or R;

X at position 26 can be any amino acid, but preferably P, S, A, T, G, D, isoD, E, g-glutamate, Q, N, K, or R;

X at position 27 can be any amino acid, but preferably Q, S, A, T, G, D, isoD, E, g-glutamate, N, K, or R;

J at positions 12, 15, 16, 19, 20, 23, and 24 are hydrophobic amino acids selected from L, V, I, F, and M, except that at least one of the amino acids at these positions is a non-hydrophobic amino acid or A; or (ii) JXXJJXXJJXXJJ (SEQ ID NO: 13, modified P17/18 min consensus), wherein X at position 2 can be any amino acid, but preferably A, S, T, G, D, isoD, E, g-glutamate, Q, N, K, or R;

X at position 3 can be any amino acid, but preferably Q, A, S, T, G, D, isoD, E, g-glutamate, N, K, or R;

X at position 6 can be any amino acid, but preferably A, S, T, G, D, isoD, E, g-glutamate, Q, N, K, or R;

X at position 7 can be any amino acid, but preferably Q, A, S, T, G, D, isoD, E, g-glutamate, N, K, or R;

X at position 10 can be any amino acid, but preferably K, A, S, T, G, D, isoD, E, g-glutamate, Q, N, or R;

X at position 11 can be any amino acid, but preferably S, A, T, G, D, isoD, E, g-glutamate, Q, N, K, or R; and J at positions 1, 4, 5, 8, 9, 12, and 13 are hydrophobic amino acids selected from L, V, I, F, and M, except that at least one of the amino acids at these positions is a non-hydrophobic amino acid or A;

wherein the peptide induces an active plant response, but does not induce a hypersensitive response, when applied to plant tissue.

A tenth aspect of the invention relates to an isolated peptide comprising the amino acid sequence of:

XJXXJJXJJXXJJ (SEQ ID NO: 14, modified P19 consensus), wherein

X at position 1 is optional and can be L, I, V, F, or M;
X at position 3 can be any amino acid, but preferably K, A, S, T, G, D, isoD, E, g-glutamate, Q, N, or R;
X at position 4 can be any amino acid, but preferably A, S, T, G, D, isoD, E, g-glutamate, Q, N, K, or R;
X at position 7 can be any amino acid, but preferably K, A, S, T, G, D, isoD, E, g-glutamate, Q, N, or R;
X at position 10 can be any amino acid, but preferably A, S, T, G, D, isoD, E, g-glutamate, Q, N, K, or R;
X at position 11 can be any amino acid, but preferably R, A, S, T, G, D, isoD, E, g-glutamate, Q, N, or K; and
J at positions 2, 5, 6, 8, 9, 12, and 13 are hydrophobic amino acids selected from L, V, I, F, and M, except that at least one of the amino acids at these positions is a non-hydrophobic amino acid or A;

wherein the peptide induces an active plant response, but does not induce a hypersensitive response, when applied to plant tissue.

An eleventh aspect of the invention relates to an isolated peptide that includes the amino acid sequence of:

$Z_1$-LLXLFXXIL-$Z_2$ (SEQ ID NO: 126, P3 minimum) wherein

X at position 3 is any hydrophilic amino acid, preferably K, A, S, T, G, D, isoD, E, g-glutamate, Q, N, or R;
X at position 6 is any hydrophilic amino acid, preferably K, A, S, T, G, D, isoD, E, g-glutamate, Q, N, or R;
X at position 7 is any hydrophilic amino acid, preferably K, A, S, T, G, D, isoD, E, g-glutamate, Q, N, or R; and
wherein one of $Z_1$ and $Z_2$ is present, but preferably not both, with $Z_1$ comprising LXX- where each X is a hydrophilic amino acid, preferably K, A, S, T, G, D, isoD, E, g-glutamate, Q, N, or R, and with $Z_2$ comprising -XXLF where each X is a hydrophilic amino acid, preferably K, A, S, T, G, D, isoD, E, g-glutamate, Q, N, or R.

A twelfth aspect of the invention relates to an isolated peptide that includes the amino acid sequence of: L-X-X-(L/I)-(L/I)-X-X-(L/I/V)-(L/I/V) (SEQ ID NO: 116), wherein the peptide is free of cysteine and methionine; each X at positions 2, 3, 6, 7 is any amino acid; and the peptide induces an active plant response, but does not induce a hypersensitive response, when applied to plant tissue.

A thirteenth aspect of the invention relates to a fusion protein that includes one of the peptides of the first through twelfth aspects of the invention along with one or more of a purification tag, a solubility tag, or a second peptide according to one of the first through twelfth aspects of the invention.

A fourteenth aspect of the invention relates to an isolated peptide selected from the group consisting of DVGQLIGELIDRGLQ (SEQ ID NO: 15), GDVGQLIGELIDRGLQSVLAG (SEQ ID NO: 16), SSRALQEVIAQLAQELTHN (SEQ ID NO: 17), or GLEDIKAALDTLIHEKLG (SEQ ID NO: 18). Also encompassed by this aspect of the invention are fusion proteins that include one of these peptides along with one or more of a purification tag, a solubility tag, or a second peptide according to one of the first through twelfth and fourteenth aspects of the invention.

A fifteenth aspect of the invention relates to a composition that includes one or more peptides or fusion proteins according to the first, second, third, fourth, fifth, sixth, seventh, eighth, ninth, tenth, eleventh, twelfth, thirteenth, or fourteenth aspects of the invention, and a carrier.

A sixteenth aspect of the invention relates to a method of imparting disease resistance to plants. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant or plant seed or the locus where the plant is growing or is expected to grow, wherein said applying is effective to impart disease resistance.

A seventeenth aspect of the invention relates to a method of enhancing plant growth. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant or plant seed or the locus where the plant is growing or is expected to grow, wherein said applying is effective to enhance plant growth.

An eighteenth aspect of the invention relates to a method of increasing a plant's tolerance and resistance to biotic stressors. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant or plant seed or the locus where the plant is growing or is expected to grow, wherein said applying is effective to increase the plant's tolerance and resistance to biotic stress factors selected from the group consisting of pests such as insects, arachnids, nematodes, weeds, and combinations thereof.

A nineteenth aspect of the invention relates to a method of increasing a plant's tolerance to abiotic stress. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant or plant seed or the locus where the plant is growing or is expected to grow, wherein said applying is effective to increase the plant's tolerance to abiotic stress factors selected from the group consisting of salt stress, water stress (including drought and flooding), ozone stress, heavy metal stress, cold stress, heat stress, nutritional stress (phosphate, potassium, nitrogen deficiency) and combinations thereof.

A twentieth aspect of the invention relates to a method imparting desiccation resistance to cuttings removed from ornamental plants. This method includes: applying an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant or the locus where the plant is growing, wherein said applying is effective to impart desiccation resistance to cuttings removed from the ornamental plant.

A twenty-first aspect of the invention relates to a method of imparting post-harvest disease or post-harvest desiccation resistance to a fruit or vegetable. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant containing a fruit or vegetable or the locus where the plant is growing; or applying an effective amount of the isolated peptide or the composition to a harvested fruit or vegetable, wherein said applying is effective to impart post-harvest disease resistance or desiccation resistance to the fruit or vegetable.

A twenty-second aspect of the invention relates to a method of enhancing the longevity of fruit or vegetable ripeness. This method includes: applying an effective amount of an isolated peptide or fusion protein according to the first, second, third, fourth, fifth, sixth, seventh, eighth, ninth, tenth, eleventh, twelfth, thirteenth or fourteenth aspects of the invention or a composition according to the fifteenth aspect of the invention to a plant containing a fruit or vegetable or the locus where the plant is growing; or applying an effective amount of the isolated peptide or the composition to a harvested fruit or vegetable, wherein said applying is effective to enhance the longevity of fruit or vegetable ripeness.

A twenty-third aspect of the invention relates to a method of modulating one or more biological signaling processes of a plant. This method includes: applying an effective amount of an isolated peptide according to the first, second, third, fourth, fifth, sixth, seventh, eighth, ninth, tenth, eleventh, twelfth, thirteenth or fourteenth aspects of the invention or a composition according to the fifteenth aspect of the invention to a plant or the locus where the plant is growing, wherein said applying is effective in initiating one or more biochemical signaling processes.

A twenty-fourth aspect of the invention relates to a DNA construct including a first nucleic acid molecule encoding a peptide according to the first, second, third, fourth, fifth, sixth, seventh, eighth, ninth, tenth, eleventh, twelfth, thirteenth or fourteenth aspects of the invention or a fusion polypeptide containing the same; and a promoter-effective nucleic acid molecule operably coupled to the first nucleic acid molecule. This aspect of the invention also encompasses a recombinant expression vector containing the DNA construct, a recombinant host cell containing the DNA construct, as well as transgenic plants or plant seeds that include a recombinant plant cell of the invention (which contains the DNA construct).

A twenty-fifth aspect of the invention relates to a method of imparting disease resistance to plants, enhancing plant growth, imparting tolerance and resistance to biotic stressors, imparting tolerance to abiotic stress, or modulating plant biochemical signaling. This method includes providing a transgenic plant transformed with a DNA construct according to the twenty-fourth aspect of the invention; and growing the plant under conditions effective to permit the DNA construct to express the peptide or the fusion polypeptide to impart disease resistance, enhance plant growth, impart tolerance and resistance to biotic stressors, impart tolerance to abiotic stress, or modulate biochemical signaling to the transgenic plant.

A twenty-sixth aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant transformed with a DNA construct according to the twenty-fourth aspect of the invention; and growing the plant under conditions effective to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

A twenty-seventh aspect of the invention relates to a method of imparting disease resistance to plants, enhancing plant growth, imparting tolerance and resistance to biotic stressors, imparting tolerance to abiotic stress, or modulating biochemical signaling. This method includes providing a transgenic plant seed transformed with a DNA construct according to the twenty-fourth aspect of the invention; planting the transgenic plant seed in soil; and propagating a transgenic plant from the transgenic plant seed to permit the DNA construct to express the peptide or the fusion polypeptide to impart disease resistance, enhance plant growth, impart tolerance to biotic stress and resistance to biotic stressors, or impart tolerance to abiotic stress.

A twenty-eighth aspect of the invention relates to a method of imparting desiccation resistance to cuttings removed from ornamental plants, imparting post-harvest disease or post-harvest desiccation resistance to a fruit or vegetable, or enhancing the longevity of fruit or vegetable ripeness. The method includes providing a transgenic plant seed transformed with a DNA construct according to the twenty-fourth aspect of the invention; planting the transgenic plant seed in soil; and propagating a transgenic plant from the transgenic plant seed to permit the DNA construct to express the peptide or the fusion polypeptide to impart desiccation resistance to cuttings removed from a transgenic ornamental plant, impart post-harvest disease resistance or desiccation resistance to a fruit or vegetable removed from the transgenic plant, or enhance longevity of ripeness for a fruit or vegetable removed from the transgenic plant.

By providing peptides that do not elicit a hypersensitive response but elicit other active plant responses, including, among others, peroxide production, growth enhancement, and resistance to biotic and abiotic stress, where such peptides desirably exhibit improved solubility, stability, resistance to chemical degradation, or a combination of these properties, it will afford growers with greater flexibility in preparing, handling, and delivering to plants in their fields or greenhouses effective amounts of compositions containing these HR-negative peptides. Simplifying the application process for growers will lead to greater compliance and, thus, improved results with respect to one or more of disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These and other benefits are described herein.

DETAILED DESCRIPTION OF THE INVENTION

One aspect of the invention relates to novel peptides that possess the ability to induce an active plant response, but not a hypersensitive response, that afford one or more of the following attributes: modified biochemical signaling; enhanced growth; pathogen resistance; and/or biotic or abiotic stress resistance.

As used herein, naturally occurring amino acids are identified throughout by the conventional three-letter and/or one-letter abbreviations, corresponding to the trivial name of the amino acid, in accordance with the following list: Alanine (Ala, A), Arginine (Arg, R), Asparagine (Asn, N), Aspartic acid (Asp, D), Cysteine (Cys, C), Glutamic acid (Glu, E), Glutamine (Gln, Q), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). The abbreviations are accepted in the peptide art and are recommended by the IUPAC-IUB commission in biochemical nomenclature. Naturally occurring variations of amino acids include, without limitation, gamma-glutamate (g-Glu) and isoaspartate (iso-Asp or isoD).

The term "amino acid" further includes analogues, derivatives, and congeners of any specific amino acid referred to herein, as well as C-terminal or N-terminal protected amino acid derivatives (e.g., modified with an N-terminal, side chain, or C-terminal protecting group, including but not limited to acetylation, formylation, methylation, amidation, esterification, PEGylation, and addition of lipids). Non-naturally occurring amino acids are well known and can be introduced into peptides of the present invention using solid phase synthesis as described below. Furthermore, the term "amino acid" includes both D- and L-amino acids. Hence, an amino acid which is identified herein by its name, three letter or one letter symbol and is not identified specifically as having the D or L configuration, is understood to assume any one of the D or L configurations. In one embodiment, a peptide comprises all L-amino acids.

In certain embodiments, peptides are identified to "consist of" a recited sequence, in which case the peptide includes only the recited amino acid sequence(s) without any extraneous amino acids at the N- or C-terminal ends thereof. To the extent that a recited sequence is in the form of a consensus sequence where one or more of the denoted X or Xaa residues can be any of one or more amino acids, then multiple peptide sequences are embraced by a peptide consisting of such a recited sequence.

In certain other embodiments, peptides are identified to "consist essentially of" a recited sequence, in which case the peptide includes the recited amino acid sequence(s) optionally with one or more extraneous amino acids at the N- and/or C-terminal ends thereof, which extraneous amino acids do not materially alter one or more of the following properties: (i) the ability of the peptide to induce an active plant response, (ii) solubility of the peptide in water or aqueous solutions, (iii) stability of the peptide dissolved in water or aqueous solution at 50° C. over a period of time (e.g., 3 weeks), (iv) resistance of the peptide to chemical degradation in the presence of an aqueous buffered solution that includes a biocidal agent (e.g., Proxel®GXL) at 50° C. over a period of time (e.g., 3 weeks); and (v) the inability of the peptide to induce a hypersensitive response upon infiltration or application to plants.

Briefly, the stability and resistance to chemical degradation of peptides can be assessed as follows using peptide samples having an initial purity of at least about 80%, at least about 82%, at least about 84%, at least about 86%, at least about 88%, at least about 90%, at least about 92%, at least about 94%, at least about 96%, or at least about 98%. For water stability, the peptide is dissolved directly in de-ionized water. For chemical degradation tests, the peptide is dissolved in an aqueous solution containing 50 mM pH buffer and 0.25% Proxel GXL. Exemplary pH buffers include, without limitation: (i) Citrate pH 5.6; (ii) MES pH 6.2; (iii) MOPS pH 6.5; (iv) imidazole pH 7.0; (v) Citrate pH 7.2; (vi) EDDS, pH 7.3; (vii) EDTA pH 8.0; (viii) sodium phosphate pH 8.0; or (ix) TES pH 8.0. Peptides are first dissolved in the aqueous solution at a concentration of 0.5 mg/ml. The samples are incubated at 50° C. to allow for accelerated degradation. An initial sample of the peptide is removed, diluted 10× with water, and analyzed by reverse-phase HPLC. Briefly, 20 µl of the sample is injected into the solvent flow of an HPLC instrument and analyzed on a C18 HPLC column (YMC ProPack C18, YMC, Japan, or C18 Stablebond, Agilent Technologies, USA) using either a triethylamine phosphate in water/acetonitrile gradient or a 0.1% TFA in water/0.1% TFA in acetonitrile gradient to separate different peptide species. Eluting peptides are monitored by UV absorbance at 218 nm and quantified based on the area under the peak. The area under the peak for the initial peptide sample is treated as the standard for relative quantification in subsequent runs. At regular intervals (e.g., 1, 3, 7, 10, 14, 17, and 21 days), each peptide sample is surveyed and analyzed by HPLC as described above. If necessary to observe degradation (i.e., where the peptide exhibits a high degree of chemical stability), this protocol can be extended by several weeks to observe degradation. The quantification of subsequent peptide runs is expressed as a percentage of the original (day 0) HPLC result.

A peptide that is at least partially soluble in water or aqueous solution exhibits a solubility of greater than 0.1 mg/ml, preferably at least about 1.0 mg/ml, at least about 2.0 mg/ml, at least about 3.0 mg/ml, or at least about 4.0 mg/ml. In certain embodiments, the peptide exhibits high solubility in water or aqueous solution, with a solubility of at least about 5.0 mg/ml, at least about 10.0 mg/ml, at least about 15.0 mg/ml, or at least about 20 mg/ml.

A peptide that is stable in water or aqueous solution exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, or three months.

A peptide that is resistant to chemical degradation exhibits at least about 66%, at least about 68%, at least about 70%, at least about 72%, at least about 74%, at least about 76%, at least about 78%, at least about 80%, at least about 82%, at least about 84%, at least about 86%, at least about 88%, or at least about 90% of the original peptide concentration over the designated period of time incubated at 50° C. In certain embodiments, the designated period of time is 3 days, 7 days, 14 days, 21 days, 28 days, one month, two months, three months, or four months. Four months of stability at 50° C. is roughly equivalent to 2 years of stability at room temperature.

A property of a peptide to elicit a hypersensitive response, or not, upon infiltration or application of the peptide to plant tissues can be measured by applying the peptide in dry powder form or in solution form to a plant, particularly though not exclusively a plant leaf. Application rates include 1-500 ug/ml for liquid solution and 0.0001-0.5% (w/w for powder application. Exemplary application of the peptide in solution form is described in the accompanying Examples. Plants are considered HR-positive ("HR+") if they exhibit wide-spread macroscopic cell death visible to the naked eye, accompanied by wilting and browning of the affected tissue within 48 hours. Plants are considered HR-negative ("HR−") if they exhibit no discernible wilting or tissue death observable by naked eye. It is possible that an HR− peptide could cause the death of a small proportion of cells in treated tissue which is not observable by naked eye.

In certain embodiments, material alteration of the one or more properties is intended to mean that there is less than 20% variation, less than 15% variation, less than 10% variation, or less than 5% variation in a recited property when comparing a peptide possessing the one or more extraneous amino acids to an otherwise identical peptide lacking the one or more extraneous amino acids. In certain embodiments, the number of extraneous amino acids at the N- or C-terminal ends is up to 20 amino acids at one or both ends, up to 15 amino acids at one or both ends, up to 10 amino acids at one or both ends, up to 7 amino acids at one or both ends, up to 5 amino acids at one or both ends, or up to 3 amino acids at one or both ends. Further, to the extent that a recited sequence is in the form of a consensus sequence where one or more of the denoted X or Xaa residues can be any of one or more amino acids, then multiple peptide sequences are embraced by the peptide consisting essentially of such a recited sequence, without regard to additional variations of such sequences that are afforded by the presence of extraneous amino acids at the N- and/or C-terminal ends thereof.

In various embodiments of the invention, the disclosed peptides may include a hydrophilic amino acid sequence, e.g., at either the N-terminal or C-terminal end of a designated peptide sequence. The hydrophilic amino acid sequence is at least 3, at least 4, at least 5, at least 6, at least 7, at least 8, at least 9, or at least 10 amino acids in length, and includes amino acid residues that contribute to a hydrophilic property of the amino acid sequence that is adjacent to the amino acid sequence of the designated peptide (i.e., the peptide that induces an active plant response). Different methods have been used in the art to calculate the relative hydrophobicity/hydrophilicity of amino acid residues and proteins (Kyte et al., "A Simple Method for Displaying the Hydropathic Character of a Protein," *J. Mol. Biol.* 157: 105-32 (1982); Eisenberg D, "Three-dimensional Structure of Membrane and Surface Proteins," *Ann. Rev. Biochem.* 53: 595-623 (1984); Rose et al., "Hydrogen Bonding, Hydrophobicity, Packing, and Protein Folding," *Annu. Rev. Biomol. Struct.* 22: 381-415 (1993); Kauzmann, "Some Factors in the Interpretation of Protein Denaturation," *Adv. Protein Chem.* 14: 1-63 (1959), which are hereby incorporated by reference in their entirety). Any one of these hydrophobicity scales can be used for the purposes of the present invention; however, the Kyte-Doolittle hydrophobicity scale is perhaps the most often referenced scale. These hydropathy scales provide a ranking list for the relative hydrophobicity of amino acid residues. For example, amino acids that contribute to hydrophilicity include Arg (R), Lys (K), Asp (D), Glu (E), Gln (Q), Asn (N), and His (H) as well as, albeit to a lesser extent, Ser (S), Thr (T), Gly (G), Pro (P), Tyr (Y), and Trp (W). For example, polyglutamate sequences can be used to enhance solubility of proteins and other drug molecules (Lilie et al, *Biological Chemistry* 394(8):995-1004 (2013); Li et al., *Cancer Research* 58: 2404-2409 (1998)), each of which is hereby incorporated by reference in its entirety).

The "hydropathy index" of a protein or amino acid sequence is a number representing its average hydrophilic or hydrophobic properties. A negative hydropathy index defines the hydrophilicity of the amino acid sequence of interest. The hydropathy index is directly proportional to the hydrophilicity of the amino acid sequence of interest; thus, the more negative the index, the greater its hydrophilicity. In certain embodiments, the added hydrophilic amino acid sequence described above has a hydropathy index of less than 0, −0.4, −0.9, −1.3, −1.6, −3.5, −3.9, or −4.5. In certain embodiments, the resulting entire peptide will have a hydropathy index of less than 0.3, 0.2, 0.1, or 0.0, preferably less than −0.1, −0.2, −0.3, −0.4, more preferably less than −0.5, −0.6, −0.7, −0.8, −0.9, or −1.0.

In the peptides of the present invention, amino acids that contribute to a hydrophilic hydropathy index, for either the peptide as a whole or the added hydrophilic amino acid sequence, include Arg (R), Lys (K), Asp (D), Glu (E), Gln (Q), Asn (N), His (H), Ser (S), Thr (T), Gly (G), Pro (P), Tyr (Y), and Trp (W). Of these, Asp (D), Glu (E), Gln (Q), Asn (N) or their variants are preferred. Exemplary variants include g-glutamate for Glu and isoaspartic acid (or isoD) for Asp.

As used herein, in this and in other aspects of the invention, the term "hydrophobic amino acid" is intended to refer to an amino acid that contributes hydrophobicity to the hydropathy index of a designated amino acid sequence. Amino acids that contribute to a hydrophobic hydropathy index, for either the peptide as a whole or a particular amino acid sequence thereof, include Ile (I), Val (V), Leu (L), Phe (F), Cys (C), Met (M), and Ala (A). In certain embodiments, the term "hydrophobic amino acid" may refer to any one of Ile (I), Val (V), Leu (L), Phe (F), Cys (C), Met (M), and Ala (A); or, alternatively, to any one of Ile (I), Val (V), Leu (L), Phe (F), and Ala (A). In certain other embodiments, the term "hydrophobic amino acid" may refer to one of Ile (I), Val (V), Leu (L), and Phe (F).

As used herein, the term "non-hydrophobic amino acid" is intended to mean an amino acid that is hydrophilic (or not hydrophobic) on one of the above-identified hydrophobicity scales. This term generally refers to those amino acids that contribute to a hydrophilic hydropathy index for either the peptide as a whole or the added hydrophilic amino acid sequence.

In one aspect of the invention, the peptide includes the amino acid sequence of:

J-X-X-X-J-J-X-X-X-J-J-X-X-X-J-J (SEQ ID NO: 1)

wherein the peptide is free of cysteine and methionine, each X at positions 2, 3, 7, 8, 12, and 13 is optional and, when present, is any amino acid, each X residue at positions 4, 9, and 14 is any amino acid, one to three of the J residues at positions 1, 5, 6, 10, 11, 15, and 16 is a non-hydrophobic amino acid or A (preferably, when A is present, it is at one of positions 1, 5, 6, 10, 15, or 16), and all other of the J residues are L, I, V, or F, (preferably L, I, or V); and wherein the peptide induces an active plant response, but does not induce a hypersensitive response, when applied to plant tissue.

In certain embodiments, the peptide does not comprise or consist of the amino acid sequence DVGQLIGELIDRGLQ (SEQ ID NO: 15), GDVGQLIGELIDRGLQSVLAG (SEQ ID NO: 16), SSRALQEVIAQLAQELTHN (SEQ ID NO: 17), or GLEDIKAALDTLIHEKLG (SEQ ID NO: 18). Each of these peptides is identified in Haapalainen et al., "Functional Mapping of Harpin HrpZ of *Pseudomonas syringae* Reveals the Sites Responsible for Protein Oligomerization, Lipid Interactions, and Plant Defence Induction," *Mol. Plant Pathol.* 12(2):151-66 (2011), which is hereby incorporated by reference in its entirety.

In one embodiment, one to three of the J residues at positions 1, 5, 6, 10, 11, 15, and 16 is a non-hydrophobic amino acid, and all other are preferably L, I, V, or F. According to a particular embodiment, not more than two of the J residues at positions 1, 5, 6, 10, 11, 15, and 16 are non-hydrophobic. In another embodiment, not more than one of the J residues at positions 1, 5, 6, 10, 11, 15, and 16 is non-hydrophobic.

In one embodiment, not more than one of the J residues is A, and preferably the A residue is at one of positions 1, 5, 6, 10, 15, and 16; one or two of the remaining J residues is optionally a non-hydrophobic amino acid, and all other J residues are L, I, V, or F. In certain embodiments, not more than one of the J residues is A, and preferably the A residue is at one of positions 1, 5, 6, 10, 15, and 16; and all other J residues are L, I, V, or F.

In certain embodiments, the number of amino acids separating the residues at position 1 from positions 5 and 6, from positions 10 and 11, and from positions 15 and 16 can vary from one to three amino acids. In one embodiment, one of the X residues at positions 2 and 3 is not present, one of the X residues at positions 7 and 8 is not present, one of the X residues at positions 12 and 13 is not present, or two or more of the X residues at these positions is not present. For example, in one embodiment, one of the X residues at positions 2 and 3 and one of the X residues at positions 7 and 8 are not present. In another embodiment, the X residue at position 12, 13, or both, is not present. In another embodiment, one of the X residues at positions 2 and 3, one of the X residues at positions 7 and 8, and one of the X residues at positions 12 and 13 are not present.

In another embodiment, each of the X residues at positions 2, 3, 7, and 8 is present (i.e., the peptide includes three amino acids separating the residue at position 1 from the residues at positions 5 and 6, and the residues at positions 5 and 6 from the residues positions 10 and 11). In another embodiment, the X residue at position 12 is present or the X residues at positions 12 and 13 are present (i.e., the peptide includes two or three amino acids separating the residues at positions 10 and 11 from the residues at positions 15 and 16).

In the preceding paragraphs, the residue numbering refers to SEQ ID NO: 1, although because certain residues are optional, the actual position of J residues and intervening residues may differ in any one particular peptide.

The peptide length in this embodiment is less than 100 amino acids, or alternatively less than 90 amino acids, less than 80 amino acids, less than 70 amino acids, less than 60 amino acids, or less than about 50 amino acids. In certain embodiments, the peptide length is between 12 and about 50 amino acids in length.

In the embodiments described above, where X residues at each of positions 2, 3, 7, 8, 12, (when present) of SEQ ID NO: 1 can be any amino acid, in certain embodiments these residues are independently selected from the group of Arg (R), Lys (K), Asp (D), Glu (E), Gln (Q), Asn (N), Ser (S), Thr (T), Gly (G), isoaspartic acid (isoD), and g-glutamate, and each X residue at positions 4, 9, and 13 is independently selected from the group consisting of G, A, S, T, D, isoD, E, g-glutamate, Q, N, K, and R.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Exemplary peptides according to the first aspect of the invention comprise amino acid sequences identified in Table 1 below:

TABLE 1

| Name | Sequence | SEQ ID NO: |
|---|---|---|
| P14-22L, 26E | QAGPQSANKTGNVDDANNQDPLQALEQLLEDLV | 19 |
| P14-22A, 26L | QAGPQSANKTGNVDDANNQDPAQALLQLLEDLV | 20 |
| P14-22A, 26E | QAGPQSANKTGNVDDANNQDPAQALEQLLEDLV | 21 |
| P14-22E, 26L | QAGPQSANKTGNVDDANNQDPEQALLQLLEDLV | 22 |
| P14-22E, 26E | QAGPQSANKTGNVDDANNQDPEQALEQLLEDLV | 23 |
| P14-22E, 26E-R | QAGPQSANETGNVDDANNQDPEQALEQLLEDLVR | 24 |
| P14-22E, 26A | QAGPQSANKTGNVDDANNQDPE ALAQLLEDLV | 25 |
| P14-22L, 26A | QAGPQSANKTGNVDDANNQDPLQALAQLLEDLV | 26 |
| P14-22A, 26A | QAGPQSANKTGNVDDANNQDPAQALAQLLEDLV | 27 |
| P14-22L, 25-26A | QAGPQSANKTGNVDDANNQDPLQAAQLLEDLV | 28 |
| P14-22L, 28-29A | QAGPQSANKTGNVDDANNQDPLQALLQAAEDLV | 29 |
| P14-22L, 32-33A | QAGPQSANKTGNVDDANNQDPLQALLQLLEDAA | 30 |
| P14-22L, 26, 29A | QAGPQSANKTGNVDDANNQDPLQALAQLAEDLV | 31 |
| P14-22L, 29, 32A | QAGPQSANKTGNVDDANNQDPLQALLQLAEDAV | 32 |
| P14f-7D | QDPAQADEQLLEDLVKLLK | 33 |
| P14f-10D | QDPAQALEQDLEDLVKLLK | 34 |
| P14f-11D | QDPAQALEQLDEDLVKLLK | 35 |

TABLE 1-continued

| Name | Sequence | SEQ ID NO: |
|---|---|---|
| P14f-14D | QDPAQALEQLLEDDVKLLK | 36 |
| P14f-15D | QDPAQALEQLLEDLDKLLK | 37 |
| P14f-17D | QDPAQALEQLLEDLVKDLK | 38 |
| P14f-18D | QDPAQALEQLLEDLVKLDK | 39 |
| P14f-7S | QDPAQASEQLLEDLVKLLK | 40 |
| P14f-10S | QDPAQALEQSLEDLVKLLK | 41 |
| P14f-11S | QDPAQALEQLSEDLVKLLK | 42 |
| P14f-14S | QDPAQALEQLLEDSVKLLK | 43 |
| P14f-15S | QDPAQALEQLLEDLSKLLK | 44 |
| P14f-17S | QDPAQALEQLLEDLVKSLK | 45 |
| P14f-18S | QDPAQALEQLLEDLVKLSK | 46 |

In certain embodiments, these peptides consist essentially of, or consist of, the amino sequence of one or more of SEQ ID NOS: 19-46.

Other exemplary peptides according to the first aspect of the invention comprise the amino acid sequences identified in Table 2 below:

TABLE 2

| Name | Sequence | SEQ ID NO: |
|---|---|---|
| P4-14S-13A | SQGISEKQLDQLASQLIQALLQP | 47 |
| P4-14S-13D | SQGISEKQLDQLDSQLIQALLQP | 48 |
| P4-14S-17D | SQGISEKQLDQLLSQLDQALLQP | 49 |
| P4-14S-21D | SQGISEKQLDQLLSQLIQALDQP | 50 |
| P4-d18 | SQGISEKQLDQLLSQLI_ALLQP | 51 |
| P4-14S-9S | SQGISEKQSDQLLSQLIQALLQP | 52 |
| P4-14S-9Y | SQGISEKQYDQLLSQLIQALLQP | 53 |
| P4-14S-13Q | SQGISEKQLDQLQSQLIQALLQP | 54 |
| P4-14S-16S | SQGISEKQLDQLLSQSIQALLQP | 55 |
| P4-14S-20S | SQGISEKQLDQLLSQLIQASLQP | 56 |
| P4-14S-9A | SQGISEKQADQLLSQLIQALLQP | 57 |
| P4-14S-9D | SQGISEKQDDQLLSQLIQALLQP | 58 |
| P4-14S-12D | SQGISEKQLDQDLSQLIQALLQP | 59 |
| P4-14S-16A | SQGISEKQLDQLLSQAIQALLQP | 60 |
| P4-14S-17S | SQGISEKQLDQLLSQLSQALLQP | 61 |
| P4-d10, 14, 18 | SQGISEKQL_QLL_QLI_ALLQP | 62 |
| P4-i21Q | SQGISEKQLDQLLSQLIQAQLLQP | 63 |
| P4-i21H | SQGISEKQLDQLLSQLIQAHLLQP | 64 |
| P4-i10A | SQGISEKQLADQLLSQLIQALLQP | 65 |
| P4-i14A | SQGISEKQLDQLLASQLIQALLQP | 66 |
| P4-i18A | SQGISEKQLDQLLSQLIAQALLQP | 67 |
| P4-i10A, 14A, 18A | SQGISEKQLADQLLASQLIAQALLQP | 68 |

In certain embodiments, these peptides consist essentially of, or consist of, the amino sequence of one or more of SEQ ID NOS: 47-68.

Further exemplary peptides according to the first aspect of the invention comprise the amino acid sequences identified in Table 3 below:

TABLE 3

| Name | Sequence | SEQ ID NO: |
|---|---|---|
| P25min-7D | SEEEEEDTGVLQKLLKILEAL | 69 |
| P25min-10D | SEEEEELTGDLQKLLKILEAL | 70 |
| P25min-11D | SEEEEELTGVDQKLLKILEAL | 71 |
| P25min-14D | SEEEEELTGVLQKDLKILEAL | 72 |
| P25min-15D | SEEEEELTGVLQKLDKILEAL | 73 |
| P25min-17D | SEEEEELTGVLQKLLKDLEAL | 74 |
| P25min-18D | SEEEEELTGVLQKLLKIDEAL | 75 |
| P25min-21D | SEEEEELTGVLQKLLKILEAD | 76 |
| P25min-7S | SEEEEESTGVLQKLLKILEAL | 77 |
| P25min-10S | SEEEEELTGSLQKLLKILEAL | 78 |
| P25min-11S | SEEEEELTGVSQKLLKILEAL | 79 |
| P25min-14S | SEEEEELTGVLQKSLKILEAL | 80 |
| P25min-15S | SEEEEELTGVLQKLSKILEAL | 81 |
| P25min-17S | SEEEEELTGVLQKLLKSLEAL | 82 |

TABLE 3-continued

| Name | Sequence | SEQ ID NO: |
|---|---|---|
| P25min-18S | *SEEEEE*ELTGVLQKLLKISEAL | 83 |
| P25min-21S | *SEEEEE*ELTGVLQKLLKILEAS | 84 |

In Table 3, the peptides include the solubility tag SEEEEE, indicated by italic print. Peptides comprising the sequences shown in Table 3 but lacking this specific solubility tag (or having a different solubility tag) are also contemplated herein.

In certain embodiments, these peptides consist essentially of, or consist of, the amino sequence of one or more of SEQ ID NOS: 69-84.

Peptides of the first aspect of the invention may also comprise the amino acid sequences identified in Table 4 below:

TABLE 4

| Name | Sequence | SEQ ID NO: |
|---|---|---|
| P18min-7D | *SEEEEE*DAQLLAQLLKSLL | 85 |
| P18min-10D | *SEEEEE*LAQDLAQLLKSLL | 86 |
| P18min-11D | *SEEEEE*LAQLDAQLLKSLL | 87 |
| P18min-14D | *SEEEEE*LAQLLAQDLKSLL | 88 |
| P18min-15D | *SEEEEE*LAQLLAQLDKSLL | 89 |
| P18min-18D | *SEEEEE*LAQLLAQLLKSDL | 90 |
| P18min-19D | *SEEEEE*LAQLLAQLLKSLD | 91 |
| P18min-7S | *SEEEEE*SAQLLAQLLKSLL | 92 |
| P18min-10S | *SEEEEE*LAQSLAQLLKSLL | 93 |
| P18min-11S | *SEEEEE*LAQLSAQLLKSLL | 94 |
| P18min-14S | *SEEEEE*LAQLLAQSLKSLL | 95 |
| P18min-15S | *SEEEEE*LAQLLAQLSKSLL | 96 |
| P18min-18S | *SEEEEE*LAQLLAQLLKSSL | 97 |
| P18min-19S | *SEEEEE*LAQLLAQLLKSLS | 98 |

In Table 4, the peptides include the solubility tag SEEEEE, indicated by italic print. Peptides comprising the sequences shown in Table 4 but lacking this specific solubility tag (or having a different solubility tag) are also contemplated herein.

In certain embodiments, these peptides consist essentially of, or consist of, the amino sequence of one or more of SEQ ID NOS: 85-98.

In another embodiment of the first aspect of the invention, peptides comprise the amino acid sequences identified in Table 5 below:

TABLE 5

| Name | Sequence | SEQ ID NO: |
|---|---|---|
| P19min-7D | *SEEEEE*DKALLKLIARLL | 99 |
| P19min-10D | *SEEEEE*LKADLKLIARLL | 100 |
| P19min-11D | *SEEEEE*LKALDKLIARLL | 101 |

TABLE 5-continued

| Name | Sequence | SEQ ID NO: |
|---|---|---|
| P19min-13D | *SEEEEE*LKALLKDIARLL | 102 |
| P19min-14D | *SEEEEE*LKALLKLDARLL | 103 |
| P19min-17D | *SEEEEE*LKALLKLIARDL | 104 |
| P19min-18D | *SEEEEE*LKALLKLIARLD | 105 |
| P19min-7S | *SEEEEE*SKALLKLIARLL | 106 |
| P19min-10S | *SEEEEE*LKASLKLIARLL | 107 |
| P19min-11S | *SEEEEE*LKALSKLIARLL | 108 |
| P19min-13S | *SEEEEE*LKALLKSIARLL | 109 |
| P19min-14S | *SEEEEE*LKALLKLSARLL | 110 |
| P19min-17S | *SEEEEE*LKALLKLIARSL | 111 |
| P19min-18S | *SEEEEE*LKALLKLIARLS | 112 |

In Table 5, the peptides include the solubility tag SEEEEE, indicated by italic print. Peptides comprising the sequences shown in Table 5 but lacking this specific solubility tag (or having a different solubility tag) are also contemplated herein.

In certain embodiments, these peptides consist essentially of, or consist of, the amino sequence of one or more of SEQ ID NOS: 99-112.

Another aspect of the invention relates to an isolated peptide comprising the amino acid sequence of one of SEQ ID NOS: 113, 114, 117-123, 127, 133-138, 140-142, 144, 145, 148-150, and 153-155, as shown in Table 6 below:

TABLE 6

| Name | Sequence | SEQ ID NO: |
|---|---|---|
| P14 | QAGPQSANKTGNVDDANNQDPMQALMQLLEDLV | 113 |
| P14a | ANNQDPMQALMQLLEDLV | 114 |
| P14-dc1 | QAGPQSANKTGNVDDANNQDPMQALMQLLEDL | 121 |
| P14-dc2 | QAGPQSANKTGNVDDANNQDPMQALMQLLED | 122 |
| P14-dc4 | QAGPQSANKTGNVDDANNQDPMQALMQLL | 123 |
| P14-40 | *SEEEEE*LMQLLEDLV | 127 |
| P14-dN2 | GPQSANKTGNVDDANNQDPMQALMQLLEDLV | 117 |
| P14-dN4 | QSANKTGNVDDANNQDPMQALMQLLEDLV | 118 |
| P14-dN6 | ANKTGNVDDANNQDPMQALMQLLEDLV | 119 |
| P14-dN8 | KTGNVDDANNQDPMQALMQLLEDLV | 120 |
| P4-14S-13V | SQGISEKQLDQLVSQLIQALLQP | 133 |
| P4-14S-13F | SQGISEKQLDQLFSQLIQALLQP | 134 |
| P4-14S-16V | SQGISEKQLDQLLSQVIQALLQP | 135 |
| P4-14S-17F | SQGISEKQLDQLLSQLFQALLQP | 136 |
| P4-14S-20V | SQGISEKQLDQLLSQLIQAVLQP | 137 |
| P4-14S-20F | SQGISEKQLDQLLSQLIQAFLQP | 138 |

TABLE 6-continued

| Name | Sequence | SEQ ID NO: |
|---|---|---|
| P4-116 | SQGISEKQLDQLLSQL | 140 |
| P4-117 | SQGISEKQLDQLLSQ | 141 |
| P18-8 | QQPIDRQTIEQMAQLLAQLL | 142 |
| P19-9 | *SEEEEE*IGDNPLLKALLKLIA | 144 |
| P19-10 | *SEEEEEE*LLKALLKLIA | 145 |
| P15-62 | KPNDSQSNIAKLISALI | 148 |
| P15-63 | *SEEEEEE*IAKLISALI | 149 |
| P15-60 | *SEEEEEEE*IAKLISALIESLL | 150 |
| P25-12 | *SEEEEE*LTGVLQKLLK_ILE | 153 |
| P25-13 | *SEEEEE*LTLTGVLQKLLKILE | 154 |
| P25-14 | *SEEEEE*LTLTGVLQKLLKIL | 155 |

In Table 6, several peptides include the solubility tags S-polyE where the polyE segment contains from 3 to 7 Glu (E) residues, indicated by italic print. Peptides comprising the sequences shown in Table 6 but lacking this specific solubility tag (or having a different solubility tag) are also contemplated herein.

In certain embodiments, these peptides consist essentially of, or consist of, the amino sequence of one or more of SEQ ID NOS: 113, 114, 117-123, 127, 133-138, 140-142, 144, 145, 148-150, 153-159.

Another aspect of the invention relates to an isolated peptide having the amino acid sequence of:

XXGISEKXXXXXXXXXXXXXXX (SEQ ID NO: 2, modified P1/P4 consensus), wherein

X at position 1 is optional and can be S, N, D, isoD, G, A, or S;
X at position 2 is optional and can be Q, E, g-glutamate, G, A, or S;
X at position 8 is Q, E, g-glutamate, G, A, or S;
X at position 9 is M, L, I, F, or V, or a non-hydrophobic amino acid;
X at position 10 is optional and can be D or isoD;
X at position 11 is Q, E, g-glutamate, G, A, or S;
X at position 12 is M, L, I, or F, or a non-hydrophobic amino acid;
X at position 13 is M, L, or I, or a non-hydrophobic amino acid;
X at position 14 is optional and can be any hydrophilic amino acid, S, T, D, isoD, K, or Q, and optionally A or C;
X at position 15 is Q, E, g-glutamate, G, A, S, K, or I;
X at position 16 is M, L, I, V, or F, or a non-hydrophobic amino acid;
X at position 17 is M, L, I, A, or V, or a non-hydrophobic amino acid;
X at position 18 is Q, E, g-glutamate, G, A, S, M, T, or K;
X at position 19 is A, D, isoD, S, V, T, K, R, E, H, or G;
X at position 20 is M, L, or I;
X at position 21 is M, L, I, V, S, or F, or a non-hydrophobic amino acid other than serine;
X at position 22 is Q, E, g-glutamate, G, A, S;
X at position 23 is P, Q, E, g-glutamate, G, A, or S; and wherein at least one of the residues at positions 9, 12, 13, 16, 17, and 20 is a non-hydrophobic amino acid, or the residue at position 21 is a non-hydrophobic amino acid other than serine; and
wherein the peptide induces an active plant response, but does not induce a hypersensitive response, when applied to plant tissue.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

One exemplary family of peptides according to this aspect of the invention have the amino acid sequence of:

SXGISEKXXDXXXXXXXXAXXXP (SEQ ID NO: 3, modified P4 consensus), wherein

X at position 2 is Q, E, g-glutamate, G, A, or S;
X at position 8 is Q, E, g-glutamate, G, A, or S;
X at position 9 is M, S, L, A, I, V, or F, or a non-hydrophobic amino acid other than serine;
X at position 11 is Q, E, g-glutamate, G, A, or S;
X at position 12 is L, I, or F, or a non-hydrophobic amino acid;
X at position 13 is L, A, I, V, or F, or a non-hydrophobic amino acid;
X at position 14 is any hydrophilic amino acid;
X at position 15 is Q, E, g-glutamate, G, A, S, K, or I;
X at position 16 is L, A, I, V, M, or F, or a non-hydrophobic amino acid;
X at position 17 is M, I, S, or F, or a non-hydrophobic amino acid other than serine;
X at position 18 is Q, E, g-glutamate, G, A, or S;
X at position 20 is M, L, I, V, or F, or a non-hydrophobic amino acid;
X at position 21 is M, L or F, or a non-hydrophobic amino acid; and
X at position 22 is Q, E, g-glutamate, G, A, or S;
wherein one of the residues at positions 9, 12, 13, 16, 20, and 21 is a non-hydrophobic amino acid or A, or the residue at position 17 is a non-hydrophobic amino acid other than serine; and wherein the peptide induces an active plant response, but does not induce a hypersensitive response, when applied to plant tissue. Preferably, one to four, not more than three, not more than two, or exactly one of the residues at positions 9, 12, 13, 16, 20, and 21 is a non-hydrophobic amino acid, or the residue at position 17 is a non-hydrophobic amino acid other than serine.

In certain embodiments, these peptides according to SEQ ID NO: 2 also meet the structural features defining the peptides of SEQ ID NO: 1, in which case methionine and cysteine residues are not present. Thus, in these embodiments, X at position 14 can be any hydrophilic amino acid other than methionine or cysteine, preferably S or T.

Exemplary peptides that share the consensus structure with SEQ ID NO: 3, or are derived from SEQ ID NO: 3, are identified in Table 7 below:

TABLE 7

Peptide Variants of Peptide P4 (consensus SEQ ID NO: 3)

| Name | Sequence | SEQ ID NO: |
|---|---|---|
| P4-14S-13D | SQGISEKQLDQLDSQLIQALLQP | 48 |
| P4-14S-17D | SQGISEKQLDQLLSQLDQALLQP | 49 |

TABLE 7-continued

Peptide Variants of Peptide P4
(consensus SEQ ID NO: 3)

| Name | Sequence | SEQ ID NO: |
|---|---|---|
| P4-14S-21D | SQGISEKQLDQLLSQLIQALDQP | 50 |
| P4-d18 | SQGISEKQLDQLLSQLI_ALLQP | 51 |
| P4-14S-9S | SQGISEKQSDQLLSQLIQALLQP | 52 |
| P4-14S-9Y | SQGISEKQYDQLLSQLIQALLQP | 53 |
| P4-14S-13Q | SQGISEKQLDQLQSQLIQALLQP | 54 |
| P4-14S-16S | SQGISEKQLDQLLSQSIQALLQP | 55 |
| P4-14S-20S | SQGISEKQLDQLLSQLIQASLQP | 56 |
| P4-14S-9D | SQGISEKQDDQLLSQLIQALLQP | 58 |
| P4-14S-12D | SQGISEKQLDQDLSQLIQALLQP | 59 |
| P4-14S-17S | SQGISEKQLDQLLSQLSQALLQP | 61 |
| P4-14S-16D | SQGISEKQLDQLLSQDIQALLQP | 161 |
| P4-14S-20D | SQGISEKQLDQLLSQLIQADLQP | 162 |
| P4-14S-13S | SQGISEKQLDQLSSQLIQALLQP | 163 |

In certain other embodiments, the isolated peptide consists essentially of, or consists of, the amino acid sequence of one or more of SEQ ID NOS: 48-56, 58, 59, 61 and 161-163.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Another exemplary family of peptides according to this aspect of the invention have the amino acid sequence of:

XXGISEKXJDXJJTXJJXAJJXX (SEQ ID NO: 4, modified P1 consensus), wherein

X at position 1 is N, D, isoD, G, A, or S;
X at position 2 is Q, E, g-glutamate, G, A, or S;
X at position 8 is Q, E, g-glutamate, G, A, or S;
X at position 11 is Q, E, g-glutamate, G, A, or S;
X at position 15 is Q, E, g-glutamate, G, A, or S;
X at position 18 is M, T, K, E, g-glutamate, G, A, or S;
X at position 22 is Q, E, g-glutamate, G, A, or S;
X at position 23 is Q, E, g-glutamate, G, A, or S; and
J at positions 9, 12, 13, 16, 17, 20, and 21 are hydrophobic amino acids selected from L, V, I, and F, except that one of the amino acids at these positions is a non-hydrophobic amino acid or A;
wherein the peptide induces an active plant response, but does not induce a hypersensitive response, when applied to plant tissue. Preferably, one to four, not more than three, not more than two, or exactly one of the residues at positions 9, 12, 13, 16, 17, 20, and 21 is a non-hydrophobic amino acid or A. In one embodiment, not more than one of the J residues is A, and preferably the A residue is at one of positions 9, 12, 13, 16, 20, and 21; one or two of the remaining J residues is optionally a non-hydrophobic amino acid, and all other J residues are L, I, V, or F. In certain embodiments, not more than one of the J residues is A, and preferably the A residue is at one of positions 9, 12, 13, 16, 20, and 21; and all other J residues are L, I, V, or F.

In certain embodiments, these peptides according to SEQ ID NO: 4 also meet the structural features defining the peptides of SEQ ID NO: 1, in which case methionine and cysteine residues are not present. Thus, in those embodiments, X at position 18 is T, K, E, g-glutamate, G, A, or S.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Exemplary peptides that share the consensus structure with SEQ ID NO: 4 are identified in Table 8 below:

TABLE 8

Peptide Variants of P1 (consensus SEQ ID NO: 4)

| Peptide Name | Sequence | SEQ ID NO: |
|---|---|---|
| P1-13P-20P | NQGISEKQLDQLPTQLIMAPLQQ | 164 |
| P1 | NQGISEKQLDQLLTQLIMALLQQ | 165 |
| P1-9D | NQGISEKQDDQLLTQLIMALLQQ | 166 |
| P1-9S | NQGISEKQSDQLLTQLIMALLQQ | 167 |
| P1-12D | NQGISEKQLDQDLTQLIMALLQQ | 168 |
| P1-12S | NQGISEKQLDQSLTQLIMALLQQ | 169 |
| P1-13D | NQGISEKQLDQLDTQLIMALLQQ | 170 |
| P1-13S | NQGISEKQLDQLSTQLIMALLQQ | 171 |
| P1-16D | NQGISEKQLDQLLTQDIMALLQQ | 172 |
| P1-16S | NQGISEKQLDQLLTQSIMALLQQ | 173 |
| P1-17D | NQGISEKQLDQLLTQLDMALLQQ | 174 |
| P1-17S | NQGISEKQLDQLLTQLSMALLQQ | 175 |
| P1-20D | NQGISEKQLDQLLTQLIMADLQQ | 176 |
| P1-20S | NQGISEKQLDQLLTQLIMASLQQ | 177 |
| P1-21D | NQGISEKQLDQLLTQLIMALDQQ | 178 |
| P1-21S | NQGISEKQLDQLLTQLIMALSQQ | 179 |

Additional variants of these peptides may include the substitution of methionine at position 18 with T, K, E, g-glutamate, G, A, or S, as noted above.

In certain other embodiments, the isolated peptide consists essentially of, or consists of, the amino acid sequence of one or more of SEQ ID NOS: 164, 166-179.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Yet another aspect of the invention relates to an isolated peptide having the amino acid sequence of:

(i) KPXDSXSXJAKJJSXJJXSJJX (SEQ ID NO: 5, modified P15b/P20 consensus), wherein

X at position 3 is N, D, or isoD;
X at position 6 is Q, E, g-glutamate, G, A, or S;
X at position 8 is N, D, or isoD;
X at position 15 is optional and can be any amino acid;
X at position 18 is M, E, g-glutamate, G, A, S, T, or K;
X at position 22 is optional and can be Q, E, g-glutamate, G, A, or S; and J at positions 9, 12, 13, 16, 17, 20, and 21 are hydrophobic amino acids selected from L, V, I, F, and A, except that at least one of the amino acids at these positions is a non-hydrophobic amino acid; or (ii) JAKJJSXJJXSJJX  (SEQ ID NO: 6, modified P15/20 min consensus), wherein X at position 7 is optional and can be any amino acid;
X at position 10 is M, E, g-glutamate, G, A, S, T, or K;
X at position 14 is optional and can be Q, E, g-glutamate, G, A, or S; and
J at positions 1, 4, 5, 8, 9, 12, and 13 are hydrophobic amino acids selected from L, V, I, and F, except that at least one of the amino acids at these positions is a non-hydrophobic amino acid or A; and wherein the peptide induces an active plant response, but does not induce a hypersensitive response, when applied to plant tissue. Preferably, one to four, not more than three, not more than two, or exactly one of the residues at positions 9, 12, 13, 16, 17, 20, and 21 of SEQ ID NO: 5 is a non-hydrophobic amino acid or A; and one to four, not more than three, not more than two, or exactly one of the residues at positions 1, 4, 5, 8, 9, 12, and 13 of SEQ ID NO: 6 is a non-hydrophobic amino acid or A. In one embodiment, not more than one of the J residues is A, and preferably the A residue is at one of positions 9, 12, 13, 16, 20, and 21 of SEQ ID NO: 5 or positions 1, 4, 5, 8, 12, and 13 of SEQ ID NO: 6; one or two of the remaining J residues is optionally a non-hydrophobic amino acid, and all other J residues are L, I, V, or F. In certain embodiments, not more than one of the J residues is A, and preferably the A residue is at one of positions 9, 12, 13, 16, 20, and 21 of SEQ ID NO: 5 or positions 1, 4, 5, 8, 12, and 13 of SEQ ID NO: 6; and all other J residues are L, I, V, or F.

Exemplary peptides that share the consensus structure with SEQ ID NO:5 or 6 are identified in Table 9 below:

TABLE 9

Peptide Variants of P15/P20 (consensus SEQ ID NO: 5 or 6)

| Name | Sequence | SEQ ID NO: |
|---|---|---|
| P15b-9D | KPNDSQSNDAKLISALIMSLLQ | 180 |
| P15b-12D | KPNDSQSNIAKDISALIMSLLQ | 181 |
| P15b-13D | KPNDSQSNIAKLDSALIMSLLQ | 182 |
| P15b-16D | KPNDSQSNIAKLISADIMSLLQ | 183 |
| P15b-17D | KPNDSQSNIAKLISALDMSLLQ | 184 |
| P15b-20D | KPNDSQSNIAKLISALIMSDLQ | 185 |
| P15b-21D | KPNDSQSNIAKLISALIMSLDQ | 186 |
| P15b-9S | KPNDSQSNSAKLISALIMSLLQ | 187 |
| P15b-12S | KPNDSQSNIAKSISALIMSLLQ | 188 |
| P15b-13S | KPNDSQSNIAKLSSALIMSLLQ | 189 |
| P15b-16S | KPNDSQSNIAKLISASIMSLLQ | 190 |
| P15b-17S | KPNDSQSNIAKLISALSMSLLQ | 191 |
| P15b-20S | KPNDSQSNIAKLISALIMSSLQ | 192 |
| P15b-21S | KPNDSQSNIAKLISALIMSLSQ | 193 |

Additional variants of these peptides may include the substitution of methionine at position 18 with E, g-glutamate, G, A, S, T, or K, as noted above.

In certain other embodiments, the peptide consists essentially of, or consists of, the amino acid sequence of one or more of SEQ ID NOS: 180-193.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

A further aspect of the invention relates to an isolated peptide having the amino acid sequence of:

PSPJTXJJXXJJGXJJXAXN  (SEQ ID NO: 7, modified P6/6a consensus), wherein

X at position 6 is Q, E, g-glutamate, G, A, or S;
X at position 9 is M, E, g-glutamate, G, A, S, T, or K;
X at position 10 is H or N;
X at position 14 is E, g-glutamate, D, or isoD;
X at position 17 is Q, E, g-glutamate, G, A, or S;
X at position 19 is Q, E, g-glutamate, G, A, or S; and
J at positions 4, 7, 8, 11, 12, 15, and 16 are hydrophobic amino acids selected from L, V, I, M, and F, except that at least one of the amino acids at these positions in a non-hydrophobic amino acid or A;

wherein the peptide induces an active plant response, but does not induce a hypersensitive response, when applied to plant tissue. Preferably, one to four, not more than three, not more than two, or exactly one of the residues at positions 4, 7, 8, 11, 12, 15, and 16 is a non-hydrophobic amino acid or A. In one embodiment, not more than one of the J residues is A, and preferably the A residue is at one of positions 4, 7, 8, 11, 15, and 16 of SEQ ID NO: 7; one or two of the remaining J residues is optionally a non-hydrophobic amino acid, and all other J residues are L, I, V, M, or F. In certain embodiments, not more than one of the J residues is A, and preferably the A residue is at one of positions 4, 7, 8, 11, 15, and 16 of SEQ ID NO: 7; and all other J residues are L, I, V, M, or F.

Exemplary peptides that share the consensus structure with SEQ ID NO: 7 are identified in Table 10 below:

TABLE 10

Peptide Variants of P6/6a (consensus SEQ ID NO: 7)

| Name | Sequence | SEQ ID NO: |
|---|---|---|
| P6a-4D | PSPDTQMLMHIVGEILQAQN | 194 |
| P6a-7D | PSPFTQDLMHIVGEILQAQN | 195 |
| P6a-8D | PSPFTQMDMHIVGEILQAQN | 196 |
| P6a-11D | PSPFTQMLMHDVGEILQAQN | 197 |
| P6a-12D | PSPFTQMLMHIDGEILQAQN | 198 |
| P6a-15D | PSPFTQMLMHIVGEDLQAQN | 199 |
| P6a-16D | PSPFTQMLMHIVGEIDQAQN | 200 |
| P6a-4S | PSPSTQMLMHIVGEILQAQN | 201 |
| P6a-7S | PSPFTQSLMHIVGEILQAQN | 202 |
| P6a-8S | PSPFTQMSMHIVGEILQAQN | 203 |
| P6a-11S | PSPFTQMLMHSVGEILQAQN | 204 |
| P6a-12S | PSPFTQMLMHISGEILQAQN | 205 |

TABLE 10-continued

Peptide Variants of P6/6a (consensus SEQ ID NO: 7)

| Name | Sequence | SEQ ID NO: |
|---|---|---|
| P6a-15S | PSPFTQMLMHIVGESLQAQN | 206 |
| P6a-16S | PSPFTQMLMHIVGEISQAQN | 207 |

Additional variants of these peptides may include the substitution of methionine at position 7 with L, I, V, F, a non-hydrophobic amino acid, or A, as noted above; and substitution of methionine at position 9 with L, E, g-glutamate, G, A, S, T, or K, as noted above.

In certain other embodiments, the isolated peptide consists essentially of, or consists of, the amino acid sequence of one or more of SEQ ID NOS: 194-207.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Another aspect of the invention relates to a peptide having the amino acid sequence of:

(i) XXXXXXJXXJJXXJJXJJK    (SEQ ID NO: 8, modified P14d consensus), wherein

X at position 1 can be: Q, N, D, E, g-glutamate, isoD, or S;
X at position 2 can be: D, E, g-glutamate, isoD;
X at position 3 can be: P, D, E, isoD, or g-glutamate;
X at position 4 can be M, A, S, D, E, isoD, or g-glutamate
X at position 5 can be Q, E, or g-glutamate;
X at position 6 can be A, E, or g-glutamate;
X at position 8 can be M, L, E, Q, D, N, G, A, S, isoD, or g-glutamate;
X at position 9 can be Q, N, E, D, G, A, S, isoD, or g-glutamate;
X at position 12 can be Q, N, E, D, G, A, S, isoD, or g-glutamate;
X at position 13 can be Q, N, E, D, G, A, S, isoD, or g-glutamate;
X at position 16 can be K, Q, N, E, D, R, G, A, or S; and
J at positions 7, 10, 11, 14, 15, 17, and 18 are hydrophobic amino acids selected from L, V, I, and F, except that at least one of the amino acids at these positions is a non-hydrophobic amino acid or A; or (ii) JXXJJXXJJXJJK    (SEQ ID NO: 9, modified P14d min consensus), wherein X at position 2 can be M, L, E, Q, D, N, G, A, S, isoD, or g-glutamate;
X at position 3 can be Q, N, E, D, G, A, S, isoD, or g-glutamate;
X at position 6 can be Q, N, E, D, G, A, S, isoD, or g-glutamate;
X at position 7 can be Q, N, E, D, G, A, S, isoD, or g-glutamate;
X at position 10 can be K, Q, N, E, D, R, G, A, or S; and
J at positions 1, 4, 5, 8, 9, 11, and 12 are hydrophobic amino acids selected from L, V, I, and F, except that at least one of the amino acids at these positions is a non-hydrophobic amino acid or A;
wherein the peptide induces an active plant response, but does not induce a hypersensitive response, when applied to plant tissue. Preferably, one to four, not more than three, not more than two, or exactly one of the residues at positions 7, 10, 11, 14, 15, 17, and 18 of SEQ ID NO: 8 is a non-hydrophobic amino acid or A; and one to four, not more than three, not more than two, or exactly one of the residues at positions 1, 4, 5, 8, 9, 11, and 12 of SEQ ID NO: 9 is a non-hydrophobic amino acid or A. In one embodiment, not more than one of the J residues is A, and preferably the A residue is at one of positions 7, 10, 11, 14, 17, and 18 of SEQ ID NO: 8 or positions 1, 4, 5, 8, 11, and 12 of SEQ ID NO: 9; one or two of the remaining J residues is optionally a non-hydrophobic amino acid, and all other J residues are L, I, V, or F. In certain embodiments, not more than one of the J residues is A, and preferably the A residue is at one of positions 7, 10, 11, 14, 17, and 18 of SEQ ID NO: 8 or positions 1, 4, 5, 8, 11, and 12 of SEQ ID NO: 9; and all other J residues are L, I, V, or F.

Exemplary peptides that share the consensus structure with SEQ ID NO: 8 or 9 are identified in Table 11 below:

TABLE 11

Peptide Variants of P14d (consensus SEQ ID NO: 8 or 9)

| Name | Sequence | SEQ ID NO: |
|---|---|---|
| P14d-7D | QDPMQADMQLLEDLVKLLK | 208 |
| P14d-10D | QDPMQALMQDLEDLVKLLK | 209 |
| P14d-11D | QDPMQALMQLDEDLVKLLK | 210 |
| P14d-14D | QDPMQALMQLLEDDVKLLK | 211 |
| P14d-15D | QDPMQALMQLLEDLDKLLK | 212 |
| P14d-17D | QDPMQALMQLLEDLVKDLK | 213 |
| P14d-18D | QDPMQALMQLLEDLVKLDK | 214 |
| P14d-7S | QDPMQASMQLLEDLVKLLK | 215 |
| P14d-10S | QDPMQALMQSLEDLVKLLK | 216 |
| P14d-11S | QDPMQALMQLSEDLVKLLK | 217 |
| P14d-14S | QDPMQALMQLLEDSVKLLK | 218 |
| P14d-15S | QDPMQALMQLLEDLSKLLK | 219 |
| P14d-17S | QDPMQALMQLLEDLVKSLK | 220 |
| P14d-18S | QDPMQALMQLLEDLVKLSK | 221 |

Additional variants of these peptides may include the substitution of methionine at one or both of positions 4 and 8 with L, E, Q, D, N, G, A, S, isoD, or g-glutamate, as noted above.

In certain other embodiments, the isolated peptide consists essentially of, or consists of, the amino acid sequence of one or more of SEQ ID NOS: 208-221.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

A further aspect of the invention relates to a peptide having the amino acid sequence of:

(i) JXXJJXJJXXJJ    (SEQ ID NO: 10, modified P25 consensus) wherein

X at position 2 can be Q, N, E, g-glutamate, D, isoD, T, S, A, or G;

X at position 3 can be K, Q, N, E, g-glutamate, D, isoD, T, S, A, or G;

X at position 6 can be K, Q, N, E, g-glutamate, D, isoD, T, S, A, or G;

X at position 9 can be E, g-glutamate, D, isoD, Q, N, T, S, A, or G;

X at position 10 can be A, G, S, T, E, g-glutamate, D, isoD, Q, or N; and

J at positions 1, 4, 5, 7, 8, 10, and 11 are hydrophobic amino acids selected from L, V, I, F, and M, except that at least one of the amino acids at these positions is a non-hydrophobic amino acid or A; or (ii) JXXJJXXJJXJJXXJJ (SEQ ID NO: 11, modified P25 consensus) wherein X at position 2 can be T, S, A, G, D, isoD, E, g-glutamate, Q, or N;

X at position 3 can be G, T, S, A, D, isoD, E, g-glutamate, Q, or N;

X at position 6 can be Q, N, E, g-glutamate, D, isoD, T, S, A, or G;

X at position 7 can be K, Q, N, E, g-glutamate, D, isoD, T, S, A, or G;

X at position 10 can be K, Q, N, E, g-glutamate, D, isoD, T, S, A, or G;

X at position 13 can be E, g-glutamate, D, isoD, Q, N, T, S, A, or G;

X at position 14 can be A, G, S, T, E, g-glutamate, D, isoD, Q, or N;

J at positions 1, 4, 5, 8, 9, 11, 12, and 15 are hydrophobic amino acids selected from L, V, I, F, and M, except that at least one of the amino acids at these positions is a non-hydrophobic amino acid or A; and J at position 16 is optional and a hydrophobic amino acid selected from L, V, I, and F;

wherein the peptide induces an active plant response, but does not induce a hypersensitive response, when applied to plant tissue. Preferably, one to four, not more than three, not more than two, or exactly one of the residues at positions 1, 4, 5, 7, 8, 10, and 11 of SEQ ID NO: 10 is a non-hydrophobic amino acid, and one to four, not more than three, not more than two, or exactly one of the residues at positions 1, 4, 5, 8, 9, 11, 12, 15, and 16 of SEQ ID NO: 11 is a non-hydrophobic amino acid. In one embodiment, not more than one of the J residues is A, and preferably the A residue is at one of positions 1, 4, 5, 7, 10, and 11 of SEQ ID NO: 10 or positions 1, 4, 5, 8, 11, 12, 15, and 16 of SEQ ID NO: 11; one or two of the remaining J residues is optionally a non-hydrophobic amino acid, and all other J residues are L, I, V, or F. In certain embodiments, not more than one of the J residues is A, and preferably the A residue is at one of positions 1, 4, 5, 7, 10, and 11 of SEQ ID NO: 10 or positions 1, 4, 5, 8, 11, 12, 15, and 16 of SEQ ID NO: 11; and all other J residues are L, I, V, or F.

Exemplary peptides that share the consensus structure with SEQ ID NO: 10 or 11 are identified in Table 12 below:

TABLE 12

Peptide Variants of P25 (consensus SEQ ID NO: 10 or 11)

| Name | Sequence | SEQ ID NO: |
|---|---|---|
| P25-5D | GGLTDTGVLQKLMKILNALVQ | 222 |
| P25-8D | GGLTLTGDLQKLMKILNALVQ | 223 |

TABLE 12-continued

Peptide Variants of P25 (consensus SEQ ID NO: 10 or 11)

| Name | Sequence | SEQ ID NO: |
|---|---|---|
| P25-9D | GGLTLTGVDQKLMKILNALVQ | 224 |
| P25-12D | GGLTLTGVLQKDMKILNALVQ | 225 |
| P25-13D | GGLTLTGVLQKLDKILNALVQ | 226 |
| P25-15D | GGLTLTGVLQKLMKDLNALVQ | 227 |
| P25-16D | GGLTLTGVLQKLMKIDNALVQ | 228 |
| P25-19D | GGLTLTGVLQKLMKILNADVQ | 229 |
| P25-20D | GGLTLTGVLQKLMKILNALDQ | 230 |
| P25-5S | GGLTSTGVLQKLMKILNALVQ | 231 |
| P25-8S | GGLTLTGSLQKLMKILNALVQ | 232 |
| P25-9S | GGLTLTGVSQKLMKILNALVQ | 233 |
| P25-12S | GGLTLTGVLQKSMKILNALVQ | 234 |
| P25-13S | GGLTLTGVLQKLSKILNALVQ | 235 |
| P25-15S | GGLTLTGVLQKLMKSLNALVQ | 236 |
| P25-16S | GGLTLTGVLQKLMKISNALVQ | 237 |
| P25-19S | GGLTLTGVLQKLMKILNASVQ | 238 |
| P25-20S | GGLTLTGVLQKLMKILNALSQ | 239 |

Additional variants of these peptides may include the substitution of methionine at position 13 with L, V, I, and F, as noted above.

In certain other embodiments, the isolated peptide consists essentially of, or consists of, the amino acid sequence of one or more of SEQ ID NOS: 222-239.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Still another aspect of the invention relates to a peptide having the amino acid sequence:

(i) XXXXXXXXXXXJXXJJXXJJXXJJXXX (SEQ ID NO: 12, modified P17/18), wherein

X at position 1 can be any amino acid, but preferably Q, S, E, g-glutamate, A, T, G, D, isoD, N, K, or R;

X at position 2 can be any amino acid, but preferably Q, S, E, g-glutamate, A, T, G, D, isoD, N, K, or R;

X at position 3 can be any amino acid, but preferably P, Q, S, E, g-glutamate, A, T, G, D, isoD, N, K, or R;

X at position 4 can be any amino acid, but preferably I, Q, S, E, g-glutamate, A, T, G, D, N, isoD, K, or R;

X at position 5 can be any amino acid, but preferably D, isoD, S, E, g-glutamate, A, T, G, N, Q, K, or R;

X at position 6 can be any amino acid, but preferably R, Q, S, E, g-glutamate, A, T, G, D, isoD, N, or K;

X of position 7 can be any amino acid, but preferably Q, S, E, g-glutamate, A, T, G, D, isoD, N, K, or R;

X at position 8 can be any amino acid, but preferably T, Q, S, E, g-glutamate, A, G, D, isoD, N, K, or R;

X at position 9 can be any amino acid, but preferably I, Q, S, E, g-glutamate, A, T, G, D, isoD, N, K, or R;

X at position 10 can be any amino acid, but preferably E, g-glutamate, Q, S, A, T, G, D, isoD, N, K, or R;

X at position 11 can be any amino acid, but preferably Q, S, E, g-glutamate, A, T, G, D, isoD, N, K, or R;
X at position 13 can be any amino acid, but preferably A, S, T, G, D, isoD, E, g-glutamate, Q, N, K, or R;
X at position 14 can be any amino acid, but preferably Q, A, S, T, G, D, isoD, E, g-glutamate, N, K, or R;
X at position 17 can be any amino acid, but preferably A, S, T, G, D, isoD, E, g-glutamate, Q, N, K, or R;
X at position 18 can be any amino acid, but preferably Q, A, S, T, G, D, isoD, E, g-glutamate, N, K, or R;
X at position 21 can be any amino acid, but preferably K, A, S, T, G, D, isoD, E, g-glutamate, Q, N, or R;
X at position 22 can be any amino acid, but preferably S, A, T, G, D, isoD, E, g-glutamate, Q, N, K, or R;
X at position 25 can be any amino acid, but preferably S, A, T, G, D, isoD, E, g-glutamate, Q, N, K, or R;
X at position 26 can be any amino acid, but preferably P, S, A, T, G, D, isoD, E, g-glutamate, Q, N, K, or R;
X at position 27 can be any amino acid, but preferably Q, S, A, T, G, D, isoD, E, g-glutamate, N, K, or R; and
J at positions 12, 15, 16, 19, 20, 23, and 24 are hydrophobic amino acids selected from L, V, I, F, and M, except that at least one of the amino acids at these positions is a non-hydrophobic amino acid or A;
or (ii) JXXJJXXJJXXJJ (SEQ ID NO: 13, modified P17/18 min consensus), wherein X at position 2 can be any amino acid, but preferably A, S, T, G, D, isoD, E, g-glutamate, Q, N, K, or R;
X at position 3 can be any amino acid, but preferably Q, A, S, T, G, D, isoD, E, g-glutamate, N, K, or R;
X at position 6 can be any amino acid, but preferably A, S, T, G, D, isoD, E, g-glutamate, Q, N, K, or R;
X at position 7 can be any amino acid, but preferably Q, A, S, T, G, D, isoD, E, g-glutamate, N, K, or R;
X at position 10 can be any amino acid, but preferably K, A, S, T, G, D, isoD, E, g-glutamate, Q, N, or R;
X at position 11 can be any amino acid, but preferably S, A, T, G, D, isoD, E, g-glutamate, Q, N, K, or R; and
J at positions 1, 4, 5, 8, 9, 12, and 13 are hydrophobic amino acids selected from L, V, I, F, and M, except that at least one of the amino acids at these positions is a non-hydrophobic amino acid or A;
wherein the peptide induces an active plant response, but does not induce a hypersensitive response, when applied to plant tissue. Preferably, one to four, not more than three, not more than two, or exactly one of the residues at positions 12, 15, 16, 19, 20, 23, and 24 of SEQ ID NO: 12 is a non-hydrophobic amino acid or A; and one to four, not more than three, not more than two, or exactly one of the residues at positions 1, 4, 5, 8, 9, 12, and 13 of SEQ ID NO: 13 is a non-hydrophobic amino acid or A. In one embodiment, not more than one of the J residues is A, and preferably the A residue is at one of positions 12, 15, 16, 19, 23, and 24 of SEQ ID NO: 12 or positions 1, 4, 5, 8, 12, and 13 of SEQ ID NO: 13; one or two of the remaining J residues is optionally a non-hydrophobic amino acid, and all other J residues are L, I, V, F, or M. In certain embodiments, not more than one of the J residues is A, and preferably the A residue is at one of positions 12, 15, 16, 19, 23, and 24 of SEQ ID NO: 12 or positions 1, 4, 5, 8, 12, and 13 of SEQ ID NO: 13; and all other J residues are L, I, V, F, or M.

Exemplary peptides that share the consensus structure with SEQ ID NO: 12 or 13, or are derived from SEQ ID NO: 12 or 13 and meet the consensus structure of SEQ ID NO: 1, are identified in Table 13 below:

TABLE 13

Peptide Variants of P17/P18 (consensus SEQ ID NO: 12 or 13)

| Name | Sequence | SEQ ID NO: |
|---|---|---|
| P18min-7D | SEEEEEDAQLLAQLLKSLL | 85 |
| P18min-10D | SEEEEELAQDLAQLLKSLL | 86 |
| P18min-11D | SEEEEELAQLDAQLLKSLL | 87 |
| P18min-14D | SEEEEELAQLLAQDLKSLL | 88 |
| P18min-15D | SEEEEELAQLLAQLDKSLL | 89 |
| P18min-18D | SEEEEELAQLLAQLLKSDL | 90 |
| P18min-19D | SEEEEELAQLLAQLLKSLD | 91 |
| P18min-7S | SEEEEESAQLLAQLLKSLL | 92 |
| P18min-10S | SEEEEELAQSLAQLLKSLL | 93 |
| P18min-11S | SEEEEELAQLSAQLLKSLL | 94 |
| P18min-14S | SEEEEELAQLLAQSLKSLL | 95 |
| P18min-15S | SEEEEELAQLLAQLSKSLL | 96 |
| P18min-18S | SEEEEELAQLLAQLLKSSL | 97 |
| P18min-19S | SEEEEELAQLLAQLLKSLS | 98 |

In Table 13, peptides include the solubility tag SEEEEE, indicated by italic print. Peptides comprising the sequences shown in Table 13 but lacking this specific solubility tag (or having a different solubility tag) are also contemplated herein.

In certain other embodiments, the isolated peptide consists essentially of, or consists of, the amino acid sequence of one or more of SEQ ID NOS: 85-98.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Yet another aspect of the invention relates to a peptide having the amino acid sequence:

XJXXJJXJJXXJJ (SEQ ID NO: 14, modified P19 consensus), wherein

X at position 1 is optional and can be L, I, V, F, or M;
X at position 3 can be any amino acid, but preferably K, A, S, T, G, D, isoD, E, g-glutamate, Q, N, or R;
X at position 4 can be any amino acid, but preferably A, S, T, G, D, isoD, E, g-glutamate, Q, N, K, or R;
X at position 7 can be any amino acid, but preferably K, A, S, T, G, D, isoD, E, g-glutamate, Q, N, or R;
X at position 10 can be any amino acid, but preferably A, S, T, G, D, isoD, E, g-glutamate, Q, N, K, or R;
X at position 11 can be any amino acid, but preferably R, A, S, T, G, D, isoD, E, g-glutamate, Q, N, or K; and
J at positions 2, 5, 6, 8, 9, 12, and 13 are hydrophobic amino acids selected from L, V, I, F, and M, except that at least one of the amino acids at these positions is a non-hydrophobic amino acid or A;
wherein the peptide induces an active plant response, but does not induce a hypersensitive response, when applied to plant tissue. Preferably, one to four, not more than three, not more than two, or exactly one of the residues at positions 2, 5, 6, 8, 9, 12, and 13 is a non-hydrophobic amino acid. In one embodiment, not more than one of the J residues is A, and preferably the A residue is at one of positions 2, 5, 6, 8, 12, and 13 of SEQ ID NO: 14; one or two of the remaining J residues is optionally a non-hydrophobic amino acid, and all other J residues are L, I, V, F, or M. In certain embodiments, not more than one of the J residues is A, and preferably the A residue is at one of positions 2, 5, 6, 8, 12, and 13 of SEQ ID NO: 14; and all other J residues are L, I, V, F, or M.

Exemplary peptides that share the consensus structure with one of SEQ ID NO: 14, or are derived from one of SEQ ID NO: 14 and meet the consensus structure of SEQ ID NO: 1, are identified in Table 14 below:

TABLE 14

Peptide Variants of P19 (consensus SEQ ID NO: 14)

| Name | Sequence | SEQ ID NO: |
|---|---|---|
| P19min-7D | *SEEEEE*DKALLKLIARLL | 99 |
| P19min-10D | *SEEEEE*LKADLKLIARLL | 100 |
| P19min-11D | *SEEEEE*LKALDKLIARLL | 101 |
| P19min-13D | *SEEEEE*LKALLKDIARLL | 102 |
| P19min-14D | *SEEEEE*LKALLKLDARLL | 103 |
| P19min-17D | *SEEEEE*LKALLKLIARDL | 104 |
| P19min-18D | *SEEEEE*LKALLKLIARLD | 105 |
| P19min-7S | *SEEEEE*SKALLKLIARLL | 106 |
| P19min-10S | *SEEEEE*LKASLKLIARLL | 107 |
| P19min-11S | *SEEEEE*LKALSKLIARLL | 108 |
| P19min-13S | *SEEEEE*LKALLKSIARLL | 109 |
| P19min-14S | *SEEEEE*LKALLKLSARLL | 110 |
| P19min-17S | *SEEEEE*LKALLKLIARSL | 111 |
| P19min-18S | *SEEEEE*LKALLKLIARLS | 112 |

In Table 14, peptides include the solubility tag SEEEEE, indicated by italic print. Peptides comprising the sequences shown in Table 14 but lacking this specific solubility tag (or having a different solubility tag) are also contemplated herein.

In certain embodiments, the isolated peptide consists essentially of, or consists of, the amino acid sequence of SEQ ID NOS: 99-112.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

A further aspect of the invention relates to an isolated peptide that includes the amino acid sequence of:

$Z_1$-LLXLFXXIL-$Z_2$    (SEQ ID NO: 126, P3 minimum) wherein

X at position 3 is any hydrophilic amino acid, preferably K, A, S, T, G, D, isoD, E, g-glutamate, Q, N, or R;

X at position 6 is any hydrophilic amino acid, preferably K, A, S, T, G, D, isoD, E, g-glutamate, Q, N, or R;

X at position 7 is any hydrophilic amino acid, preferably K, A, S, T, G, D, isoD, E, g-glutamate, Q, N, or R; and wherein one of $Z_1$ or $Z_2$ is present, but preferably not both, with $Z_1$ comprising LXX- where each X is a hydrophilic amino acid, preferably K, A, S, T, G, D, isoD, E, g-glutamate, Q, N, or R, and with $Z_2$ comprising -XXLF where each X is a hydrophilic amino acid, preferably K, A, S, T, G, D, isoD, E, g-glutamate, Q, N, or R.

wherein the peptide induces an active plant response, but does not induce a hypersensitive response, when applied to plant tissue.

In one embodiment, $Z_1$ but not $Z_2$ is present. In an alternative embodiment, $Z_2$ but not $Z_1$ is present.

Exemplary peptides that share the consensus structure with SEQ ID NO: 126, or are derived from SEQ ID NO: 126 and meet the consensus structure of SEQ ID NO: 1, are identified in Table 15 below:

TABLE 15

Peptide Variants of P3 (consensus SEQ ID NO: 126)

| Name | Sequence | SEQ ID NO: |
|---|---|---|
| P3-5 | *SEEE*LQQLLKLFSEIL | 156 |
| P3-8 | *SEEEEEE*LLKLFSEILQSLF | 157 |
| P3-9 | *SEEEE*QQLLKLFSEILQSLF | 158 |
| P3-10 | *SEEEEE*LQQLLKLFSEILQ | 159 |

In Table 15, peptides include the solubility tag SEEE, SEEEEE, and SEEEEEE, indicated by italic print. Peptides comprising the sequences shown in Table 15 but lacking this specific solubility tag (or having a different solubility tag) are also contemplated herein.

In certain embodiments, the isolated peptide consists essentially of, or consists of, the amino acid sequence of SEQ ID NOS: 156-159.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

Another aspect of the invention relates to an isolated peptide that includes the amino acid sequence of:

L-X-X-(L/I)-(L/I)-X-X-(L/I/V)-(L/I/V)    (SEQ ID NO: 116)

wherein the peptide is free of cysteine and methionine; each X at positions 2, 3, 6, 7 is any amino acid; and the peptide induces an active plant response, but does not induce a hypersensitive response, when applied to plant tissue.

In certain embodiments, X at one or more of positions 2, 3, 6, and 7 is a non-hydrophobic amino acid, X at two or more of positions 2, 3, 6, and 7 is a non-hydrophobic amino acid, X at three or more of positions 2, 3, 6, and 7 is a non-hydrophobic amino acid, or X at each of positions 2, 3, 6, and 7 is a non-hydrophobic amino acid. In this embodiment, the non-hydrophobic amino acids independently may be any one of G, A, S, T, D, isoD, E, g-glutamate, Q, N, K, and R.

The peptides according to this aspect of the invention are generally denoted by a truncation of the HR box sequence, which is described in co-pending U.S. patent application Ser. No. 14/872,298, entitled "Hypersensitive Response Elicitor Peptides and Use Thereof", filed Oct. 1, 2015, which is hereby incorporated by reference in its entirety. Thus, by virtue of the truncation of the HR box sequence, either by termination of the peptide or substitution of amino acid residues that form part of the HR box sequence, the isolated peptide according to this aspect do not comprise the amino acid sequence:

(L/I/V/F)-X-X-(L/I/V/F)-(L/I)-X-X-(L/I/V)-(L/I)-X-X-(L/I/V/F)-(L/I/V/F)    (SEQ ID NO: 125)

wherein each X at positions 2, 3, 6, 7, 10, 11 is any amino acid.

Exemplary peptides that share the consensus structure with SEQ ID NO: 116 are identified in Table 16 below:

TABLE 16

| Name | Sequence | SEQ ID NO: |
|---|---|---|
| P14-22L, 26L | QAGPQSANKTGNVDDANNQDPLQALLQLLEDLV | 115 |
| P14-32 | *SEEEEE*LEQLLEDLVKLL | 124 |
| P14-31 | *SEEEEEE*ALEQLLEDLVKLL | 129 |
| P14-39 | *SEEEEE*LEQLLEDLV | 160 |
| P14-41 | *SEEEEE*LLQLLEDLV | 128 |
| P1-29 | NQGISEKQLDQLLTQLI | 130 |
| P1-31 | *SEEEE*LDQLLTQLI | 131 |
| P4-111 | SQGISEKQLDQLLSQLI | 132 |
| P4-115 | *SEEEE*LDQLLSQLI | 139 |
| P18-9 | *SEEEEE*LAQLLAQLL | 143 |
| P19-12 | *SEEEEE*KALLKLIARLL | 146 |
| P19-13 | *SEEEEEE*ALLKLIARLL | 147 |
| P15-61 | *SEEEEEEE*IAKLIS_LIESLL | 151 |
| P25-9 | *SEEEEE*LQKLLK_ILEALV | 152 |

In Table 16, peptides include the solubility tags SEEEE and SEEEEE, indicated by italic print. Peptides comprising the sequences shown in Table 15 but lacking the specific solubility tag (or having a different solubility tag) are also contemplated herein.

In certain embodiments, the isolated peptide consists essentially of, or consists of, the amino acid sequence of SEQ ID NOS: 115, 124, 128-132, 139, 143, 146, 147, 151, 152, and 160.

In this embodiment, the isolated peptide is preferably stable when dissolved in water; resistant to chemical degradation in aqueous conditions in the presence of a pH buffer and a biocide, as described above; and/or has a solubility in an aqueous solution of at least about 1.0 mg/ml.

The isolated peptides of the invention can also be presented in the form of a fusion peptide that includes, in addition, a second amino acid sequence coupled to the inventive peptides via peptide bond. The second amino acid sequence can be a purification tag, such as poly-histidine ($His_6$-), a glutathione-S-transferase (GST-), or maltose-binding protein (MBP-), which assists in the purification but can later be removed, i.e., cleaved from the peptide following recovery. Protease-specific cleavage sites or chemical-specific cleavage sites (i.e., in a cleavable linker sequence) can be introduced between the purification tag and the desired peptide. Protease-specific cleavage sites are well known in the literature and include, without limitation, the enterokinase specific cleavage site $(Asp)_4$-Lys, which is cleaved after lysine; the factor Xa specific cleavage site Ile-(Glu or Asp)-Gly-Arg, which is cleaved after arginine; the trypsin specific cleavage site, which cleaves after Lys and Arg; and the Genenase™ I specific cleavage site Pro-Gly-Ala-Ala-His-Tyr. Chemicals and their specific cleavage sites include, without limitation, cyanogen bromide (CNBr), which cleaves at methionine (Met) residues; BNPS-skatole, which cleaves at tryptophan (Trp) residues; formic acid, which cleaves at aspartic acid-proline (Asp-Pro) peptide bonds; hydroxylamine, which cleaves at asparagine-glycine (Asn-Gly) peptide bonds; and 2-nitro-5-thiocyanobenzoic acid (NTCB), which cleaves at cysteine (Cys) residues (see Crimmins et al., "Chemical Cleavage of Proteins in Solution," *Curr. Protocol. Protein Sci.*, Chapter 11:Unit 11.4 (2005), which is hereby incorporated by reference in its entirety). In order to use one of these cleavage methods, it may be necessary to remove unwanted cleavage sites from within the desired peptide sequences by mutation. For example, P14-22E,26E-R (SEQ ID NO: 23) has been mutated for compatibility with trypsin: the lysine residue at position 9 is mutated to a glutamate and a C-terminal arginine is added to represent the product of a theoretical trypsin cleavage. The desired peptide product can be purified further to remove the cleaved purification tags.

The isolated peptides of the invention can also be presented in the form of a fusion peptide that includes multiple peptide sequences of the present invention linked together by a linker sequence, which may or may not take the form of a cleavable amino acid sequence of the type described above. Such multimeric fusion proteins may or may not include purification tags. In one embodiment, each monomeric sequence can include a purification tag linked to a peptide of the invention by a first cleavable peptide sequence; and the several monomeric sequences can be linked to adjacent monomeric sequences by a second cleavable peptide sequence. Consequently, upon expression of the multimeric fusion protein, i.e., in a host cell, the recovered fusion protein can be treated with a protease or chemical that is effective to cleave the second cleavable peptide sequence, thereby releasing individual monomeric peptide sequences containing purification tags. Upon affinity purification, the recovered monomeric peptide sequences can be treated with a protease or chemical that is effective to cleave the first cleavable peptide sequence and thereby release the purification tag from the peptide of interest. The latter can be further purified using gel filtration and/or HPLC as described infra.

These fusion proteins may include the sequences, identified above as SEQ ID NO: 15-18, which were previously identified in Haapalainen et al., "Functional Mapping of Harpin HrpZ of *Pseudomonas syringae* Reveals the Sites Responsible for Protein Oligomerization, Lipid Interactions, and Plant Defence Induction," *Mol. Plant Pathol.* 12(2):151-66 (2011), which is hereby incorporated by reference in its entirety.

According to one approach, the peptides of the present invention can be synthesized by standard peptide synthesis operations. These include both FMOC (9-fluorenylmethyl-oxy-carbonyl) and tBoc (tert-butyloxy-carbonyl) synthesis protocols that can be carried out on automated solid phase peptide synthesis instruments including, without limitation, the Applied Biosystems 431 A, 433 A synthesizers and Peptide Technologies Symphony or large scale Sonata or CEM Liberty automated solid phase peptide synthesizers. The use of alternative peptide synthesis instruments is also contemplated. Peptides prepared using solid phase synthesis are recovered in a substantially pure form.

The peptides of the present invention may be also prepared by using recombinant expression systems followed by separation and purification of the recombinantly prepared peptides. Generally, this involves inserting an encoding nucleic acid molecule into an expression system to which the molecule is heterologous (i.e., not normally present). One or more desired nucleic acid molecules encoding a peptide of the invention may be inserted into the vector. The heterologous nucleic acid molecule is inserted into the expression system or vector in proper sense (5'-3') orientation and correct reading frame relative to the promoter and any other 5' and 3' regulatory molecules. Representative nucleotide sequences for expression in bacteria and plant hosts and included in Table 17 below:

TABLE 17

| Peptide & Optimized Host | Nucleotide Sequence | SEQ ID NO: |
|---|---|---|
| P14 A. thaliana | CAAGCTGGACCTCAATCTGCTAATAAGACTGGA AATGTTGATGATGCTAATAATCAAGATCCTATG CAAGCTCTTATGCAACTTCTTGAAGATCTTGTT | 240 |
| P14 E. coli | CAGGCAGGTCCGCAGAGCGCAAATAAAACCGGT AATGTTGATGATGCAAATAATCAGGATCCGATG CAGGCACTGATGCAGCTGCTGGAAGATCTGGTT | 241 |
| P14d-10D A. thaliana | CAAGATCCTATGCAAGCTCTTATGCAAGATCTT GAAGATCTTGTTAAGCTTCTTAAG | 242 |
| P14d-10D E. coli | CAGGATCCGATGCAGGCACTGATGCAGGATCTG GAAGATCTGGTTAAACTGCTGAAA | 243 |

With knowledge of the encoded amino acid sequence listed herein and the desired transgenic organism, additional codon-optimized DNA sequences and RNA sequences can be generated with nothing more than routine skill.

Expression (including transcription and translation) of a peptide or fusion polypeptide of the invention by the DNA construct may be regulated with respect to the level of expression, the tissue type(s) where expression takes place and/or developmental stage of expression. A number of heterologous regulatory sequences (e.g., promoters and enhancers) are available for controlling the expression of the DNA construct. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394, each of which is hereby incorporated by reference in its entirety), the nopaline synthase (NOS) promoter (Ebert et al., *Proc. Natl. Acad. Sci. (U.S.A.)* 84:5745-5749 (1987), which is hereby incorporated by reference in its entirety), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), which is hereby incorporated by reference in its entirety) and the CaMV 35S promoter (Odell et al., *Nature* 313:810-812 (1985), which is hereby incorporated by reference in its entirety), the figwort mosaic virus 35S-promoter (U.S. Pat. No. 5,378,619, which is hereby incorporated by reference in its entirety), the light-inducible promoter from the small subunit of ribulose-1,5-bis-phosphate carboxylase (ssRUBISCO), the Adh promoter (Walker et al., *Proc. Natl. Acad. Sci. (U.S.A.)* 84:6624-6628 (1987), which is hereby incorporated by reference in its entirety), the sucrose synthase promoter (Yang et al., *Proc. Natl. Acad. Sci. (U.S.A.)* 87:4144-4148 (1990), which is hereby incorporated by reference in its entirety), the R gene complex promoter (Chandler et al., *Plant Cell* 1:1175-1183 (1989), which is hereby incorporated by reference in its entirety), the chlorophyll a/b binding protein gene promoter, the CsVMV promoter (Verdaguer et al., *Plant Mol Biol.,* 37:1055-1067 (1998), which is hereby incorporated by reference in its entirety), and the melon actin promoter (PCT Publ. No. WO00/56863, which is hereby incorporated by reference in its entirety). Exemplary tissue-specific promoters include the tomato E4 and E8 promoters (U.S. Pat. No. 5,859,330, which is hereby incorporated by reference in its entirety) and the tomato 2AII gene promoter (Van Haaren et al., *Plant Mol Bio.,* 21:625-640 (1993), which is hereby incorporated by reference in its entirety).

In one preferred embodiment, expression of the DNA construct is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209:219 (1991), which is hereby incorporated by reference in its entirety), globulin (Belanger and Kriz, *Genet.* 129: 863-872 (1991), GenBank Accession No. L22295, each of which is hereby incorporated by reference in its entirety), gamma zein Z 27 (Lopes et al., *Mol Gen Genet.* 247:603-613 (1995), which is hereby incorporated by reference in its entirety), L3 oleosin promoter (U.S. Pat. No. 6,433,252, which is hereby incorporated by reference in its entirety), phaseolin (Bustos et al., *Plant Cell* 1(9):839-853 (1989), which is hereby incorporated by reference in its entirety), arcelin5 (U.S. Application Publ. No. 2003/0046727, which is hereby incorporated by reference in its entirety), a soybean 7S promoter, a 7Sa promoter (U.S. Application Publ. No. 2003/0093828, which is hereby incorporated by reference in its entirety), the soybean 7Sαβ conglycinin promoter, a 7Sα promoter (Beachy et al., *EMBO J.* 4:3047 (1985); Schuler et al., *Nucleic Acid Res.* 10(24):8225-8244 (1982), each of which is hereby incorporated by reference in its entirety), soybean trypsin inhibitor (Riggs et al., *Plant Cell* 1(6):609-621 (1989), which is hereby incorporated by reference in its entirety), ACP (Baerson et al., *Plant Mol. Biol.,* 22(2):255-267 (1993), which is hereby incorporated by reference in its entirety), stearoyl-ACP desaturase (Slocombe et al., *Plant Physiol.* 104(4):167-176 (1994), which is hereby incorporated by reference in its entirety), soybean a' subunit of β-conglycinin (Chen et al., *Proc. Natl. Acad. Sci.* 83:8560-8564 (1986), which is hereby incorporated by reference in its entirety), *Vicia faba* USP (U.S. Application Publ. No. 2003/229918, which is hereby incorporated by reference in its entirety) and *Zea mays* L3 oleosin promoter (Hong et al., *Plant Mol. Biol.,* 34(3):549-555 (1997), which is hereby incorporated by reference in its entirety).

Nucleic acid molecules encoding the peptides of the present invention can be prepared via solid-phase synthesis using, e.g., the phosphoramidite method and phosphoramidite building blocks derived from protected 2'-deoxynucleosides. To obtain the desired oligonucleotide, the building blocks are sequentially coupled to the growing oligonucleotide chain in the order required by the sequence of the product. Upon the completion of the chain assembly, the product is released from the solid phase to solution, deprotected, collected, and typically purified using HPLC. The limits of solid phase synthesis are suitable for preparing oligonucleotides up to about 200 nt in length, which encodes peptides on the order of about 65 amino acids or less. The ends of the synthetized oligonucleotide can be designed to include specific restriction enzyme cleavage site to facilitate ligation of the synthesized oligonucleotide into an expression vector.

For longer peptides, oligonucleotides can be prepared via solid phase synthesis and then the synthetic oligonucleotide sequences ligated together using various techniques. Recombinant techniques for the fabrication of whole synthetic genes are reviewed, for example, in Hughes et al., "Chapter Twelve—Gene Synthesis: Methods and Applications," *Methods in Enzymology* 498:277-309 (2011), which is hereby incorporated by reference in its entirety.

Once a suitable expression vector is selected, the desired nucleic acid sequences are cloned into the vector using standard cloning procedures in the art, as described by Sambrook et al., Molecular Cloning: A Laboratory Manual, Cold Springs Laboratory, Cold Springs Harbor, N.Y. (1989), or U.S. Pat. No. 4,237,224 to Cohen and Boyer, which are hereby incorporated by reference in their entirety. The vector is then introduced to a suitable host.

A variety of host-vector systems may be utilized to recombinantly express the peptides of the present invention. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by *Agrobacterium*. The expression elements of these vectors vary in their strength and specificities. Depending upon the host-vector system utilized, any one of a number of suitable transcription and translation elements can be used to carry out this and other aspects of the present invention.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

Alternatively, if the peptide of interest of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above. The use of purification tags, described above, can simplify this process.

In certain embodiments, purification is not required. Where purification is not performed, cell-free lysates can be recovered following centrifugation for removal of cellular debris. The resulting cell-free lysate can be treated with heat for a sufficient amount of time to deactivate any native proteases in the recovered fraction, e.g., 10 min at 100° C. If desired, one or more of biocidal agents, protease inhibitors, and non-ionic surfactants can be introduced to such a cell-free preparation (see U.S. Application Publ. No. 20100043095 to Wei, which is hereby incorporated by reference in its entirety).

Once the peptides of the present invention are recovered, they can be used to prepare a composition that includes a carrier, and one or more additives selected from the group consisting of a bacteriocidal or biocidal agent, a protease inhibitor, a non-ionic surfactant, a fertilizer, an herbicide, an insecticide, a fungicide, a nematicide, biological inoculants, plant regulators, and mixtures thereof.

In certain embodiments, the compositions include greater than about 1 nM of the peptide, greater than about 10 nM of the peptide, greater than about 20 nM of the peptide, greater than about 30 nM of the peptide, greater than about 40 nM of the peptide, greater than about 50 nM of the peptide, greater than about 60 nM of the peptide, greater than about 70 nM of the peptide, greater than 80 about nM of the peptide, greater than about 90 nM of the peptide, greater than about 100 nM of the peptide, greater than about 150 nM of the peptide, greater than about 200 nM of the peptide, or greater than about 250 nM of the peptide. In certain embodiments, the compositions include less than about 1 nM of the peptide. For example, certain peptides can be present at a concentration of less than about 2 ng/ml, less than about 1.75 ng/ml, less than about 1.5 ng/ml, less than about 1.25 ng/ml, less than about 1.0 ng/ml, less than about 0.75 ng/ml, less than about 0.5 ng/ml, less than about 0.25 ng/ml, or even less than about 0.1 ng/ml.

Suitable carriers include water, aqueous solutions optionally containing one or more co-solvents, slurries, and solid carrier particles. Exemplary solid carriers include mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, and products of vegetable origin, such as cereal meal, tree bark meal, wood meal and nutshell meal, cellulose powders, starches and starch derivatives, as well as other mono-, di-, and poly-saccharides.

Suitable fertilizers include, without limitation, ammonium sulfate, ammonium phosphate, ammonium nitrate, ureas, and combinations thereof.

Suitable insecticides include, without limitation, members of the neonicotinoid class such as imidicloprid, clothianidin, and thiamethoxam; members of the organophosphate class such as chlorpyrifos and malathion; members of the pyrethroid class such as permethrin; other natural insecticides such as nicotine, nornicotine, and pyrethrins; members of the carbamate class such as aldicarb, carbofuran, and carbaryl; members of the macrocyclic lactone class such as various abamectin, avermectin, and ivermectin products; members of the diamide class such as chlorantraniliprole, cyantraniliprole, and flubendiamide; chitin synthesis inhibitors, particularly those of the benzoylurea class such as lufenuron and diflubenzuron; and any combination thereof, including combinations of two or more, three or more, or four or more insecticides. Additional insecticides are listed in the Compendium of Pesticide Common Names, which is database operated by Alan Wood and available in electronic form at the alanwood.net internet site.

Suitable fungicides include, without limitation, members of the strobilurin class such as azoxystrobin, pyraclostrobin, trifloxystrobin, picoxystrobin, and fluoxastrobin; members of the triazole class such as ipconazole, metconazole, tebuconazole, triticonazole, tetraconazole, difenoconazole, flutriafol, propiconazole and prothioconazole; members of the succinate dehydrogenase class such as carboxin, fluxapyroxad, boscalid and sedaxane: members of the phenylamide class such as metalaxyl, mefenoxam, benalaxyl, and oxadiyxl; members of the phenylpyrrole class such as fludioxonil; members of the phthalimide class such as captan; members of the dithiocarbamate class such as mancozeb and thiram; members of the benzimidazole class such as thiabendazole; and any combination thereof, including combinations of two or more, three or more, or four or more fungicides. Additional fungicides are listed in the Compendium of Pesticide Common Names, which is a database operated by Alan Wood and available in electronic form at the alanwood.net internet site.

Suitable nematicides include, without limitation, chemicals of the carbamate class such as aldicarb, aldoxycarb, oxamyl, carbofuran, and cleothocarb; and chemicals of the organophosphate class such as thionazin, ethoprophos, fenamiphos, fensulfothion, terbufos, isazofos, and ebufos. Additional nematicides are listed in the Compendium of Pesticide Common Names, which is a database operated by Alan Wood and available in electronic form at the alanwood.net internet site.

Suitable bactericides include, without limitation, those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie; Proxel® GXL from ICI). Additional bactericides are listed in the Compendium of Pesticide Common Names, which is a database operated by Alan Wood and available in electronic form at the alanwood.net internet site.

Suitable inoculants include, without limitation, *Bradyrhizobium* spp., particularly *Bradyrhizobium japonicum* (BASF Vault® products), *Bacillus subtilis, Bacillus firmus, Bacillus pumilis, Streptomyces lydicus, Trichoderma* spp., *Pasteuria* spp., other cultures of rhizobial cells (BASF Nodulator® and Rhizo-Flo®), and any combination thereof, including combinations of two or more, three or more, or four or more inoculants.

Plant regulators are chemical substances, either natural or synthetic, that either stimulate or inhibit plant biochemical signaling. These are usually, but not exclusively, recognized by receptors on the surface of the cell, causing a cascade of reactions in the cell. Suitable plant regulators include, without limitation, ethephon; ethylene; salicylic acid; acetylsalicylic acid; jasmonic acid; methyl jasmonate; methyl dihydrojasmonate; chitin; chitosan; abscisic acid; any auxin compound or inhibitor, including but not limited to (4-chlorophenoxy)acetic acid, (2,4-dichlorophenoxy)acetic acid, and 2,3,5-triiodobenzoic acid; any cytokinin, including but not limited to kinetin and zeatin; gibberellins; brassinolide; and any combination thereof, including combinations of two or more, three or more, or four or more regulators.

Other suitable additives include buffering agents, wetting agents, coating agents, and abrading agents. These materials can be used to facilitate application of the compositions in accordance with the present invention. In addition, the compositions can be applied to plant seeds with other conventional seed formulation and treatment materials, including clays and polysaccharides.

Compositions or systems use for plant seed treatment include: one or more of the peptides of the present invention, preferably though not exclusively one or more of peptides p4-14s-9a (SEQ ID NO: 57), p4-14s-12d (SEQ ID NO: 59), p14 (SEQ ID NO: 113), p14a (SEQ ID NO: 114), p14-22E, 26E (SEQ ID NO: 23), p1-29 (SEQ ID NO: 130), and p4-14S-16S (SEQ ID NO: 55) in combination with one or more insecticides, nematicides, fungicides, other inoculants, or other plant regulators, including combinations of multiple insecticides, or multiple nematicides, multiple fungicides, multiple other inoculants, or multiple plant regulators. Suitable insecticides, nematicides, fungicides, inoculants, and plant regulators for these combination treatments include those identified above. These compositions are presented in the form of a single composition at the time of seed treatment. In contrast, a system used for seed treatment may involve multiple treatments, e.g., a composition containing the peptides is used in one treatment and a composition containing the one or more insecticides, nematicides, fungicides, plant regulators and/or bactericides, is used in a separate treatment. In the latter embodiment, both of these treatments are carried out at about the same time, i.e., before planting or at about the time of planting.

One such example includes one or more of peptides of the present invention, including (without limitation) one or more of peptides p4-14s-9a (SEQ ID NO: 57), p4-14s-12d (SEQ ID NO: 59), p14 (SEQ ID NO: 113), p14a (SEQ ID NO: 114), p14-22E,26E (SEQ ID NO: 23), p1-29 (SEQ ID NO: 130), and p4-14S-16S (SEQ ID NO: 55), in combination with one of Poncho™ (clothianidin) available from Bayer Crop Science, Poncho™ VOTiVO (clothianidin and *Bacillus firmus* biological nematicide) available from Bayer Crop Science, and Gaucho™ (imidicloprid) available from Bayer Crop Science.

Another example includes one or more of peptides of the present invention, including (without limitation) one or more of peptides p4-14s-9a (SEQ ID NO: 57), p4-14s-12d (SEQ ID NO: 59), p14 (SEQ ID NO: 113), p14a (SEQ ID NO: 114), p14-22E,26E (SEQ ID NO: 23), p1-29 (SEQ ID NO: 130), and p4-14S-16S (SEQ ID NO: 55), in combination with one of Cruiser™ (thiamethoxam) available from Syngenta, CruiserMaxx™ (thiamethoxam, mefenoxam, and fludioxynil) available from Syngenta, Cruiser Extreme™ (thiamethoxam, mefenoxam, fludioxynil, and azoxystrobin) available from Syngenta, Avicta™ (thiamethoxam and abamectin) available from Syngenta, and Avicta™ Complete (thiamethoxam, abamectin, and Clariva Complete™ which contains the *Pasteuria nishizawae*—Pn1 biological inoculant) available from Syngenta, and Avicta Complete™ Corn (thiamethoxam, mefenoxam, fludioxynil, azoxystrobin, thiabendazole and abamectin) available from Syngenta.

Another example includes one or more of peptides of the present invention, including (without limitation) one or more of peptides p4-14s-9a (SEQ ID NO: 57), p4-14s-12d (SEQ ID NO: 59), p14 (SEQ ID NO: 113), p14a (SEQ ID NO: 114), p14-22E,26E (SEQ ID NO: 23), p1-29 (SEQ ID NO: 130), and p4-14S-16S (SEQ ID NO: 55), in combination with one of Vault Liquid plus Integral (*Bradyrhizobium* species and *Bacillus subtilis* strain MBI 600 inoculants) available from BASF, Vault NP (*Bradyrhizobium japonicum* inoculant) available from BASF, and Subtilex NG (*Bacillus subtilis* biological inoculant) available from BASF.

The present invention further relates to methods of imparting disease resistance to plants, enhancing plant growth, effecting pest control (including insects and nematodes), imparting biotic or abiotic stress tolerance to plants, and/or modulating plant biochemical signaling. These methods involve applying an effective amount of an isolated peptide of the invention, or a composition of the invention to a plant or plant seed or the locus where the plant is growing or is expected to grow. As a consequence of such application, the peptide contacts cells of the plant or plant seed, and induces in the plant or a plant grown from the plant seed disease resistance, growth enhancement, tolerance to biotic stress, tolerance to abiotic stress, or altered biochemical signaling. Alternatively, the peptide or composition of the invention can be applied to plants such that seeds recovered from such plants themselves are able to impart disease resistance in plants, to enhance plant growth, to affect insect control, to impart tolerance to biotic or abiotic stress, and/or to modulate biochemical signaling.

In these embodiments, it is also possible to select plants or plant seeds or the locus to which the isolated peptide or composition of the invention is applied. For example, for fields known to contain a high nematode content, the plants or plant seeds to be grown in such fields, or the fields (locus), can be selectively treated by applying the isolated peptide or composition of the invention as described herein; whereas no such treatment may be necessary for plants or plant seeds grown in fields containing low nematode content. Similarly, for fields having reduced irrigation, the plants or plant seeds to be grown in such fields, or the fields (locus), can be selectively treated by applying the isolated peptide or composition of the invention as described herein; whereas no such treatment may be necessary for plants or plant seeds grown in fields having adequate irrigation. Likewise, for fields prone to flooding, the plants or plant seeds to be grown in such fields, or the fields (locus), can be selectively treated by applying the isolated peptide or composition of the invention as described herein; whereas no such treatment may be necessary for plants or plant seeds grown in fields that are not prone to flooding. As yet another example of such selection, for fields prone to insect attack at certain times of the growing season, the plants or plant seeds to be grown in such fields, or the fields (locus), can be selectively treated by applying the isolated peptide or composition of the invention as described herein; whereas the same field may not be treated at ineffective times of the growing season or other fields that are not prone to such attack may go untreated. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

As an alternative to applying an isolated peptide or a composition containing the same to plants or plant seeds in order to impart disease resistance in plants, to effect plant growth, to control insects, to impart stress resistance, and/or modulated biochemical signaling to the plants or plants grown from the seeds, transgenic plants or plant seeds can be utilized. When utilizing transgenic plants, this involves providing a transgenic plant transformed with a DNA molecule encoding a peptide of the invention and growing the plant under conditions effective to permit that DNA molecule to impart disease resistance to plants, to enhance plant growth, to control insects, and/or to impart tolerance to biotic or abiotic stress. Alternatively, a transgenic plant seed transformed with a DNA molecule encoding a peptide of the invention can be provided and planted in soil. A plant is then propagated from the planted seed under conditions effective to permit that DNA molecule to express the peptide and thereby impart disease resistance to the transgenic plant, to enhance plant growth, to control insects, and/or to impart tolerance to biotic or abiotic stress.

In these embodiments, it is also possible to select transgenic plants or plant seeds for carrying out the present invention. For example, for fields known to contain a high nematode content, the transgenic plants or plant seeds can be selectively grown in such fields; whereas non-transgenic plants or plant seeds can be grown in fields containing low nematode content. Similarly, for fields having reduced irrigation, the transgenic plants or plant seeds can be selectively grown in such fields; whereas non-transgenic plants or plant seeds can be grown in fields having adequate irrigation. Likewise, for fields prone to flooding, the transgenic plants or plant seeds can be grown in such fields; whereas non-transgenic plants or plant seeds can be grown in fields that are not prone to flooding. As yet another example of such selection, for fields prone to insect attack at certain times of the growing season, the transgenic plants or plant seeds can be selectively grown in such fields; whereas non-transgenic plants or plant seeds can be grown in fields that are not prone to such insect attack. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of an isolated peptide of the present invention or a composition according to the present invention to a plant or the locus where the plant is growing. As a consequence of such application, the peptide contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of an isolated peptide of the present invention or a composition according to the present invention can be applied to a harvested fruit or vegetable. As a consequence of such application, the peptide contacts cells of the harvested fruit or vegetable, and induces post-harvest disease resistance or desiccation resistance to the treated fruit or vegetables, and/or improved longevity of fruit or vegetable ripeness for the treated fruit or vegetables.

In these embodiments, it is also possible to select plants, cuttings, fruits, vegetables, or the locus to which the isolated peptide or composition of the invention is applied. For example, for harvested cuttings or fruit or vegetables that are being shipped great distances or stored for long periods of time, then these can be selectively treated by applying the isolated peptide or composition of the invention as described herein; whereas harvested cuttings or fruit or vegetables that are being shipped locally and intended to be consumed without substantially periods of storage can be excluded from such treatment.

As an alternative to applying an isolated peptide or a composition containing the same to plants or plant seeds in order to induce desiccation resistance to cuttings removed from ornamental plants, post-harvest disease resistance or desiccation resistance to fruit or vegetables harvested from plants, and/or improved longevity of fruit or vegetable ripeness for fruit or vegetables harvested from plants, transgenic plants or plant seeds can be utilized. When utilizing transgenic plants, this involves providing a transgenic plant transformed with a DNA molecule encoding a peptide of the invention and growing the plant under conditions effective to permit that DNA molecule to induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants. Alternatively, a transgenic plant seed transformed with a DNA molecule encoding a peptide of the invention can be provided and planted in soil. A plant is then propagated from the planted seed under conditions effective to permit that DNA molecule to express the peptide and thereby induce desiccation resistance for cuttings removed from ornamental plants, post-harvest disease resistance or desiccation resistance to fruit or vegetables harvested from the transgenic plants, and/or improved longevity of fruit or vegetable ripeness for fruit or vegetables harvested from the transgenic plants.

In these embodiments, it is also possible to select transgenic plants or plant seeds for carrying out the present invention. For example, transgenic plants or plant seeds can be selected for growing when it is known that harvested cuttings or fruit or vegetables are intended to be shipped great distances or stored for long periods of time post-harvest; whereas non-transgenic plants or plant seeds can be selected for growing when it is known that harvested cuttings or fruit or vegetables are intended to be shipped locally and/or consumed without substantially periods of storage.

Suitable plants include dicots and monocots, including agricultural, silvicultural, ornamental and horticultural plants, whether in a natural or genetically modified form. Exemplary plants include, without limitation, alfalfa, apple, apricot, asparagus, avocados, bananas, barley, beans, beech (*Fagus* spec.), *begonia*, birch, blackberry, blueberry, cabbage, camphor, canola, carrot, castor oil plant, cherry, cinnamon, citrus, cocoa bean, coffee, corn, cotton, cucumber, cucurbit, *eucalyptus*, fir, flax, fodder beet, fuchsia, garlic, geranium, grapes, ground nut, hemp, hop, juneberry, *juncea* (*Brassica juncea*), jute, lentil, lettuce, linseed, melon, mustard, nectarine, oak, oats, oil palm, oil-seed rape, olive, onion, paprika, pea, peach, pear, *pelargonium*, peppers, *petunia*, pine (*Pinus* spec.), plum, poplar (*Populus* spec.), pome fruit, potato, rape, raspberry, rice, rubber tree, rye, sorghum, soybean, spinach, spruce, squash, strawberry, sugar beet, sugar cane, sunflower, tea, teak, tobacco, tomato, triticale, turf, watermelon, wheat and willow (*Salix* spec.), *Arabidopsis thaliana*, Saintpaulia, poinsettia, *chrysanthemum*, carnation, and *zinnia*.

With respect to modified biochemical signaling, this includes both enhancement of certain plant biochemical pathways and diminishment of certain other plant biochemical pathways. Biochemical signaling pathways that can be altered in accordance with the present invention include gene expression and protein production, production of metabolites, and production of signaling molecules/secondary metabolites. Exemplary biochemical signaling pathways and their modifications include, without limitation, induction of nitric oxide production, peroxide production, and other secondary metabolites; agonist of the ethylene signaling pathway and induction of ethylene-responsive gene expression (see Dong et al., *Plant Phys.* 136:3628-3638 (2004); Li et al., *Planta* 239:831-46 (2014); Chang et al., *PLoS One* 10,e0125498 (2015), each of which is hereby incorporated by reference in its entirety); agonist of the salicylic acid signaling pathway and induction of salicylic acid-responsive gene expression (see Dong et al., *Plant J.* 20:207-215 (1999), which is hereby incorporated by reference in its entirety); agonist of the abscisic acid pathway and induction of abscisic acid-responsive gene expression (see Dong et al., *Planta* 221: 313-327 (2005), which is hereby incorporated by reference in its entirety); agonist of the gibberellin signaling pathway and induction of gibberellin-responsive gene expression (see Li et al., *Planta* 239:831-46 (2014), which is hereby incorporated by reference in its entirety); antagonist of jasmonic acid signaling and inhibiting expression of jasmonic acid-responsive genes (see Dong et al., *Plant Phys.* 136:3628-3638 (2004), which is hereby incorporated by reference in its entirety); inducing protease inhibitor expression (see Laluk and Mengiste, *Plant J.* 68:480-494 (2011); Xia et al., *Chin. Sci. Bull* 56: 2351-2358 (2011), each of which is hereby incorporated by reference in its entirety); inducing reactive oxygen species production in plant tissues; inducing immune-related and antimicrobial peptide production, such as, without limitation, peroxidase, superoxide dismutase, chitinase, and β-1,3-glucanase (Wang et al., *J. Agric. Food Chem.* 59:12527-12533 (2011), which is hereby incorporated by reference in its entirety); and inducing expansion gene expression and production (see Li et al., *Planta* 239:831-46 (2014), which is hereby incorporated by reference in its entirety).

With respect to disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: pathogenic *Pseudomonas* spp., pathogenic *Erwinia* spp., pathogenic *Xanthomonas* spp., and pathogenic *Ralstonia* spp. Plants can be made resistant, inter alia, to the following fungi by use of the method of the present invention: *Fusarium* spp. and *Phytophthora* spp.

With regard to the use of the peptides or compositions of the present invention to enhance plant growth, various forms of plant growth enhancement or promotion can be achieved. This can occur as early as when plant growth begins from seeds or later in the life of a plant. For example, plant growth according to the present invention encompasses greater yield, increased plant vigor, increased vigor of seedlings (i.e., post-germination), increased plant weight, increased biomass, increased number of flowers per plant, higher grain and/or fruit yield, increased quantity of seeds produced, increased percentage of seeds germinated, increased speed of germination, increased plant size, decreased plant height (for wheat), greater biomass, more and bigger fruit, earlier fruit coloration, earlier bud, fruit and plant maturation, more tillers or side shoots, larger leaves, delayed leaf senescence, increased shoot growth, increased root growth, altered root/shoot allocation, increased protein content, increased oil content, increased carbohydrate content, increased pigment content, increased chlorophyll content, increased total photosynthesis, increased photosynthesis efficiency, reduced respiration (lower $O_2$ usage), compensation for yield-reducing treatments, increased durability of stems (and resistance to stem lodging), increased durability of roots (and resistance to root lodging), better plant growth in low light conditions, and combinations thereof. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

With regard to the use of the peptides or compositions of the present invention to control pests (including but not limited to insects and nematodes, which are biotic stressors), such pest control encompasses preventing pests from contacting plants to which the peptide or composition of the invention has been applied, preventing direct damage to plants by feeding injury, causing pests to depart from such plants, killing pests proximate to such plants, interfering with insect larval feeding on such plants, preventing pests from colonizing host plants, preventing colonizing insects from releasing phytotoxins, interfering with egg deposition on host plants, etc. The present invention also prevents subsequent disease damage to plants resulting from pest infection.

The present invention is effective against a wide variety of insects (biotic stressors). European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide. The present invention is also effective against nematodes, another class of economically important biotic stressors. Soybean Cyst Nematode (*Heterodera glycines*) is a major pest of soybeans. Reniform Nematode (*Rotylenchulus reniformis*) is a major pest of cotton as can parasitize additional crop species, notably soy and corn. Additional nematode pests include the root knot nematodes of the genus *Meloidogyne* (particularly in cotton, wheat, and barley), cereal cyst nematodes of the genus *Heterodera* (particularly in soy, wheat, and barley), root lesion nematodes of the genus *Pratylenchus*, seed gall nematodes of the genus *Anguina* (particularly in wheat, barley, and rye), and stem nematodes of the genus *Ditylenchus*. Other biotic stressors include arachnids, weeds, and combinations thereof.

With regard to the use of the peptides or compositions of the present invention to impart abiotic stress resistance to plants, such abiotic stress encompasses any environmental factor having an adverse effect on plant physiology and development. Examples of such environmental stress include climate-related stress (e.g., drought, flood, frost, cold temperature, high temperature, excessive light, and insufficient light), air pollution stress (e.g., carbon dioxide, carbon monoxide, sulfur dioxide, $NO_x$, hydrocarbons, ozone, ultraviolet radiation, acidic rain), chemical (e.g., insecticides, fungicides, herbicides, heavy metals), nutritional stress (e.g., over- or under-abundance of fertilizer, micronutrients, macronutrients, particularly potassium, nitrogen derivatives, and phosphorus derivatives), and improved healing response to wounding. Use of peptides of the present invention imparts resistance to plants against such forms of environmental stress.

A further aspect of the present invention relates to the use of the peptides of the present invention as a safener in combination with one or more of the active agents (i.e., in a composition or in separate compositions) for the control of aquatic weeds in a body of water as described in U.S. Publ. No. 20150218099 to Mann, which is hereby incorporated by reference in its entirety.

Yet another aspect of the present invention relates to the use of the peptides of the present invention as a plant strengthener in a composition for application to plants grown under conditions of reduced water irrigation, which composition also includes at least one antioxidant and at least one radiation manager, and optionally at least one plant growth regulator, as described in U.S. Publ. No. 20130116119 to Rees et al., which is hereby incorporated by reference in its entirety.

The methods of the present invention involving application of the peptide or composition can be carried out through a variety of procedures when all or part of the plant is treated, including leaves, stems, roots, propagules (e.g., cuttings), fruit, etc. This may (but need not) involve infiltration of the peptide into the plant. Suitable application methods include high or low pressure spraying, injection, and leaf abrasion proximate to when peptide application takes place. When treating plant seeds, in accordance with the application embodiment of the present invention, the hypersensitive response elicitor protein or polypeptide can be applied by low or high pressure spraying, coating, immersion (e.g., soaking), or injection. Other suitable application procedures can be envisioned by those skilled in the art provided they are able to effect contact of the hypersensitive response elicitor polypeptide or protein with cells of the plant or plant seed. Once treated with the peptides or compositions of the present invention, the seeds can be planted in natural or artificial soil and cultivated using conventional procedures to produce plants. After plants have been propagated from seeds treated in accordance with the present invention, the plants may be treated with one or more applications of the peptides or compositions of the invention to impart disease resistance to plants, to enhance plant growth, to control insects on the plants, to impart biotic or abiotic stress tolerance, to improve desiccation resistance of removed cuttings, to impart post-harvest disease resistance or desiccation resistance to harvested fruit or vegetables, and/or improved longevity of fruit or vegetable ripeness for harvested fruit or vegetables.

The peptides or compositions of the invention can be applied to plants or plant seeds in accordance with the present invention alone or in a mixture with other materials. Alternatively, the peptides or compositions can be applied separately to plants with other materials being applied at different times.

In the alternative embodiment of the present invention involving the use of transgenic plants and transgenic seeds, a peptide of the invention need not be applied topically to the plants or seeds. Instead, transgenic plants transformed with a DNA molecule encoding a peptide of the invention are produced according to procedures well known in the art. A vector suitable for expression in plants (i.e., containing translation and transcription control sequences operable in plants) can be microinjected directly into plant cells by use of micropipettes to transfer mechanically the recombinant DNA. Crossway, *Mol. Gen. Genetics,* 202:179-85 (1985), which is hereby incorporated by reference in its entirety. The genetic material may also be transferred into the plant cell using polyethylene glycol. Krens, et al., *Nature,* 296:72-74 (1982), which is hereby incorporated by reference in its entirety.

Another approach to transforming plant cells with a gene encoding the peptide of the invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes or other fusible lipid-surfaced bodies. Fraley, et al., *Proc. Natl. Acad. Sci. USA,* 79:1859-63 (1982), which is hereby incorporated by reference in its entirety. The DNA molecule may also be introduced into the plant cells by electroporation. Fromm et al., *Proc. Natl. Acad. Sci. USA,* 82:5824 (1985), which is hereby incorporated by reference in its entirety. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25-28° C. *Agrobacterium* is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome. J. Schell, *Science,* 237:1176-83 (1987), which is hereby incorporated by reference in its entirety.

After transformation, the transformed plant cells must be regenerated. Plant regeneration from cultured protoplasts is described in Evans et al., *Handbook of Plant Cell Cultures,* Vol. 1: (MacMillan Publishing Co., New York, 1983); and Nasil I. R. (ed.), *Cell Culture and Somatic Cell Genetics of Plants,* Acad. Press, Orlando, Vol. 1, 1984, and Vol. III (1986), which are hereby incorporated by reference in their entirety.

It is known that practically all plants can be regenerated from cultured cells or tissues. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in disease resistance, enhanced plant growth, control of insects on the plant, abiotic or biotic stress tolerance, improved desiccation resistance of removed cuttings, post-harvest disease resistance or desiccation resistance in harvested fruit or vegetables, and/or improved longevity of fruit or vegetable ripeness for harvested fruit or vegetables.

Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to impart disease resistance to plants, to enhance plant growth, to control insects, to impart abiotic or biotic stress tolerance, to improve desiccation resistance of removed cuttings, to impart post-harvest disease resistance or desiccation resistance in harvested fruit or vegetables, and/or to impart improved longevity of fruit or vegetable ripeness for harvested fruit or vegetables.

When transgenic plants and plant seeds are used in accordance with the present invention, they additionally can be treated with the same materials as are used to treat the plants and seeds to which a peptide of the invention or composition of the invention is applied. These other materials, including peptides or composition of the invention, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the peptides or compositions of the invention to impart disease resistance, enhance growth, control insects, abiotic or biotic stress tolerance, desiccation resistance of removed cuttings, post-harvest disease resistance or desiccation resistance in harvested fruit or vegetables, and/or improved longevity of fruit or vegetable ripeness for harvested fruit or vegetables.

Such transgenic plants may also be treated with conventional plant treatment agents, e.g., bacteriocidal or biocidal agents, protease inhibitors, non-ionic surfactants, fertilizers, herbicides, insecticides, fungicides, nematicides, biological inoculants, plant regulators, and mixtures thereof, as described above.

EXAMPLES

The following examples are provided to illustrate embodiments of the present invention but are by no means intended to limit its scope.

Example 1—Hypersensitive Response Analysis

HR in tobacco was tested as described in Wei, *Science* 257:85-88 (1992), which is hereby incorporated by reference in its entirety. Briefly, peptides were dissolved at a concentration of 500 μg/ml in aqueous solution. Four serial dilutions were performed with an equal volume of water, yielding peptide samples at 500, 250, 125, 62.5, 31.25 μg/ml peptide solutions. *Nicotiana tabacum* cultivar xanthi plants were used at 5-7 weeks old (preflowering). Leaves were lightly punctured with a toothpick in a middle leaf panel. Peptide solutions were then infused via needle-less syringe into the wound, filling the panel. Each peptide sample was infused into a leaf of 2 different plants. The leaves were observed and scored over the next 48 hours for withering and browning, lesions typical of programmed cell death.

Hypersensitive Response testing was performed on many peptides and determined to be negative. Some peptides have yet to be tested, designed as "to be determined" or "TBD" in Table 18 below, but are expected to be HR-negative based on the results for closely related peptides.

TABLE 18

Summary of Hypersensitive Response Results

| Name | SEQ ID NO: | Tobacco HR | Name | SEQ ID NO: | Tobacco HR |
|---|---|---|---|---|---|
| P1-13P-20P | 164 | — | P14 | 113 | — |
| P1-29 | 130 | TBD | P14-22L, 26L | 115 | — |
| P1-31 | 131 | TBD | P14-22L, 26E | 19 | — |
| P3-5 | 156 | — | P14-22A, 26L | 20 | TBD |
| P3-9 | 158 | — | P14-22A, 26E | 21 | TBD |
| P3-10 | 159 | — | P14-22E, 26L | 22 | TBD |
| P4-14S-9A | 57 | — | P14-22E, 26E | 23 | TBD |
| P4-14S-9D | 58 | — | P14-22L, 26A | 26 | — |
| P4-14S-9S | 52 | — | P14-22A, 26A | 27 | TBD |
| P4-14S-9Y | 53 | — | P14-22L, 25-26A | 28 | TBD |
| P4-14S-12D | 59 | — | P14-22L, 28-29A | 29 | TBD |
| P4-14s-13D | 48 | — | P14-22L, 26, 29A | 30 | TBD |
| P4-14S-13F | 134 | — | P14-22L, 28, 32A | 31 | TBD |
| P4-14S-13V | 133 | — | P14-dc2 | 32 | TBD |
| P4-14S-13Q | 54 | — | P14-dc4 | 122 | TBD |
| P4-14S-16S | 55 | — | P14a | 123 | TBD |
| P4-14S-17D | 49 | — | P15-60 | 114 | — |
| P4-14S-20S | 56 | — | P15-61 | 150 | — |
| P4-14S-21D | 50 | — | P15-62 | 151 | — |
| P4-d10, 14, 18 | 62 | — | P15-63 | 148 | TBD |
| P4-d18 | 51 | — | P18-8 | 149 | TBD |
| P4-i10A, 14A, 18A | 68 | — | P18-9 | 142 | TBD |
| P4-i10A | 65 | — | P19-9 | 143 | TBD |
| P4-i14A | 66 | — | P19-10 | 144 | — |
| P4-i18A | 67 | — | P19-12 | 145 | — |
| P4-i21Q | 63 | — | P19-13 | 146 | — |
| P4-i21H | 64 | — | P6a-15D | 147 | — |
| P4-l11 | 132 | — | P6a-11S | 199 | TBD |
| P4-l16 | 140 | TBD | P15b-12S | 204 | TBD |
| P4-l17 | 141 | TBD | P14d-17D | 188 | TBD |
| P14d-7D | 208 | TBD | P14d-17D | 213 | TBD |

TABLE 18-continued

Summary of Hypersensitive Response Results

| Name | SEQ ID NO: | Tobacco HR | Name | SEQ ID NO: | Tobacco HR |
|---|---|---|---|---|---|
| P14d-10D | 209 | TBD | P14d-18D | 214 | TBD |
| P14d-11D | 210 | TBD | P14d-7S | 215 | TBD |
| P14d-14D | 211 | TBD | P14f-17S | 45 | TBD |
| P14d-15D | 212 | TBD | | | |

TBD = To be determined.

Example 2—Peroxide Response Analysis

The ferric-xylenol orange complex assay for hydrogen peroxide (Gay et al., *Analytical Biochemistry* 273:149-55 (1999), which is hereby incorporated by reference in its entirety) was used to determine peroxide production by plant leaf tissue. Briefly, reagent A was prepared by mixing 10 mg of ferrous ammonium sulfate with 133 uL of sulfuric acid in a total volume of 1 mL with water. Reagent B was prepared by mixing 2 g of sorbitol with 9.34 mg of xylenol orange in 80 ml of water. 1M hydrochloric acid was slowly added until the solution turned yellow. The solution was then diluted with water to a total volume of 100 mL, and stored in a dark bottle at 4° C.

Leaves from either tobacco plants (plants grown to 6 true leaves) or soy plants (plants grown to 6 true leaves) were used for the assay. The leaf was first removed from the plant and placed on a paper towel. 0.5 cm leaf tissue circles were then removed from the leaf using a leather punch tool. These discs were then placed into the wells of a 96-well plate. 250 ml of water was added to each disc. The plate was covered with parafilm and rested for 12 hours in the dark. The excess water was then removed and the wells washed with an additional 250 uL of water. The washes were then removed from the wells and replaced with 105 uL of a 0.5 ug/ml solution of peptide in water or water blank, generally in quadruplicate. Where peptide solubility was a problem, pH buffer was added to both the blank and peptide samples. Leaf discs were incubated with the peptides for one hour under fluorescent lighting. 50 ul of the solution from each leaf sample was removed to a new well for chemical analysis.

Just prior to analysis, reagents A and B were freshly mixed in a 1:100 ratio to produce the assay reagent. 200 ul of this mixture was added to each well containing 50 ul of leaf-treated solution. The plate was incubated in the dark for 20 minutes and the absorbance at 595 nm was detected. Results were analyzed using a two-tailed Student's T-test. The results were divided into several response classes. XR++ indicated a positive response with absorbance >0.05 units above the negative control and a Student's T-test $p<0.05$. XR+ indicated an absorbance <0.05 units above the blank and a Student's T-test $p<0.05$. XR weak indicated a response >0.02 units above the negative control with a p-value that was not significant. XR− indicated an absorbance within 0.02 units of the negative control. It should be noted that there can be significant biological variability in the peroxide response due to plant age, location of the disc within the leaf, and other factors. As a result, p-values from the T-test are a guide and not an absolute inclusion criterion.

The results of these studies are summarized in Table 19 below:

TABLE 19

Summary of Peroxide Response

| Name | SEQ ID NO: | Soy | Tobacco |
|---|---|---|---|
| P1-13P-20P | 164 | ++ | − |
| P1-29 | 130 | ND | + |
| P1-31 | 131 | + | − |
| P3-5 | 156 | ND | Weak + |
| P3-9 | 158 | ND | ++ |
| P3-10 | 159 | ND | ++ |
| P4-14S-9A | 57 | ++ | + |
| P4-14S-9D | 58 | Weak+ | + |
| P4-14S-9S | 52 | + | Weak+ |
| P4-14S-9Y | 53 | + | + |
| P4-14S-12D | 59 | + | + |
| P4-14S-13D | 48 | ND | Weak+ |
| P4-14S-13F | 134 | + | Weak+ |
| P4-14S-13V | 133 | + | + |
| P4-14S-13Q | 54 | + | Weak+ |
| P4-14S-16S | 55 | − | ++ |
| P4-14S-17D | 49 | ++ | ++ |
| P4-14S-20S | 56 | − | ++ |
| P4-14S-21D | 50 | ++ | ++ |
| P4-d10, 14, 18 | 62 | ++ | − |
| P4-d18 | 51 | + | ++ |
| P4-i10A, 14A, 18A | 68 | + | − |
| P4-i10A | 65 | ++ | ++ |
| P4-i14A | 66 | ++ | ++ |
| P4-i18A | 67 | ++ | ++ |
| P4-116 | 140 | + | ++ |
| P4-117 | 141 | ++ | + |
| P14 | 113 | + | Weak+ |
| P14-22L, 26L | 115 | Weak+ | − |
| P14-22L, 26E | 19 | ++ | Weak+ |
| P14-22A, 26L | 20 | + | + |
| P14-22A, 26E | 21 | Weak+ | − |
| P14-22E, 26L | 22 | ++ | ++ |
| P14-22E, 26E | 23 | + | Weak+ |
| P14-22L, 26A | 26 | + | + |
| P14-22A, 26A | 27 | ++ | − |
| P14-22L, 25-26A | 28 | ++ | − |
| P14-22L, 28-29A | 29 | Weak+ | − |
| P14-22L, 32-33A | 30 | ++ | + |
| P14-22L, 26, 29A | 31 | ++ | − |
| P14-22L, 28, 32A | 32 | ++ | − |
| P14-dc2 | 122 | + | ++ |
| P14-dc4 | 123 | ++ | ++ |
| P14a | 114 | ++ | ++ |
| P15-60 | 150 | ++ | ++ |
| P15-61 | 151 | ++ | + |
| P15-62 | 148 | − | − |
| P15-63 | 149 | − | − |
| P18-8 | 142 | + | + |
| P18-9 | 143 | + | + |
| P14d-7D | 208 | ND | + |
| P14d-10D | 209 | ND | ++ |
| P14d-11D | 210 | ND | + |
| P14d-14D | 211 | ND | ++ |
| P14d-15D | 212 | ND | ++ |
| P14d-17D | 213 | ND | ++ |
| P14d-18D | 214 | ND | ++ |
| P14d-7S | 215 | ND | ++ |
| P14f-17S | 45 | ND | ++ |
| P6a-15D | 199 | ND | + |
| P6a-11S | 204 | ND | − |
| P15b-12S | 188 | ND | ++ |
| P15b-21S | 193 | ND | ++ |
| P18min-11S | 94 | ND | + |
| P18min-7D | 85 | ND | ++ |
| P19min-10S | 107 | ND | ++ |
| P19min-11S | 108 | ND | + |
| P19min-13S | 109 | ND | ++ |
| P25min-15S | 81 | ND | ++ |
| P25-9D | 224 | ND | + |
| P25-12 | 153 | + | + |
| P25-13 | 154 | ND | + |
| P25-14 | 155 | ND | ++ |

ND: Not determined

In general, the vast majority of peptides tested XR+ in Soy. However, tobacco was more discriminating. Most peptides that were a single mutation from an HR+ sequence were XR+ in tobacco. Even a second mutation often still resulted in XR+ phenotype. However, tests on p14 variants showed the mutation of three leucine residues to alanine generally resulted in a loss of XR elicitation. Likewise, C-terminal truncated variants of p15 (p15-62 and p15-63) were XR– in tobacco.

Example 3—Root & Shoot Growth Analysis

Peptides were tested for biological effects on the allocation of growth resources to the shoot (above ground) and root (below ground). Peptides were dissolved at 0.2, 2, or 5 μg/ml in a total volume of 100 ml deionized water. Corn or soybean seeds were then soaked for one hour in the peptide solution. Untreated control (UTC) plants were soaked in deionized water. Clear plastic 300 ml beverage cups (Solo®, Dart Container Corporation) were prepared for planting by marking the bottom with a cross, dividing the bottom into four equal quadrants. The cups were then filled with Sunshine Mix #1 soil (SunGro Horticulture) sieved to ¼". 100 ml of water was added to the soil. Treated seeds were then planted by pressing the seed lightly into the top of the soil. The seeds were then covered with an additional 50 ml of loose soil. Seeds were allowed to germinate and grow for 12-14 days.

The length of the shoot was measured as the distance from the soil to the lightly stretched tip of the highest leaf for each plant. Plants that failed to germinate or exhibited stunted growth were removed from the trial. Stunting was defined as lacking a fully expanded true leaf at time of data collection or having an expanded true leaf judged by eye to be <½ the average leaf area of the treatment group. Generally, 30 seeds were planted per treatment group and 15-25 plants were used for data collection.

Root growth was estimated by counting the number of times that a primary root crosses the quadrant marks on the bottom of the cup. These were often observed along the bottom circumference of the cup, although some were visible along the side of the container and were counted as if crossing a vertical extension of the quadrant line. This number was divided by 4 to produce a root growth index. This index was found to correlate ~90% with measured total primary root length (sum of lengths of all primary roots after rinsing soil from roots and measuring directly).

The results of these studies are summarized in Table 20 below. Each number indicates the percentage increase over the untreated control values. An asterisk indicates that the difference was statistically significant with $p<0.05$ as determined by Student's T-test.

TABLE 20

Summary of Root & Shoot Growth

| Peptide (Host) | SEQ ID NO: | Rate (ug/ml) | Root | Shoot |
|---|---|---|---|---|
| P4-14S-9A (corn) | 57 | 0.2 | 4.8 | 3.9%* |
| P4-14S-9A (soy) | 57 | 5.0 | 2.5% | 6.5%* |
| P4-14S-9A (soy) | 57 | 2.0 | 4.3% | 5.0% |
| P4-14S-16S (soy) | 55 | 2.0 | 28.3%* | −11.3% |
| P4-14S-16S (soy) | 55 | 0.2 | 28.3% | −2.0% |
| P4-14S-20S (soy) | 56 | 5.0 | 2.2% | 5.8%* |
| P14 (soy) | 113 | 5.0 | 24.9%* | 4.4% |
| P14a (soy) | 114 | 5.0 | 10.3%* | −3.5% |
| P14a (soy) | 114 | 0.2 | −2.7% | 8.7%* |

Increased root growth (shown in p4-14s-16s, p14, and p14a) increases the water-gathering ability of the plant and will increase drought and flooding resistance. Conversely, increased shoot growth (as in p4-14s-9a, p4-14s-20s, and p14a soy at 0.2 μg/ml) increases light-gathering and energy conversion. It is notable that p14a can cause increases in either root or shoot growth depending on dosage. P4-14s-16s causes a strong shift in resource allocation to root growth.

Example 4—Growth Tests

Soy seeds (or corn seeds, as indicated) were planted in flats with 2 seeds per cell within the flat at a greenhouse facility. The seeds were allowed to germinate and the smaller plant is culled, leaving one plant per cell. Once the first true leaves are fully expanded and the second leaves are beginning to expand, the plants were initially measured for height. This was performed by stretching the highest leaf upward and measuring the distance to the soil. Peptides were dissolved in water at the indicated concentrations (Table 21 below). The plants were then treated with a foliar spray using widely available spray bottles until liquid was dripping from the leaves. Six flats of 14 plants each were treated per condition (peptide or control). Designated untreated control plants were sprayed with water. The plants were allowed to grow for 14 days. The height of the plants was again measured and compared to the original height to quantify growth. Finally, the plants were harvested by removing the shoots (all above-ground material). For some experiments, this was weighed upon harvesting to determine the fresh mass (including water weight). The shoots were then dried at 70° C. for 72 hours, and again weighed to determine dry biomass. Although this method uses a similar measure (growth) as in Example 3 above, the treatment method is different (seed soak vs. foliar spray). As a result, the experimental outcomes may diverge.

TABLE 21

Summary of Growth Measurements

| Peptide | SEQ ID NO: | Rate (ug/ml) | Growth increase (%) | Dry biomass increase (%) | Fresh mass increase (%) |
|---|---|---|---|---|---|
| P1-29 (corn) | 130 | 2.0 | 7.8 | 5.7 | 5.1 |
| P4-14S-9A | 57 | 2.0 | 11.9% | 10.8% | ND |
| P14 | 113 | 2.0 | 25.8% | 1.6% | ND |
| P14 | 113 | 5.0 | 31.4% | 3% | ND |
| P4-14S-12D | 59 | 5.0 | −4.2% | −3.6% | ND; resistant to wilting |
| P14a | 114 | 5.0 | 8.9% | 10.6 | 83.3% |
| P14a | 114 | 2.0 | 3.4% | 11.0% | 57.9% |
| P14a | 114 | 0.2 | 14.7% | 12.6% | 46.8% |
| P14-32 | 124 | 5.0 | 12.5% | 14% | 33.3% |
| P14-32 | 124 | 2.0 | 1.7% | 8.2% | 27.6% |
| P14-32 | 124 | 0.2 | 9.5% | 6.8% | 2.9% |
| P14-dc4 | 123 | 5.0 | −17% | −7.6% | −15.4% |
| P14-dc4 | 123 | 2.0 | −4.6 | −1.6% | 0.4% |
| P14-dc4 | 123 | 0.2 | 2.6% | 5.6% | 7.5% |

ND: Not determined

Several of the studied peptides cause increases in growth and dry biomass (p4-14s-9a, p14, p14a, and p14-32). In addition, several peptides caused increased conservation of water as compared with UTC plants which suffered drought stress at trial completion. Conserved water content was indicated by >10% increase in fresh mass, such as found in p14a- and p14-32-treated plants. The growth effect was not limited to soy; corn also exhibited a modest growth benefit upon peptide treatment with p1-29.

Notably, P14-dc4, which incorporates a truncated C-terminus, seems to lose the significant growth, dry biomass, and fresh mass benefits observed for p14. By comparison, removal of the P14 N-terminal sequence (P14a samples) still results in increases for all 3 measures.

Example 5—Induction of Resistance to Tobacco Mosaic Virus

Peptides were tested for the induction of resistance to tobacco mosaic virus (TMV) in tobacco. Briefly, three tobacco plants at 6-8 weeks old were selected per group (samples and controls). The bottom-most leaf of the plant was covered and the plant was sprayed with a solution of water (negative control), peptide, or Proact (positive control). The spray was applied until the leaves were fully wetted, indicated by liquid dripping from the leaves. The plants were then allowed to dry and the leaf covering was removed.

Three days post-treatment, the previously-covered leaf and a leaf on the opposite side of the plant were then lightly dusted with diatomaceous earth and 20 ul of a 1.7 ug/ml solution of purified tobacco mosaic virus was applied. The TMV solution was then spread across the leaf surface by lightly rubbing solution and the diatomaceous earth across the surface of the leaves. Two minutes after inoculation, the diatomaceous earth was rinsed off the leaves with water. 3 days after TMV inoculation, the leaves were scored based on the number of TMV lesions observed. The leaf was also scored for signs of the hypersensitive response, including yellowing and wilting of the affected leaves.

Effectiveness described in Table 22 refers to the % decline in TMV lesions on treated vs UTC plants. A reduction of TMV on covered leaves indicates a systemic immune response in the plant while reduction on uncovered leaves indicates a local response. Asterisks indicate that the P-value derived from a T-test was <0.05.

TABLE 22

Summary of TMV Resistance

| Peptide | SEQ ID NO: | Concentration (ug/ml) | Effectiveness Uncovered (%) | Effectiveness Covered (%) |
|---|---|---|---|---|
| P1-29 | 130 | 10 | 44 | 18 |
| P1-31 | 131 | 20 | 95* | 88* |
| P3-5 | 156 | 10 | 66 | 94* |
| P3-10 | 159 | 20 | 94* | 95* |
| P4-14S-9A | 57 | 5.0 | 84* | 86* |
| P4-14S-9D | 58 | 10 | 89 | 52 |
| P4-14S-12D | 59 | 5.0 | 61* | 60* |
| P4-14S-13Q | 54 | 10 | 40 | 61* |
| P4-14S-16A | 60 | 10 | 1 | 3 |
| P4-14S-16S | 55 | 10 | 72* | 46 |
| P4-14S-16V | 135 | 10.0 | 78 | 85* |
| P4-14S-17F | 136 | 10 | 94 | 57 |
| P4-14S-20S | 56 | 10 | 59* | −45 |
| P4-14S-20V | 137 | 10 | −26 | −29 |
| P4-14S-21D | 50 | 10 | 49 | 48 |
| P4-111 | 132 | 10 | 58 | 65 |
| P4-115 | 139 | 20 | 87* | 87* |
| P4-116 | 140 | 10 | 52 | 0* |
| P4-d18 | 51 | 10 | 65 | 15 |
| P4-d10, 14, 18 | 62 | 10 | 55 | 37 |
| P4-i10a | 65 | 10 | 92 | 81 |
| P4-i14a | 66 | 10 | 75 | 77 |
| P4-i18a | 67 | 10 | 81 | 50 |
| P4-i10, 14, 18a | 68 | 10 | 75 | 69 |
| P14-22L, 26L | 115 | 20 | 65* | 67* |
| P14-22L, 26E | 19 | 20 | 70* | 91* |
| P14-22A, 26L | 20 | 20 | 48 | 62 |
| P14-22A, 26E | 21 | 20 | 91* | 85* |
| P14-22E, 26L | 22 | 20 | 61* | 84* |
| P14-22E, 26E | 23 | 20 | 74* | 62 |
| P14-22E, 26A | 25 | 20 | 89* | 88* |
| P14-22L, 26A | 26 | 20 | 72* | 83* |
| P14-22L, 25-26A | 28 | 10 | 87* | 75* |
| P14-22L, 28-29A | 29 | 10 | 83* | 84* |
| P14-22L, 32-33A | 30 | 10 | 91* | 69* |
| P14-22, 26A | 27 | 10 | 92* | 93* |
| P14-22L, 26, 29A | 31 | 10 | 85* | 70* |
| P14-22L, 28, 32A | 32 | 10 | 71* | 37* |
| P14-31 | 129 | 20 | 85* | 87* |
| P14-32 | 124 | 20 | 90* | 82* |
| P14-dc1 | 121 | 10 | 65* | 46 |
| P14-dc2 | 122 | 10 | 76* | 56 |
| P14-dc4 | 123 | 10 | 34 | 19 |
| P14-39 | 160 | 20 | 72* | 66* |
| P14-41 | 245 | 20 | 86* | 61* |
| P14d-7D | 208 | 20 | 71* | 55* |
| P14d-10D | 209 | 20 | 84* | 84* |
| P14d-11D | 210 | 20 | 81* | 87* |
| P14d-14D | 211 | 20 | 84* | 35 |
| P14d-15D | 212 | 20 | 87* | 74* |
| P14d-17D | 213 | 20 | 68* | 65* |
| P14d-18D | 214 | 20 | 52 | 32 |
| P14d-7S | 215 | 20 | −112 | 23 |
| P14f-17S | 45 | 20 | 94* | 84* |
| P6a-15D | 199 | 20 | 74* | 74* |
| P6a-11S | 204 | 20 | 71* | 88* |
| P15b-12S | 188 | 20 | 76* | 47 |
| P15b-21S | 193 | 20 | 100* | 97* |
| P18min-11S | 94 | 20 | −90 | −274 |
| P18min-7D | 85 | 20 | 26 | 29 |
| P19min-10S | 107 | 20 | 81* | 94* |
| P19min-11S | 108 | 20 | 71* | 45 |
| P19min-13S | 109 | 20 | 35 | −70 |
| P25min-15S | 81 | 20 | 81* | 74* |
| P25-9D | 224 | 20 | 78* | 55 |
| P15-60 | 150 | 20 | 55 | 13 |
| P15-61 | 151 | 20 | 55* | 7 |
| P15-62 | 148 | 20 | 94* | −122 |
| P15-63 | 149 | 20 | 90* | 74* |
| P18-8 | 142 | 20 | 55 | 78* |
| P18-9 | 143 | 20 | 65* | 52 |
| P25-9 | 152 | 20 | 68 | 87* |
| P25-12 | 153 | 20 | 77* | 58 |
| P25-14 | 155 | 20 | 52 | −87 |

Several HR-negative peptides cause significant local and systemic responses: P4-14S-9A, P4-14S-17A, P4-14S-12D, and P4-14S-16V produced the best results. In general, most peptides exhibited some anti-TMV activity. However, peptides with a larger C-terminal truncation as compared with an intact HR-box (see co-pending U.S. patent application Ser. No. 14/872,298, entitled "Hypersensitive Response Elicitor Peptides and Use Thereof", filed Oct. 1, 2015, which is hereby incorporated by reference in its entirety) (e.g., p4-116, P14-dc4), exhibit reduced effectiveness against TMV infection. A shorter C-terminal truncation generally elicited TMV resistance at a slightly weaker rate (50-75% control). Greater disruption of residue spacing in P4-d10, 14,18 also exhibited a moderate reduction in effectiveness against TMV infection. Also, mutation of some leucine positions seemed associated with weaker TMV responses: P19 min-135, P18 min-7D, P18 min-11S, P14d-18D, P4-14S-20V, P4-14S-20S, P4-14s-16A. Notably, although it contains a several hydrophobic sequences, P25-14 exhibits weaker control of TMV infection. A systematic investigation of mutation of the important leucine and isoleucine residues over several HR-eliciting sequences revealed that mutations at the several locations can cause a reduction in the immune response. Mutation of the first hydrophobic residue (in p14d-7S, p18 min-7D, and p25-9D) can cause reduced efficacy on covered leaves, indicating a reduction in systemic immune response. P15b-12S also exhibits a similar reduction in systemic responses in the covered leaf. P19 min-13S exhibits poor immune activation. One can remove the last hydrophobic doublet, which still allowed for anti-TMV activity (for example in P1-31 and P1-111). However, a further shortened hydrophobic sequence is associated with a reduction in activity against TMV, as demonstrated by P4-116 and P14-dc4.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. An isolated peptide comprising the amino acid sequence of

L-X-X-(L/I)-(L/I)-X-X-(L/I/V)-(L/I/V)    (SEQ ID NO: 116), wherein the peptide is free of cysteine and methionine;

each X at positions 2, 3, 6, 7 is independently selected from the group consisting of G, A, S, T, D, isoD, E, γ-glutamate, Q, N, K, and R;

the peptide comprises up to 24 amino acids at the N-terminal end of SEQ ID NO: 116, up to 10 amino acids at the C-terminal end of SEQ ID NO: 116, or both, except that the amino acid sequence of the peptide does not comprise (L/I/V/F)-X-X-(L/I/V/F)-(L/I)-X-X-(L/I/V)-(L/I)-X-X-(L/I/V/F)-(L/I/V/F) (SEQ ID NO: 125) where each X at positions 2, 3, 6, 7, 10, 11 is any amino acid;

the peptide has a Kyte Doolittle hydropathy index of less than 0.3; and the peptide induces an active plant response, but does not induce a hypersensitive response, when applied to mechanically disrupted plant tissue.

2. The isolated peptide according to claim 1, wherein the peptide comprises up to 20 amino acids at the N-terminal end of SEQ ID NO: 116, up to 7 amino acids at the C-terminal end of SEQ ID NO: 116, or both.

3. The isolated peptide according to claim 1, wherein the amino acid sequence of the peptide contains no lysine or arginine residues except optionally at the C-terminal end.

4. The isolated peptide according to claim 1, wherein each X at positions 2, 3, 6, 7 of SEQ ID NO: 116 is independently selected from the group consisting of G, A, S, T, D, isoD, E, γ-glutamate, Q, and N, and wherein the peptide further comprises an arginine residue at the C-terminal end of the peptide.

5. The isolated peptide according to claim 1, wherein the isolated peptide is characterized by one or more of: (i) stable when dissolved in water or aqueous solution, (ii) resistant to chemical degradation when dissolved in an aqueous buffer solution containing a biocide, (iii) solubility of greater than about 0.1% in water or aqueous solution.

6. The isolated peptide according to claim 1, wherein the active plant response induced by the peptide is selected from the group consisting of peroxide induction, enhanced growth, pathogen resistance, biotic or abiotic stress resistance, and modified biochemical signaling.

7. The isolated peptide according to claim 1, wherein the peptide is at least 90% pure.

8. The isolated peptide according to claim 1, wherein the peptide is a fusion polypeptide comprising a second amino acid sequence coupled via peptide bond to the amino acid sequence.

9. The isolated peptide according to claim 8, wherein the second amino acid sequence includes a purification tag.

10. The isolated peptide according to claim 9, wherein the second amino acid sequence further includes a cleavable linker sequence between the purification tag and the amino acid sequence.

11. The isolated peptide according to claim 8, wherein the peptide is a fusion polypeptide comprising a first amino acid sequence for said peptide linked to a second amino acid sequence for said peptide.

12. A fusion polypeptide comprising a plurality of amino acid sequences linked together in series, one of the plurality of amino acid sequences comprising a peptide according to claim 1.

13. A composition comprising one or more peptides according to claim 1 and a carrier.

14. The composition according to claim 13, wherein the composition is a clarified cell extract.

15. The composition according to claim 13 further comprising an additive selected from the group consisting of fertilizer, herbicide, insecticide, fungicide, nematicide, a bactericidal agent, a biological inoculant, a plant regulator, and mixtures thereof.

16. The composition according to claim 15, wherein the additive comprises either:

(i) clothianidin, a combination of clothianidin and *Bacillus firmus*, imidicloprid, or a combination of imidicloprid and *Bacillus firmus*; or (ii) thiamethoxam; a combination of thiamethoxam, mefenoxam, and fludioxynil; a combination of thiamethoxam, mefenoxam, fludioxynil and azoxystrobin; a combination of thiamethoxam and abamectin; a combination of thiamethoxam, abamectin, and a Pasteuria nematicide; or a combination of thiamethoxam, mefenoxam, fludioxynil, azoxystrobin, thiabendazole, and abamectin; or (iii) a biological inoculant comprising a *Bradyrhizobium* spp., a *Bacillus* spp., or a combination of a *Bradyrhizobium* spp. and a *Bacillus* spp.

17. The composition according to claim 13, wherein the carrier is an aqueous carrier.

18. The composition according to claim 17, wherein the aqueous carrier further comprises one or more of a biocidal agent, a protease inhibitor, a non-ionic surfactant, or a combination thereof.

19. The composition according to claim 13, wherein the carrier is a solid carrier in particulate form.

20. The composition according to claim 19, wherein the solid carrier is a dry powder.

21. A method of imparting disease resistance to plants comprising:
applying an effective amount of an isolated peptide according claim 1 to a plant or plant seed or the locus where the plant is growing or is expected to grow, wherein said applying is effective to impart disease resistance.

22. A method of enhancing plant growth comprising:
applying an effective amount of an isolated peptide according to claim 1 to a plant or plant seed or the locus where the plant is growing or is expected to grow, wherein said applying is effective to enhance plant growth.

23. A method of increasing a plant's tolerance and resistance to biotic stress comprising:
applying an effective amount of an isolated peptide according to claim 1 to a plant or plant seed or the locus where the plant is growing or is expected to grow, wherein said applying is effective to increase the plant's tolerance and resistance to biotic stress factors selected from the group consisting of insects, arachnids, nematodes, weeds, and combinations thereof.

24. A method of increasing a plant's tolerance to abiotic stress comprising:
applying an effective amount of an isolated peptide according to claim 1 to a plant or plant seed or the locus where the plant is growing or is expected to grow, wherein said applying is effective to increase the plant's tolerance to abiotic stress factors selected from the group consisting of salt stress, water stress, ozone stress, heavy metal stress, cold stress, heat stress, nutritional stress, and combinations thereof.

* * * * *